US012758218B2

(12) United States Patent
Lee et al.

(10) Patent No.: US 12,758,218 B2
(45) Date of Patent: Oct. 13, 2026

(54) END TOOL, CARTRIDGE, SURGICAL INSTRUMENT, AND OPERATING METHOD OF SURGICAL INSTRUMENT

(71) Applicant: LIVSMED INC., Seongnam-si (KR)

(72) Inventors: Jae Yeong Lee, Seongnam-si (KR); Hee Jin Kim, Seoul (KR); Jwa Nyun Kim, Yongin-si (KR); Dong Hoon Kang, Seoul (KR); Tae Jin Park, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 44 days.

(21) Appl. No.: 18/765,537

(22) Filed: Jul. 8, 2024

(65) Prior Publication Data

US 2025/0186044 A1 Jun. 12, 2025

(30) Foreign Application Priority Data

Dec. 7, 2023 (KR) ........................ 10-2023-0176315

(51) Int. Cl.

| | |
|---|---|
| ***A61B 17/072*** | (2006.01) |
| ***A61B 17/00*** | (2006.01) |
| ***A61B 90/00*** | (2016.01) |

(52) U.S. Cl.

CPC .. *A61B 17/07207* (2013.01); *A61B 17/00234* (2013.01); *A61B 90/06* (2016.02); *A61B 2017/00075* (2013.01); *A61B 2017/00398* (2013.01); *A61B 2017/00407* (2013.01); *A61B 2017/00477* (2013.01); *A61B 2017/07271* (2013.01); *A61B 2017/07285* (2013.01)

(58) Field of Classification Search

CPC ................ A61B 17/068; A61B 17/072; A61B 17/07207; A61B 2017/07278

See application file for complete search history.

(56) References Cited

U.S. PATENT DOCUMENTS

| | | | | |
|---|---|---|---|---|
| 10,098,638 | B2 * | 10/2018 | Viola | A61B 17/00234 |
| 10,213,202 | B2 * | 2/2019 | Flanagan | A61B 17/072 |
| 10,368,867 | B2 * | 8/2019 | Harris | A61B 17/105 |
| 10,736,628 | B2 * | 8/2020 | Yates | G16Z 99/00 |
| 10,918,386 | B2 * | 2/2021 | Shelton, IV | A61B 17/32 |
| 11,090,046 | B2 * | 8/2021 | Shelton, IV | A61B 17/0686 |
| 12,490,980 | B2 * | 12/2025 | Shelton, IV | A61B 17/07207 |
| 2011/0006103 | A1 * | 1/2011 | Laurent | A61B 17/068 227/176.1 |

(Continued)

FOREIGN PATENT DOCUMENTS

| | | |
|---|---|---|
| JP | 2017-508508 A | 3/2017 |
| JP | 2020-501791 A | 1/2020 |

(Continued)

*Primary Examiner* — Gloria R Weeks

(74) *Attorney, Agent, or Firm* — Bridgeway IP Law Group, PLLC; Sang Ho Lee; Hyun Woo Shin

(57) ABSTRACT

There is provided a surgical instrument including an end tool including a jaw, a driving part, and a detection member, wherein the jaw is formed to accommodate at least one region of an operation member movable in one direction, the driving part is formed to provide a driving force necessary for the operation member to move, the detection member detects driving information of the driving part, and position information of the operation member is identified through the driving information detected by the detection member.

11 Claims, 74 Drawing Sheets

(56) References Cited

U.S. PATENT DOCUMENTS

| | | | | |
|---|---|---|---|---|
| 2011/0163148 | A1 | 7/2011 | Wenchell et al. | |
| 2011/0215132 | A1 | 9/2011 | Aranyi et al. | |
| 2014/0291378 | A1 * | 10/2014 | Shelton, IV | A61B 17/07207 227/175.2 |
| 2018/0360456 | A1 * | 12/2018 | Shelton, IV | A61B 17/07207 |
| 2019/0201137 | A1 * | 7/2019 | Shelton, IV | G16H 50/20 |
| 2020/0305864 | A1 * | 10/2020 | Yates | A61B 17/32 |
| 2022/0105638 | A1 * | 4/2022 | Zhang | B25J 13/06 |
| 2022/0133318 | A1 * | 5/2022 | Hudson | A61B 90/90 227/175.1 |

FOREIGN PATENT DOCUMENTS

| | | | |
|---|---|---|---|
| KR | 10-1993-0009574 | A | 6/1993 |
| KR | 10-2006-0048865 | A | 5/2006 |
| KR | 10-2122508 | B1 | 6/2020 |
| WO | 2022/118166 | A1 | 6/2022 |

* cited by examiner

END TOOL, CARTRIDGE, SURGICAL INSTRUMENT, AND OPERATING METHOD OF SURGICAL INSTRUMENT

CROSS-REFERENCE TO RELATED APPLICATION

This application is based on and claims priority under 35 U.S.C. § 119 to Korean Patent Application No. 10-2023-0176315, filed on Dec. 7, 2023, in the Korean Intellectual Property Office, the disclosure of which is incorporated by reference herein in its entirety.

BACKGROUND

1. Field

The present disclosure relates to an end tool, a cartridge, a surgical instrument, and an operation method of a surgical instrument.

2. Description of the Related Art

In recent years, laparoscopic surgery has been actively used to reduce postoperative recovery time and complications through small incisions. The laparoscopic surgery is a surgical method in which a plurality of small holes are drilled in the abdomen of a patient and the inside of the abdominal cavity is observed through these holes, and is widely used in general surgery and the like.

In performing such laparoscopic surgery, various instruments are being used. For example, suturing instruments that are inserted into the body to suture the surgical site within the abdominal cavity are used, and a surgical stapler that uses medical staples to suture the surgical site is used as the suturing instrument.

In general, a surgical stapler is a medical instrument that is often used for cutting and anastomosis of an organ in abdominal and thoracic surgery. The surgical stapler includes an open stapler used in thoracotomy and laparotomy and an endo stapler used in thoracoscopic surgery and celioscopic surgery.

The surgical stapler has advantages of not only shortening operation time since cutting of a surgical site and anastomosis of an organ are simultaneously performed, but also accurately suturing the surgical site. In addition, the surgical stapler has advantages of a faster recovery and a smaller scar than those when tissue is cut and stapled using a surgical stapling thread, and thus has been widely used in modern surgical operations. In particular, the surgical stapler has been widely used in cancer surgery to cut cancer tissue and suture a cut site.

SUMMARY

The present disclosure is directed to providing a surgical instrument and an operation method of a surgical instrument, capable of precisely and easily controlling the progression of one or more steps involved in performing a laparoscopic surgery or various other surgeries.

Additional aspects will be set forth in part in the description which follows and, in part, will be apparent from the description, or may be learned by practice of the presented embodiments of the disclosure.

An embodiment of the present disclosure discloses a surgical instrument including an end tool including a jaw, a driving part, and a detection member, wherein the jaw is formed to accommodate at least one region of an operation member movable in one direction, the driving part is formed to provide a driving force necessary for the operation member to move, the detection member detects driving information of the driving part, and position information of the operation member is identified through the driving information detected by the detection member.

In the present embodiment, driving information of the driving part necessary for the operation member to move an entire distance that the operation member can move in the jaw may be set as reference information, and the position information of the operation member may be determined by comparing the driving information detected by the detection member with the reference information.

In the present embodiment, the driving part may include a motor member, the reference information may include information on a rotation amount of the motor member necessary for the operation member to move an entire distance that the operation member can move from a distal end to a proximal end of the jaw, the detection member may be formed to detect the rotation amount of the motor member, and the position information of the operation member may be determined by comparing the reference information with the rotation amount of the motor member detected by the detection member.

In the present embodiment, the driving part may include a motor member, and one or more pulleys connected thereto and configured to transmit the driving force to the operation member, the reference information may include information on a rotation amount of the pulley necessary for the operation member to move an entire distance that the operation member can move from a distal end to a proximal end of the jaw, the detection member may detect a rotational motion of the pulley, and the position information of the operation member is determined by comparing the reference information with the rotation amount of the pulley detected by the detection member.

In the present embodiment, the detection member may be disposed inside the driving part or may be integrally formed with the driving part.

In the present embodiment, the surgical instrument may include a manipulation part configured to manipulate an operation of the end tool, wherein the driving part and the detection member may be disposed inside the manipulation part.

In the present embodiment, whether the operation member reaches a set stop position, which is set in advance, may be determined using the position information of the operation member, and the operation member may be formed to stop its forward movement upon reaching the set stop position and remain stationary for a set waiting time, and to resume the forward movement or change into a state capable of forward movement after the set waiting time.

In the present embodiment, the set stop position may be a position corresponding to a close motion completion state of the jaw, and as the operation member moves after the set waiting time, a stapling process of the end tool may proceed to a firing state.

Another embodiment of the present disclosure discloses a surgical instrument including an end tool including a jaw, a moving member, and a detection member, wherein the jaw is formed to accommodate at least one region of an operation member movable in one direction, the moving member is disposed in the jaw and moves in at least one direction, the operation member is moved by the moving member by being in contact therewith, the detection member is formed to detect motion information of the moving member, and position information of the operation member is identified through the motion information detected by the detection member.

In the present embodiment, motion information of the moving member necessary for the operation member to move an entire distance that the operation member can move in the jaw may be set as reference information, and the position information of the operation member may be determined by comparing the motion information detected by the detection member with the reference information.

In the present embodiment, the moving member may be formed to linearly reciprocate in a longitudinal direction between a distal end and a proximal end of the jaw.

In the present embodiment, the reference information may include information on the number of reciprocating movements of the moving member necessary for the operation member to move an entire distance that the operation member can move from a distal end to a proximal end of the jaw, the detection member may detect motion information including the number of linear reciprocating movements of the moving member, and the position information of the operation member may be determined by comparing the reference information with the number of reciprocating movements of the moving member detected by the detection member.

In the present embodiment, the operation member may include a ratchet member including one or more ratchets formed in a region facing the moving member, and the moving member may include recesses formed to be engaged with the ratchets.

In the present embodiment, whether the operation member reaches a set stop position, which is set in advance, may be determined using the position information of the operation member, and the operation member may be formed to stop its forward movement upon reaching the set stop position and remain stationary for a set waiting time, and to resume the forward movement or change into a state capable of forward movement after the set waiting time.

In the present embodiment, the set stop position may be a position corresponding to a close motion completion state of the jaw, and as the operation member moves after the set waiting time, a stapling process of the end tool may proceed to a firing state.

Another embodiment of the present disclosure discloses a surgical instrument including an end tool including a jaw, and a detection member, wherein the jaw is formed to accommodate at least one region of an operation member movable in one direction, and includes a backward movement wire having at least one region disposed in the jaw, and connected to the operation member to move the operation member backward toward a proximal end of the jaw in a longitudinal direction, the detection member is formed to detect motion information of the backward movement wire, and position information of the operation member is identified through the motion information detected by the detection member.

In the present embodiment, information on an entire distance that the operation member can move in the jaw may be set as reference information, and the position information of the operation member may be determined by comparing the motion information of the backward movement wire detected by the detection member with the reference information. In the present embodiment, when the operation member moves forward, the backward movement wire may be moved forward by the operation member without transmitting a driving force to the operation member, and the detection member may be formed to detect position or displacement information of the backward movement wire while the backward movement wire moves forward.

In the present embodiment, the operation member may be moved backward by a driving force resulting from a backward movement of the backward movement wire, and the detection member may be formed to detect position or displacement information of the backward movement wire while the backward movement wire moves backward.

In the present embodiment, the detection member may have the form of a proximity sensor, which detects the backward movement wire.

In the present embodiment, the detection member may be disposed in one region of the jaw to be adjacent to the backward movement wire.

In the present embodiment, the end tool may include an end tool shaft located on a side of a manipulation part of the surgical instrument, in a direction opposite to a direction facing the jaw, and the detection member may be disposed in an inner space of the end tool shaft at a position overlapping the backward movement wire.

In the present embodiment, the detection member may be formed to detect driving information of a driving part that provides a driving force necessary for the backward movement wire to move.

In the present embodiment, the surgical instrument may include a manipulation part configured to manipulate an operation of the end tool, wherein the driving part and the detection member may be disposed inside the manipulation part.

In the present embodiment, whether the operation member reaches a set stop position, which is set in advance, may be determined using the position information of the operation member, and the operation member may be formed to stop its forward movement upon reaching the set stop position and remain stationary for a set waiting time, and to resume the forward movement or change into a state capable of forward movement after the set waiting time.

In the present embodiment, the set stop position may be a position corresponding to a close motion completion state of the jaw, and as the operation member moves after the set waiting time, a stapling process of the end tool may proceed to a firing state.

Another embodiment of the present disclosure discloses a surgical instrument including an end tool including a jaw, and a detection member, wherein the jaw is formed to accommodate at least one region of an operation member movable in one direction, and includes one or more wires, each of which includes at least one region disposed in the jaw, is connected to the operation member, and is formed to move together with the operation member in response to a motion of the operation member, the detection member is formed to detect motion information of the wire, and position information of the operation member is identified through the motion information detected by the detection member.

Another embodiment of the present disclosure discloses a surgical instrument including an end tool that includes a jaw including a first jaw and a second jaw facing the first jaw and a staple drive assembly including one or more staple pulleys, a reciprocating assembly disposed in at least one region of the jaw of the end tool and formed to be linearly moved by the staple drive assembly, and a detection member disposed on one region of the jaw, and configured to detect motion information of the operation member that is moved in one direction by the reciprocating assembly when the reciprocating assembly moves in the one direction by being in contact with the reciprocating assembly, wherein position information of the operation member is identified through the motion information of the operation member detected by the detection member.

In the present embodiment, the surgical instrument further may include a cartridge including at least the operation member and a plurality of staples, and formed to be accommodated in one side of the jaw, wherein as the operation member is moved in the one direction, a wedge of the operation member sequentially pushes and raises the plurality of staples in the cartridge to perform a stapling motion, and simultaneously a blade formed at one side of the wedge of the operation member is moved in the one direction to perform a cutting motion.

In the present embodiment, the detection member may be formed to detect driving information of a driving part that provides a driving force necessary for the operation member to move.

In the present embodiment, the driving force of the driving part may be transmitted to the staple drive assembly.

In the present embodiment, the driving part may include a motor member, the detection member may be formed to detect a rotation amount of the motor member, information on a rotation amount of the motor member necessary for the operation member to move an entire distance that the operation member can move from a distal end to a proximal end of the jaw may be set as reference information, and the position information of the operation member may be determined by comparing the reference information with the rotation amount of the motor member detected by the detection member.

In the present embodiment, the driving part may include a motor member, and one or more pulleys connected thereto and configured to transmit the driving force to the operation member, the detection member may detect a motion of the pulley, information on a rotation amount of the pulley necessary for the operation member to move an entire distance that the operation member can move from a distal end to a proximal end of the jaw may be set as reference information, and the position information of the operation member is determined by comparing the reference information with the rotation amount of the pulley detected by the detection member.

In the present embodiment, the detection member may be disposed inside the driving part or may be integrally formed with the driving part.

In the present embodiment, the surgical instrument may include a manipulation part configured to manipulate an operation of the end tool, wherein the driving part and the detection member may be disposed inside the manipulation part.

In the present embodiment, the detection member is formed to detect motion information of the reciprocating assembly, motion information of the reciprocating assembly necessary for the operation member to move an entire distance that the operation member can move in the jaw may be set as reference information, and the position information of the operation member may be determined by comparing the motion information detected by the detection member with the reference information.

In the present embodiment, the reciprocating assembly may be formed to alternately linearly reciprocate toward the distal end and the proximal end in a longitudinal direction of the jaw in response to rotational movement of the staple pulley of the staple drive assembly, In the present embodiment, the reference information may include information on the number of reciprocating movements of the reciprocating assembly necessary for the operation member to move an entire distance that the operation member can move from a distal end to a proximal end of the jaw, the detection member may detect motion information including the number of linear reciprocating movements of the reciprocating assembly, and the position information of the operation member may be determined by comparing the reference information with the number of reciprocating movements of the moving member detected by the detection member.

In the present embodiment, the operation member may be moved toward a distal end of the jaw together with the reciprocating assembly only when the reciprocating assembly is moved toward the distal end of the jaw.

In the present embodiment, the operation member may include a ratchet member including one or more ratchets formed in a region facing the reciprocating assembly, and the reciprocating assembly may include recesses formed to be engaged with the ratchets.

In the present embodiment, the surgical instrument may include a backward movement wire having at least one region disposed in the jaw, and connected to the operation member to move the operation member backward toward a proximal end of the jaw in a longitudinal direction, wherein the detection member may be formed to detect motion information of the backward movement wire, and the position information of the operation member may be identified through the motion information of the backward movement wire detected by the detection member.

In the present embodiment, information on an entire distance that the operation member can move in the jaw may be set as reference information, and the position information of the operation member may be determined by comparing the motion information of the backward movement wire detected by the detection member with the reference information.

In the present embodiment, the detection member may have the form of a proximity sensor, which detects the backward movement wire.

In the present embodiment, the detection member may be disposed in one region of the jaw to be adjacent to the backward movement wire.

In the present embodiment, the end tool may include an end tool shaft located on a side of a manipulation part of the surgical instrument, in a direction opposite to a direction facing the jaw, and the detection member may be disposed in an inner space of the end tool shaft at a position overlapping the backward movement wire.

In the present embodiment, the detection member may be formed to detect driving information of a driving part that provides a driving force necessary for the backward movement wire to move.

In the present embodiment, the surgical instrument may include a manipulation part configured to manipulate an operation of the end tool, wherein the driving part and the detection member may be disposed inside the manipulation part.

In the present embodiment, the operation member may be formed to move toward a distal end of the jaw together with the reciprocating assembly only when the reciprocating assembly is moved toward the distal end of the jaw, and to move backward only when pulled by the backward movement wire.

In the present embodiment, the operation member may be moved toward a distal end of the jaw by being in contact with and coupled to the reciprocating assembly, and the operation member may be spaced apart from the reciprocating assembly by the backward movement wire.

In the present embodiment, the operation member may be formed to be movable toward a proximal end of the jaw by the backward movement wire in a state in which the operation member is spaced apart from the reciprocating assembly.

In the present embodiment, whether the operation member reaches a set stop position, which is set in advance, may be determined using the position information of the operation member, and the operation member may be formed to stop its forward movement upon reaching the set stop position and remain stationary for a set waiting time, and to resume the forward movement or change into a state capable of forward movement after the set waiting time.

In the present embodiment, the set stop position may be a position corresponding to a close motion completion state of the jaw, and as the operation member moves after the set waiting time, a stapling process may proceed to a firing state.

An embodiment of the present disclosure discloses a surgical instrument including a manipulation part configured to control an operation of the end tool, and a connection part configured to connect the manipulation part to the end tool.

In the present embodiment, the end tool may be formed to be yaw-rotatable around one shaft and pitch-rotatable around another shaft different from the one shaft.

An embodiment of the present disclosure discloses a method of driving any one of the surgical instruments, the method including a surgical procedure including one or more steps using the surgical instrument, wherein a position of the operation member is determined through the detection member before performing one step.

In the present embodiment, in the surgical procedure including one or more steps using the surgical instrument, the steps may include, through the determination of the position of the operation member, a step of determining whether the operation member reaches a set stop position, which is a position set in advance, when the operation member moves forward, a step of controlling the operation member to stop its forward movement for a set waiting time, which is set in advance, when it is determined that the operation member has reached the set stop position, and a step of changing a state of the operation member to a state in which a command of a forward movement or a forward movement is inputtable when the set waiting time has passed.

Other aspects, features, and advantages other than those described above will become apparent from the following drawings, claims, and detailed description of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
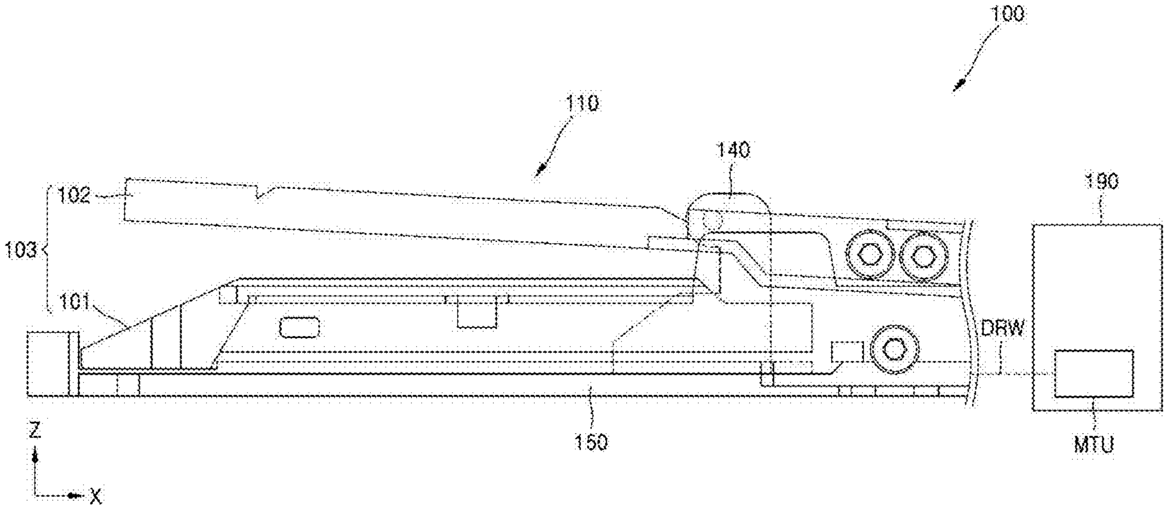
FIG. 1 is a schematic view of a surgical instrument according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term “and/or” includes any and all combinations of one or more of the associated listed items. Expressions such as “at least one of,” when preceding a list of elements, modify the entire list of elements and do not modify the individual elements of the list.

While the present disclosure is susceptible to various modifications and alternative forms, specific embodiments thereof are shown by way of example in the drawings and will herein be described in detail. Advantages and features of the present disclosure and methods for accomplishing the same will be more clearly understood from embodiments described below with reference to the drawings. However, the present disclosure is not limited to the embodiments disclosed below but may be implemented in various forms.

Hereinafter, the embodiments of the present disclosure will be described in detail with reference to the accompanying drawings, but when describing with reference to the drawings, equal or corresponding components will be referred to as the same reference numerals, and redundant descriptions thereof will be omitted.

In the following embodiments, the terms “first,” “second,” and the like have been used to distinguish one component from another, rather than limitative in all aspects.

In the following embodiments, singular forms are intended to include plural forms as well, unless the context clearly indicates otherwise.

In the following embodiments, terms such as “include” or “have” means that the features or components described in the specification are present, and the possibility that one or more other features or components will be added is not excluded in advance.

Sizes of components in the drawings may be exaggerated or reduced for convenience of description. For example, the size and thickness of each component shown in the drawings are arbitrarily represented for convenience of description, and thus, the present disclosure is not necessarily limited thereto.

In the following embodiments, an x-axis, a y-axis, and a z-axis are not limited to three axes of the rectangular coordinate system, and may be interpreted in a broader sense. For example, the x-axis, the y-axis, and the z-axis may be perpendicular to one another, or may represent different directions that are not perpendicular to one another.

In cases where certain embodiments may be implemented otherwise, a specific process sequence may be performed differently from the described sequence. For example, two consecutively described processes may be performed substantially at the same time or performed in an order opposite to the described order.

FIG. 1 is a schematic view of a surgical instrument according to an embodiment of the present disclosure.

Figure 2:
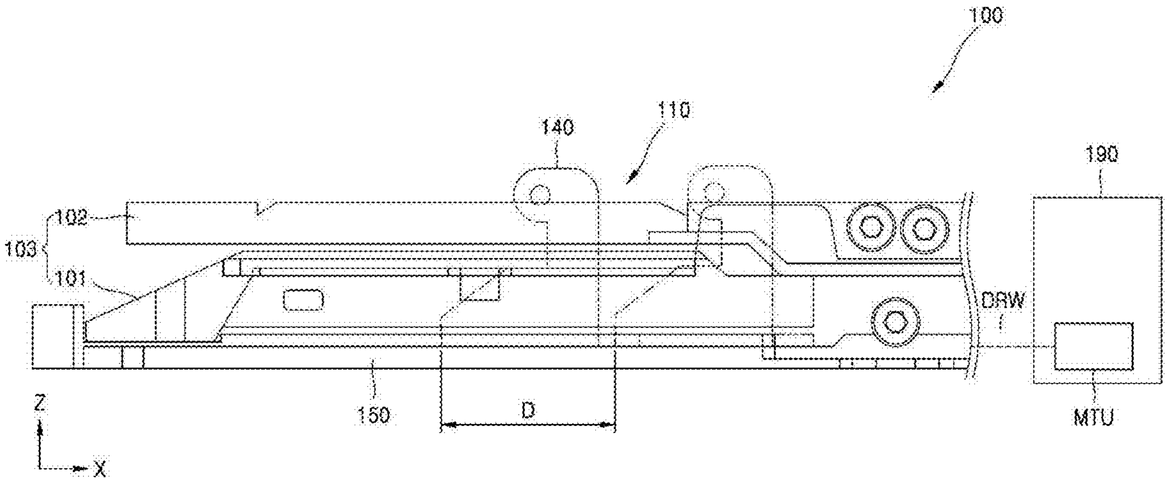
FIG. 2 is a view for describing a motion of an operation member of FIG. 1.

FIG. 2 is a view for describing a motion of an operation member of FIG. 1.

Figure 3:
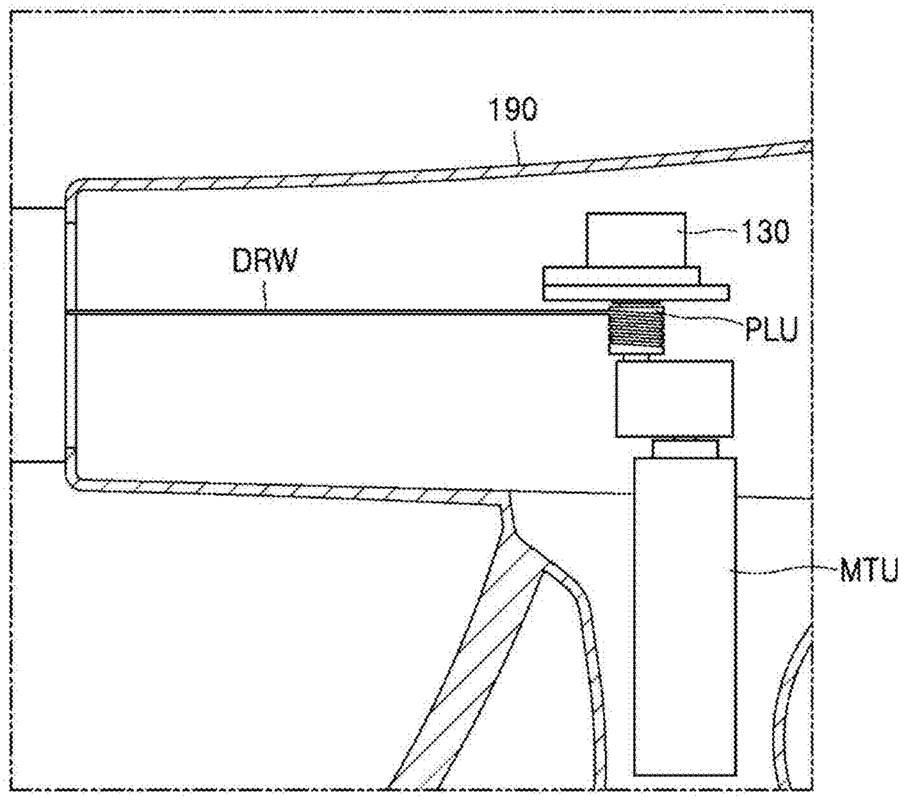
FIG. 3 is a view for describing a detection member of FIGS. 1 and 2.

FIG. 3 is a view for describing a detection member of FIGS. 1 and 2.

Referring to FIGS. 1 to 3, a surgical instrument 100 of the present embodiment may include an end tool 110. The end tool 110 may be manipulated through a manipulation part 190.

For example, the end tool 110 is disposed in one region of the surgical instrument 100, such as an end portion thereof, and may be inserted into a surgical site to perform a motion necessary for surgery. In addition, as an example, the end tool 110 may be connected to the manipulation part 190 through one or more connection parts and driven through manipulation of the manipulation part.

The end tool 110 may include a jaw 103.

The jaw 103 may be formed to accommodate an operation member 140 in at least one region thereof. For example, the jaw 103 may be formed to have a space similar to a hollow box such that the operation member 140 is accommodated in the space, and the operation member 140 may move in one direction while being accommodated in the jaw 103.

The jaw 103 may have various forms, such as being configured as one or more jaws, as a specific example, two jaws. For example, the jaw 103 may include a first jaw 101 and a second jaw 102.

The first jaw 101 and the second jaw 102 may be disposed to face each other, thereby allowing a grip motion to be performed. As a specific example, the first jaw 101 and the second jaw 102 may perform a grip motion while moving and rotating around a rotation shaft (not shown).

The first jaw 101 may have a shape elongated to have a length greater than a width, and may have, for example, an elongated bar shape. The first jaw 101 may be formed to accommodate the operation member 140. For example, the first jaw 101 may have a shape similar to a hollow box, with one surface (e.g., a surface facing the second jaw) open, and may be formed to accommodate at least one region of the operation member 140 therein. The operation member 140 may move in one direction while being accommodated in the first jaw 101.

The second jaw 102 may have a shape elongated to have a length greater than a width, and may have, for example, an elongated bar shape.

The first jaw 101 may have a space in which at least one staple (not shown) may be disposed, or may be formed such that the staple (not shown) is disposed in an interior that is similar to the hollow box described above.

In an optional embodiment, an anvil may be formed on one surface of the second jaw 102 to face the staple.

Through the movement of the operation member 140 disposed in the first jaw 101, the end tool 110 of the surgical instrument 100 may initiate one or more motions. For example, stapling may be performed by moving the operation member 140 such that the staple (not shown) accommodated in the first jaw 101 is withdrawn to face the second jaw 102.

For example, the operation member 140 may move forward (move toward a distal end) from the state shown in FIG. 1, and may move from the state shown in FIG. 1 to the state shown in FIG. 2. Specifically, the operation member 140 may move forward by a distance D. When the operation member 140 changes in position through such forward-moving, the change may be detected by a detection member 130 (in FIG. 3). This will be described in more detail.

The operation member 140 may receive a driving force through a moving member 150. For example, the moving member 150 may be formed to move in one direction or both directions. As a specific example, the moving member 150 may be formed to reciprocate either in the same direction as the forward movement of the operation member 140, or in the opposite direction.

At least one region of the moving member 150 may be disposed in one region of the end tool 110, such as an inner side of the first jaw 101.

The moving member 150 may be formed to transmit a driving force to the operation member 140, for example, by coming into contact with the operation member 140. As a specific example, the moving member 150 may have the form of a rack having one or more recesses, and the operation member 140 may include ratchets, which correspond to the recesses and are mutually engaged with the recesses, so that a driving force is transmitted to the operation member 140 through movement of the moving member 150.

In addition, the moving member 150 may transmit a driving force to the operation member 140 in various other methods, and for example, the moving member 150 may have the form of a clutch without recesses.

The moving member 150 may move by various power sources, such as a driving part MTU. The driving part MTU may include a motor member as a power source.

The driving part MTU may be disposed in one region of the manipulation part 190. In addition, in another optional embodiment, the driving part MTU may be disposed in another region of the surgical instrument 100, e.g., in one region of the end tool 110, one region of a connection part (not shown) connecting the end tool 110 to the manipulation part 190, or one region outside the surgical instrument 100.

The driving part MTU may be connected to the moving member 150 by one or more power transmission parts DRW, and a driving force of the driving part MTU, e.g., a rotating force, may be transmitted to the moving member 150 through the power transmission parts DRW. As a specific example, the power transmission part DRW may include one or more wires.

The rotating force of the driving part MTU may be transmitted to the moving member 150 through the power transmission part DRW including one or more wires, and in an optional embodiment, the driving part MTU may be connected to the power transmission part DRW through one or more pulleys PLU.

When the driving part MTU moves, for example, when the motor member rotates, a driving force determined according to one rotation of the motor member is transmitted to the moving member 150 through the power transmission part DRW, and the moving member 150 performs a predetermined range of motion (e.g., moves forward or backward when the moving member 150 has the form of a rack), and the degree of forward movement, such as a distance moved by the operation member 140 may be determined accordingly.

The detection member 130 may detect motion information of the driving part MTU, e.g., a rotation amount of the motor member when the motor member of the driving part MTU rotates. As a specific example, the detection member 130 may include an encoder configured to detect the number of rotations or rotation amount of the motor member.

The detection member 130 may be of various forms or types that perform the above functions.

The detection member 130 may be disposed at a position adjacent to or spaced apart from the driving part MTU, such as above the pulley PLU, which is rotated by the driving part MTU, as illustrated in FIG. 3. However, this is one example, and the detection member 130 may be disposed inside the manipulation part 190 to be adjacent to the driving part MTU.

The motion information of the driving part MTU, such as the rotation amount or the number of rotations of the motor member, may be measured through the detection member 130, and based on this motion information, related information regarding the movement of the moving member 150 and a moving distance of the operation member 140 resulting therefrom may be determined as described above. Consequently, position information of the operation member 140 may be detected and provided to a user.

As an example, when the driving part MTU includes a motor member, the number of rotations or steps corresponding to the moving distance of the operation member 140 may be set. For example, reference information regarding the number of rotations or steps necessary for the operation member 140 to move the entire section that the operation member 140 can move in the jaw 103 may be preset and stored. As a specific example, reference information regarding the maximum distance the operation member 140 moves from a proximal end to the distal end of the jaw 103 while being accommodated in the first jaw 101 may be preset and stored, and a current position of the operation member 140 may be determined by comparing the currently determined number of rotations of the driving part MTU and the reference information. As a specific example, if the detected number of rotations of the driving part MTU when the reference information is 10 (i.e., when the total necessary number of rotations is 10) is 2, then the operation member 140 may be considered to be in a position that has advanced 20 percent of the entire section.

The reference information and determinations obtained through the driving part MTU may optionally be applied to the remaining parts of the specification to be described later.

Figure 4:
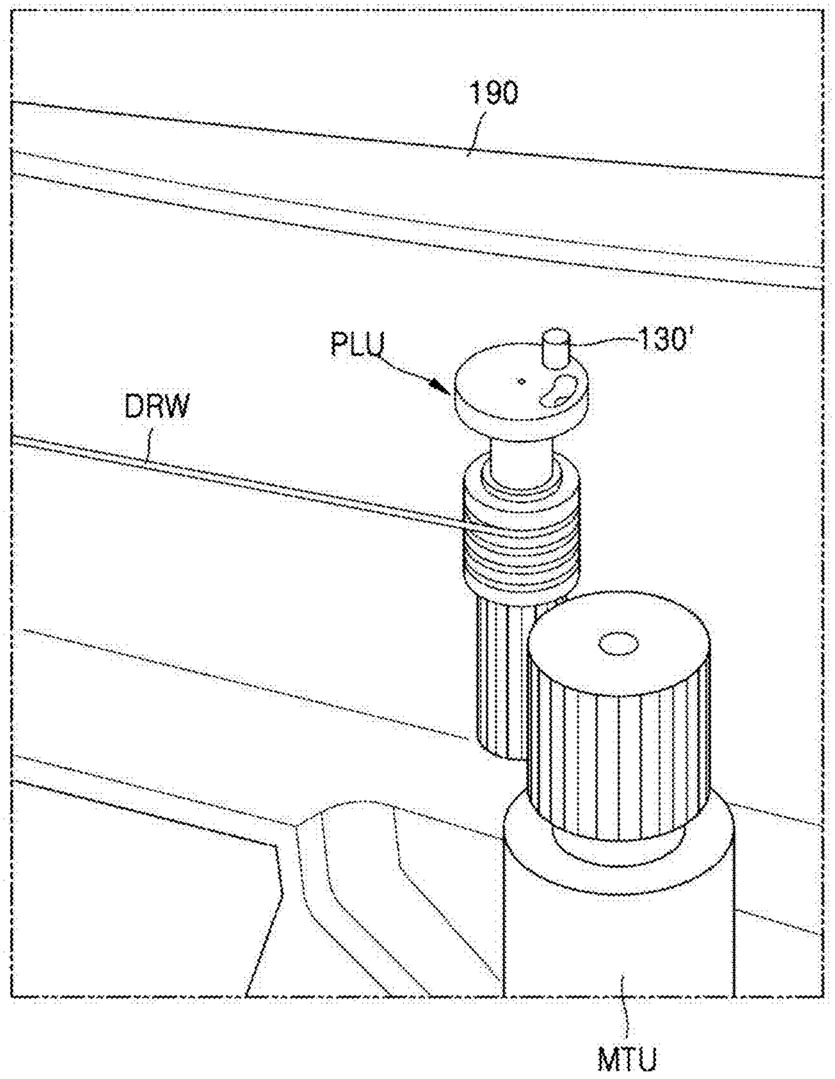
FIG. 4 is a view for describing one modified example of the detection member of FIG. 3.

FIG. 4 is a view for describing one modified example of the detection member of FIG. 3.

Referring to FIG. 4, a detection member 130' may be disposed in one region of the pulley PLU to detect a motion of the pulley PLU, for example, the detection member 130' may be a proximity sensor and may detect a rotational motion of the pulley PLU when the pulley PLU rotates.

Figure 5:
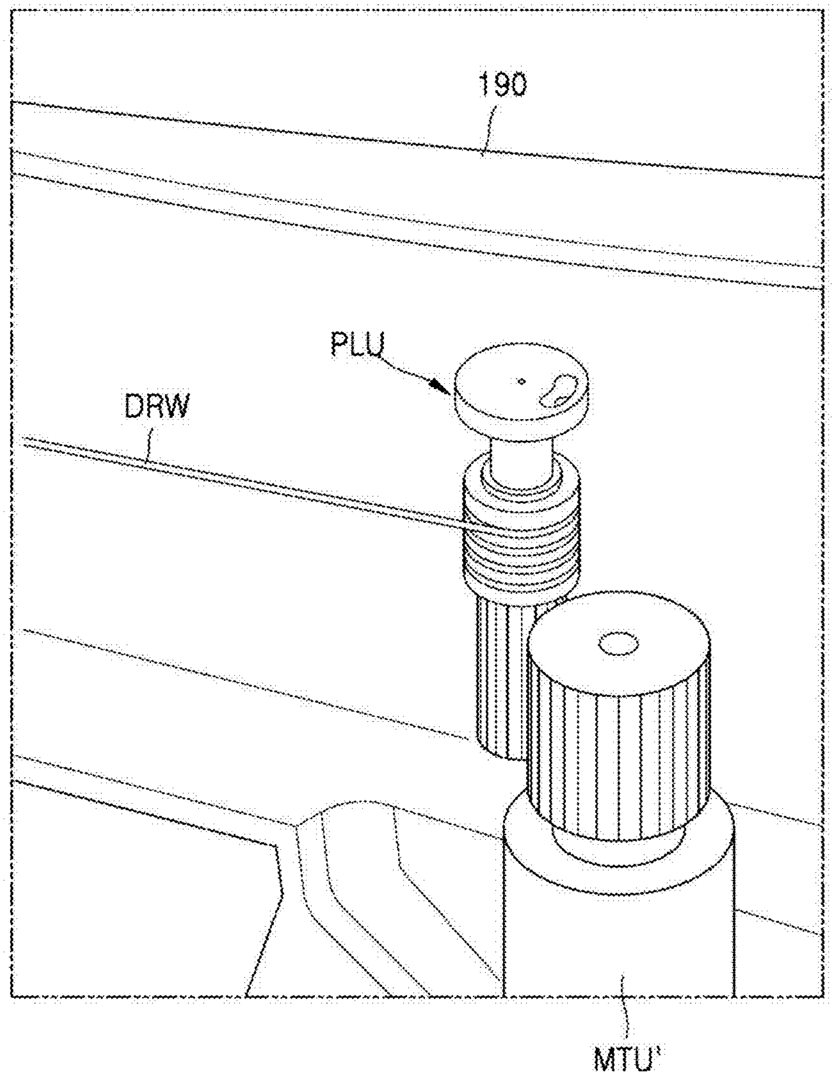
FIG. 5 is a view for describing another modified example of the detection member of FIG. 3.

FIG. 5 is a view for describing another modified example of the detection member of FIG. 3.

Referring to FIG. 5, a driving part MTU' may include a detection member. For example, the driving part MTU' may have a sensor-embedded or sensor-integrated structure, and may include a Hall sensor or other various types of sensors (as a specific example a position sensor), and when a motor member of the driving part MTU' rotationally moves, the rotationally movement may be detected and the number of rotations or a rotation amount of the motor member may be measured.

By measuring the motion information of the driving part MTU or MTU' through the detection members 130 or 130' or the driving part MTU' as described above, determining motion information of the moving member 150 connected to the driving part MTU or MTU', and finally, determining motion and position information of the operation member 140, it is possible to precisely determine a status of each of steps in the process of performing an operation using the end tool 110 and precisely control initiation of each step's progression.

For example, the operation member 140 may move forward, e.g., toward the distal end to safely and efficiently perform a process using the end tool 110, specifically, a stapling motion. As a result, each of steps of the stapling process can be precisely controlled. For example, the initiation of each step can be appropriately controlled, and as a specific example, when the operation member 140 moves toward the distal end while positioned adjacent to the proximal end, this movement can be precisely detected, and the process of determining whether to proceed with the next step or wait can be precisely controlled. As a specific example, when stapling is performed using the jaw 103, the condition of the tissue being stapled can be precisely controlled after blood has been drained from the tissue. Subsequently, the operation member 140 can move safely to proceed through each step safely and efficiently to complete the stapling.

As a specific example, the operation member 140 may reach a "set stop position," when moving forward, such as a position at which the forward movement is paused, and this set stop position, which is set in advance, may be a position at which the jaw 103 has completed a close motion. Through the detection members of the embodiment and modified examples described above, it is possible to accurately determine whether the operation member 140 is in the set stop position.

Afterward, the operation member 140 stops moving and remains in the "set stop position" for a "set waiting time (e.g., about 15 seconds), which is a time period set in advance. For example, during the set waiting time, blood may be drained from the tissue being stapled.

After the set waiting time elapses, the operation member 140 may resume movement, i.e., may move forward to perform a subsequent step (such as entering a firing state in the stapling process). Alternatively, the state may be changed to a state in which a command for forward movement can be input (e.g., ready to fire or start fire the staple).

Figure 6:
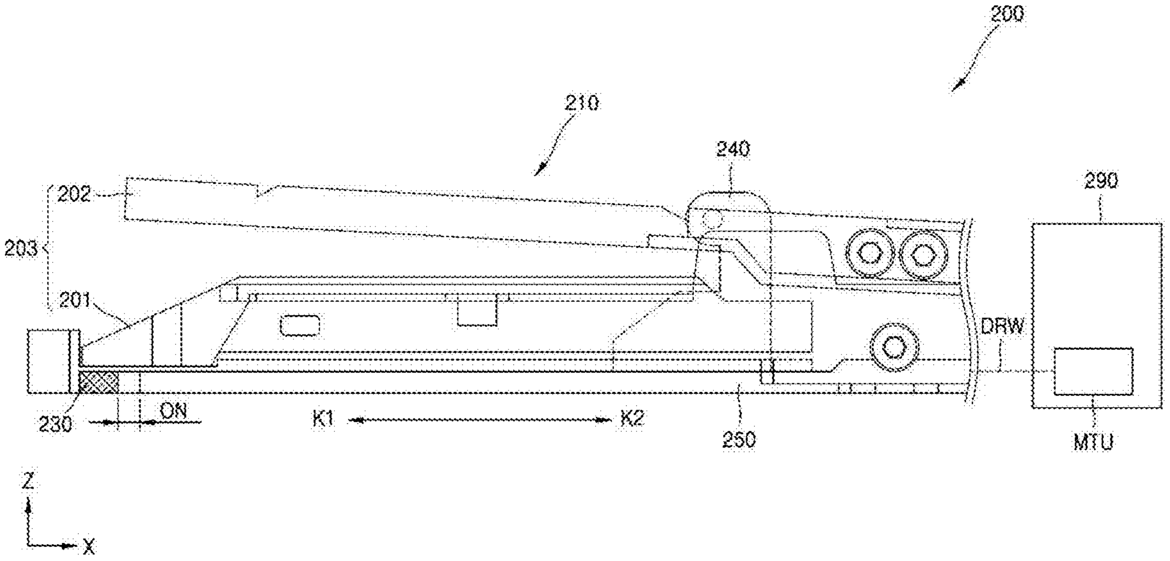
FIG. 6 is a schematic view of a surgical instrument according to another embodiment of the present disclosure.

FIG. 6 is a schematic view of a surgical instrument according to another embodiment of the present disclosure.

Figure 7:
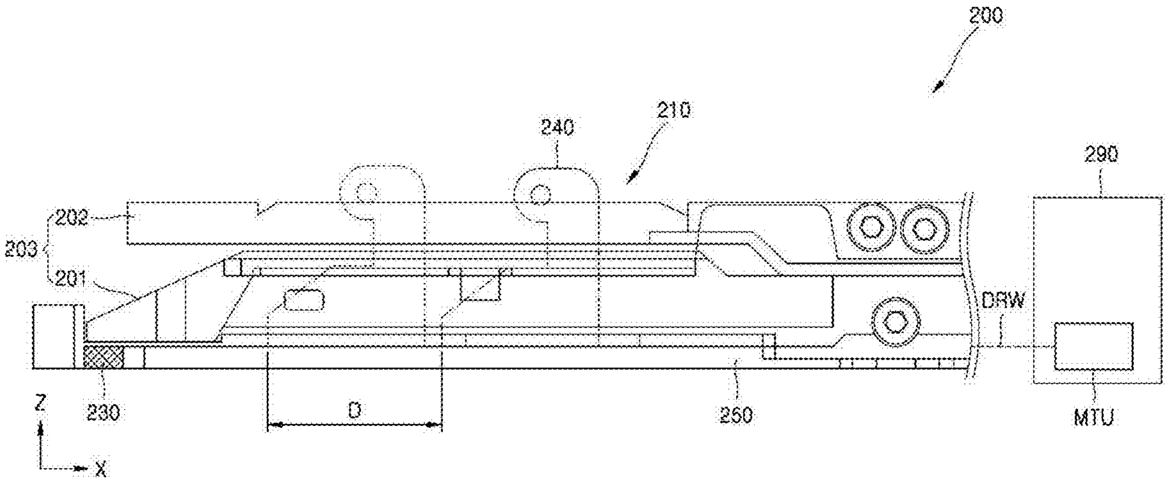
FIG. 7 is a view for describing a motion of an operation member of FIG. 6.

FIG. 7 is a view for describing a motion of an operation member of FIG. 6.

Referring to FIGS. 6 to 7, a surgical instrument 200 of the present embodiment may include an end tool 210.

For convenience of description, differences from the above-described embodiment will be mainly described.

The end tool 210 may include a jaw 203.

The jaw 203 may be formed to accommodate an operation member 240 in at least one region thereof. The jaw 203 may have various forms, such as being configured as one or more jaws, as a specific example, two jaws. For example, the jaw 203 may include a first jaw 201 and a second jaw 202.

For example, the operation member 240 may move forward (move toward a distal end) from the state shown in FIG. 6, and may move from the state shown in FIG. 6 to the state shown in FIG. 7. Specifically, the operation member 240 may move forward by a distance D.

When the operation member 240 changes in position through such forward-moving, the change may be detected by a detection member 230. This will be described in more detail.

The operation member 240 may receive a driving force through a moving member 250. For example, the moving member 250 may be formed to move in one direction or both directions. As a specific example, the moving member 250 may be formed to reciprocate either in the same direction as the forward movement of the operation member 240, or in the opposite direction.

At least one region of the moving member 250 may be disposed in one region of the end tool 210, such as an inner side of the first jaw 201.

The moving member 250 may be formed to transmit a driving force to the operation member 240, for example, by coming into contact with the operation member 240. As a specific example, the moving member 250 may have the form of a rack having one or more recesses, and the operation member 240 may include ratchets, which correspond to the recesses and are mutually engaged with the recesses, so that a driving force is transmitted to the operation member 240 through movement of the moving member 250.

In addition, the moving member 250 may transmit a driving force to the operation member 240 in various other methods, and for example, the moving member 250 may have the form of a clutch without recesses.

The moving member 250 may move by various power sources, such as a driving part (not shown), and the driving part (not shown) and the moving member 250 may be connected to a power transmission part, including one or more wires.

The detection member 230 may detect motion information of the moving member 250. For example, the detection member 230 may have the form of a proximity sensor that detects the motion or position of the moving member 250. The detection member 230 may have an optically sensing form, or in other cases, may be formed as a contact-type sensor.

As an example, the detection member 230 may be disposed in one region (e.g., one region of the distal end) of the first jaw 201 at a position that is spaced apart from the moving member 250 to be close thereto. The detection member 230 may detect motion information of the moving member 250, such as forward movement or backward movement, and may determine the degree or number of times the moving member 250 moves forward or backward during a set time period. Accordingly, a moving distance of the moving member 250 and a moving distance of the operation member 240 according thereto may be determined. As a result, position information of the operation member 240 may be detected and provided to a user.

As an example, when the operation member 240 is moved using the moving member 250, the number of reciprocations of the moving member 250 necessary for the distance the operation member 240 has to move may be set. For example, reference information regarding the number of reciprocations necessary for the operation member 240 to move the entire section that the operation member 240 can move in the jaw 203 may be preset and stored. As a specific example, reference information regarding the maximum distance that the operation member 240 moves from a proximal end to the distal end of the jaw 203 while being accommodated in the first jaw 201 may be preset and stored, and a current position of the operation member 240 may be determined by comparing the currently determined number of reciprocations of the moving member 250 and the reference information. As a specific example, if the detected number of reciprocation of the moving member 250 when the reference information i.e., the total necessary number of reciprocations, is 10, is 3, then the operation member 240 may be considered to be in a position that has advanced 30 percent of the entire section.

The reference information and determinations obtained through the moving member 250 may optionally be applied to the remaining parts of the specification to be described later.

Figure 8:
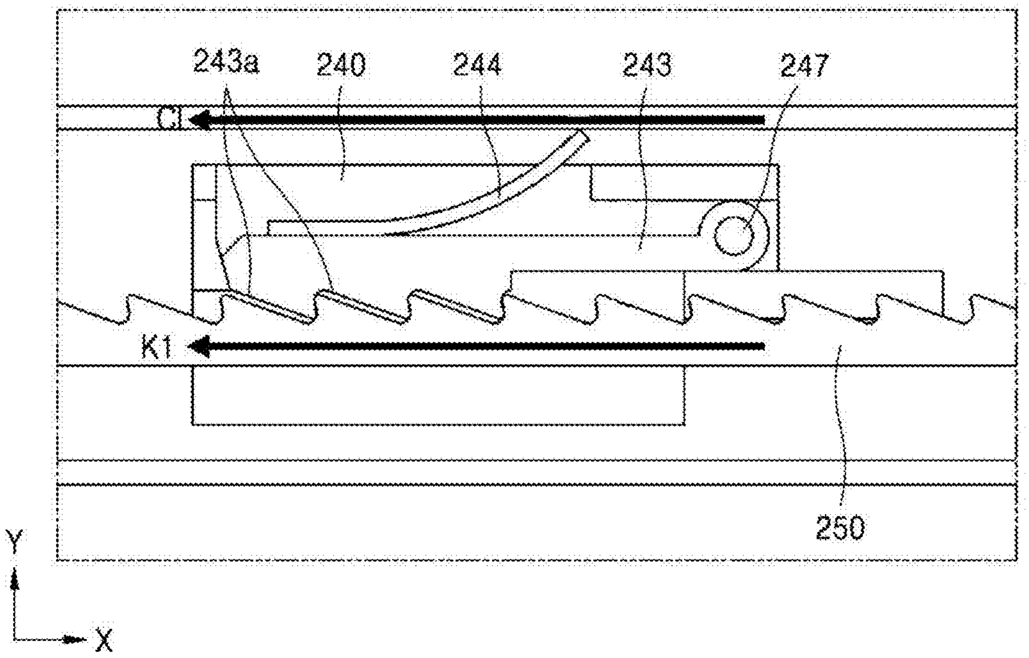
FIGS. 8 and 9 are views for describing the operation member and a moving member according to an embodiment of the present disclosure.
Figure 9:
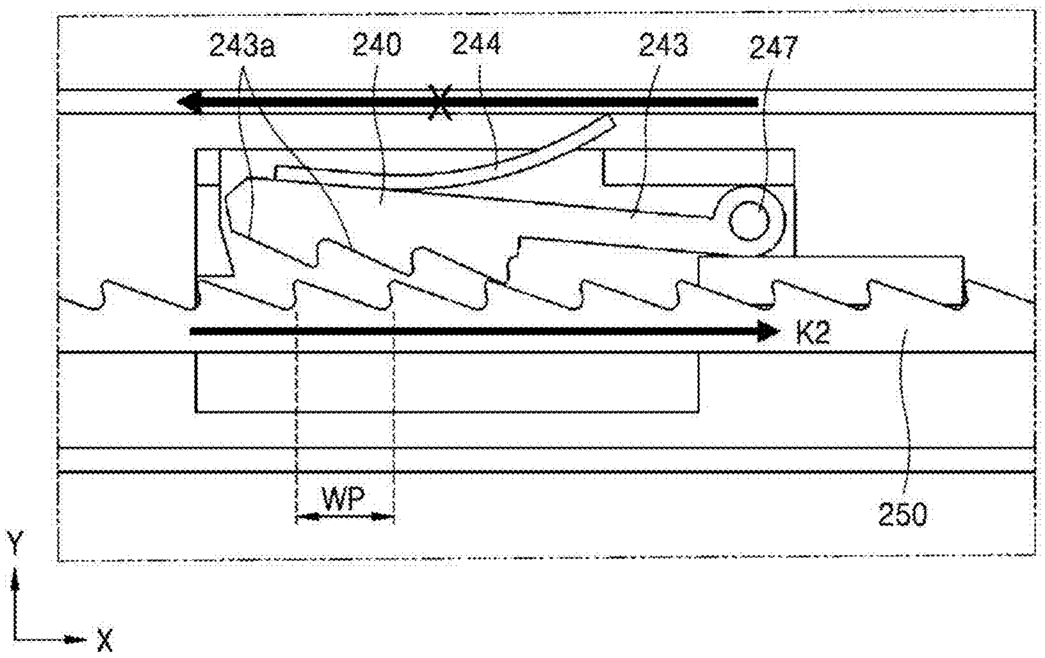

FIGS. 8 and 9 are views for describing the operation member and the moving member according to an embodiment of the present disclosure.

Referring to FIGS. 8 and 9, the moving member 250 may have the form of a rack, and may include a plurality of recesses.

The operation member 240 may include a ratchet member 243 having ratchets 243*a* each engaged with a sawtooth-shaped recess of the moving member 250, in one region. In an optional embodiment, the ratchet member 243 may rotationally move around a ratchet rotating shaft 247 when a force is applied, and an elastic member 244 may be disposed to apply a force to the operation member 240 toward the moving member 250.

The moving member 250 may move by the driving part (not shown), for example, may alternately move (forward) toward the distal end (K1 direction) as illustrated in FIG. 8 and move (backward) toward the proximal end (K2 direction) as illustrated in FIG. 9. The moving member 250 may be formed to perform these forward and backward reciprocating movements continuously.

Such movements may be implemented by transmitting the motion of one or more pulleys and one or more link members connected thereto to the moving member 250, and may also be implemented by including various mechanical configurations.

When the moving member 250 moves forward (in the K1 direction) as shown in FIG. 8, a force is transmitted to the ratchet member 243 coupled to the recesses of the moving member 250 to cause the operation member 240 to also move forward (a C1 direction). In contrast, when the moving member 250 moves backward (in the K2 direction) as shown in FIG. 9, the ratchets 243*a* of the ratchet member 243, which are engaged with the recesses of the moving member 250, are disengaged from the recesses of the moving member 250 as the recesses of the moving member 250 slide over inclined surfaces of the ratchets 243*a*, the coupling between the operation member 240 and the moving member 250 is released, and thus the operation member 240 does not move. That is, the operation member 240 is in a stationary state when the moving member 250 moves backward (in the K2 direction).

At this time, the moving member 250 may be allowed to move forward by one pitch interval WP of the recesses, which can be achieved by setting a movement value in the driving part (not shown) that causes the moving member 250 to move. For example, the moving member 250 may be allowed to move forward by one pitch interval WP when the motor member (refer to the embodiment described above) performs one rotation, and move backward by one pitch interval WP when the motor member performs the next rotation.

In this case, when the moving member 250 performs one reciprocating movement, i.e., moves forward by one pitch interval WP and moves backward by one pitch interval WP, the operation member 240 remains stationary after moving forward by one pitch interval WP.

As a result, when the detection member 230 detects motion information, such as forward and backward movements of the moving member 250, and specifically detects one forward movement followed by one backward movement of the moving member 250, along with determining the number of such reciprocating movements, the motion information, including forward movement of the operation member 240, and the resultant position information of the operation member 240 may be determined.

By detecting the motion information of the moving member 250 through the detection member 230 as described above, for example, by determining the forward and backward movement information, motion and position information of the operation member 240 can be finally determined. Through this, it is possible to precisely determine a status of each of steps in the process of performing an operation using the end tool 210 and precisely control initiation of each step's progression.

For example, the operation member 240 may move forward, e.g., toward the distal end to safely and efficiently perform a process using the end tool 210, specifically, a stapling motion. As a result, each of steps of the stapling process can be precisely controlled.

Figure 10A:
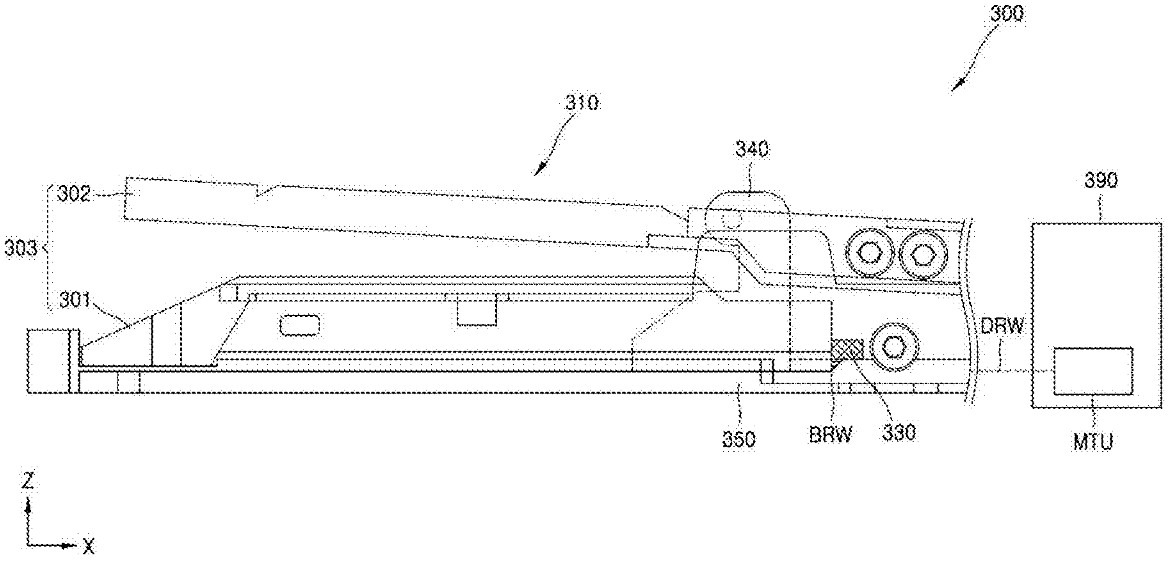
FIG. 10A is a schematic view of a surgical instrument according to another embodiment of the present disclosure.
Figure 10B:
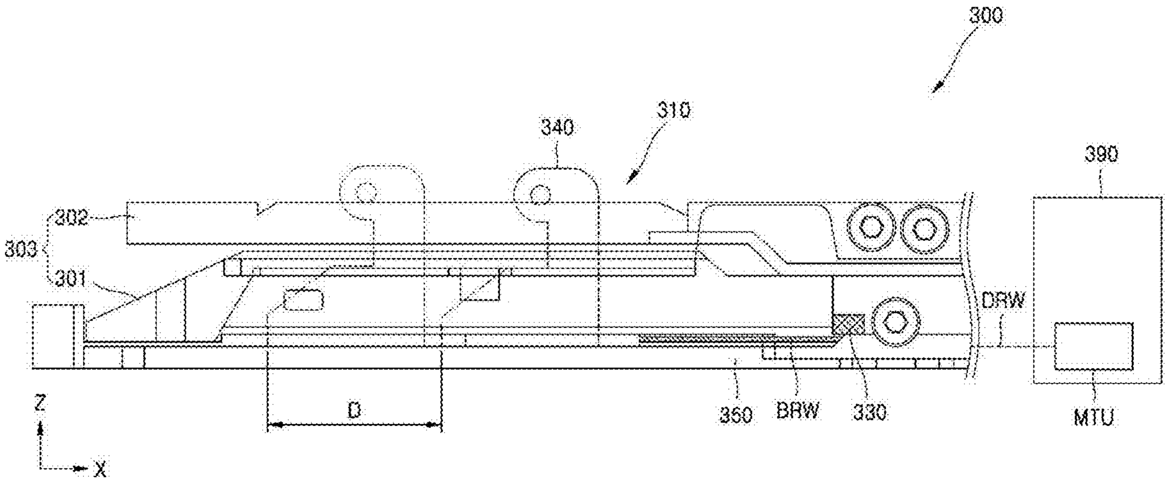
FIG. 10B is a view for describing a motion of an operation member of FIG. 10A.

FIG. 10A is a schematic view of a surgical instrument according to another embodiment of the present disclosure. FIG. 10B is a view for describing a motion of an operation member of FIG. 10A.

Referring to FIGS. 10A and 10B, a surgical instrument 300 of the present embodiment may include an end tool 310.

For convenience of description, differences from the above-described embodiment will be mainly described.

The end tool 310 may include a jaw 303.

The jaw 303 may be formed to accommodate an operation member 340 in at least one region thereof. The jaw 303 may have various forms, such as being configured as one or more jaws, as a specific example, two jaws. For example, the jaw 303 may include a first jaw 301 and a second jaw 302.

For example, the operation member 340 may move forward (move toward a distal end) from the state shown in FIG. 10A, and may move from the state shown in FIG. 10A to the state shown in FIG. 10B. Specifically, the operation member 340 may move forward by a distance D.

The operation member 340 may move backward after the forward movement. Meanwhile, when the operation member 340 moves forward, a backward movement wire BRW connected to the operation member 340 does not transmit a driving force for the backward movement of the operation member 340 to the operation member 340. In other word, the operation member 340 is not pulled toward a proximal end of the jaw 303 through the backward movement wire BRW.

During the forward movement of the operation member 340, the backward movement wire BRW is attracted to the operation member 340 and moves forward. For example, since the backward movement wire BRW is connected to the operation member 340, the backward movement wire BRW is moved together with the operation member 340 during the forward movement of the operation member 340. At this time, information on the movement of the backward movement wire BRW may be detected through a detection member 330, and a position of the operation member 340 may be determined by using displacement resulting from the movement of the backward movement wire BRW.

Of course, even when there is a change in position of the backward movement wire BRW through the backward movement of the backward movement wire BRW, the backward movement wire BRW may be detected through the detection member 330, and the position of the operation member 340 may be determined. This will be described in more detail.

The operation member 340 may receive a driving force enabling at least forward movement, i.e., movement toward a distal end (in the left direction in FIGS. 10A and 10B). For example, the operation member 340 may receive a driving force through a moving member 350, which is formed to be disposed in at least one region of the jaw 303.

In an optional embodiment, the moving member 350 may be formed to move in one direction or both directions, and as a specific example, the moving member 350 may be formed to reciprocate in the same direction as the forward movement of the operation member 340 and in the opposite direction. More specifically, the moving member 350 may be formed to alternate between forward and backward movements sequentially. In addition, as the moving member 350, the moving member 250 of the above-described embodiment may be applied as it is.

The moving member 350 may move by various power sources, such as a driving part MTU, and the driving part MTU and the moving member 350 may be connected to a power transmission part, including one or more wires.

The backward movement wire BRW may be connected to one region of the operation member 340. The backward movement of the operation member 340 may be performed through the backward movement wire BRW. For example, the backward movement wire BRW may receive a force to move the operation member 340 toward the proximal end of the jaw 303 (in the right direction in FIGS. 10A and 10B), and in other words, the backward movement wire BRW may be formed to pull the operation member 340.

The driving part MTU capable of pulling the backward movement wire BRW may be connected to the backward movement wire BRW, and the backward movement wire BRW may be operated according to manual or automatic manipulation.

By pulling the backward movement wire BRW, the operation member 340 may move backward.

In an optional embodiment, the operation member 340 may move forward by the moving member 350 as described above, and when the moving member 350 moves backward, the operation member 340 may remain stationary (see FIGS. 8 and 9 of the above-described embodiment).

At this time, the backward movement wire BRW may be used to move the operation member 340 backward to the desired extent.

The detection member 330 may detect motion information of the backward movement wire BRW. For example, the detection member 330 may have the form of a proximity sensor, which detects the motion or position of the backward movement wire BRW. The detection member 330 may have an optically sensing form, or in other cases, may be formed as a contact-type sensor.

As an example, the detection member 330 may be disposed in one region (e.g., one region of the proximal end) of the first jaw 301 at a position that is spaced apart from the backward movement wire BRW to be close thereto. Motion information of the backward movement wire BRW, such as whether the backward movement wire BRW has moved and a distance the backward movement wire BRW has moved, can be detected through the detection member 330, and accordingly, a distance the operation member 340 has moved backward can be determined through the backward movement wire BRW. As a result, position information of the operation member 340 may be detected and provided to a user.

In addition, as a specific example, a force pulling the backward movement wire BRW is not transmitted to the backward movement wire BRW connected to the operation member 340 during the forward movement of the operation member 340, and the backward movement wire BRW is attracted to the operation member 340 while being connected thereto and moves forward together therewith. Thus, the position of the operation member 340 may be easily determined by detecting the position of the backward movement wire BRW.

As an example, when the backward movement wire BRW is connected to the operation member 340 and moved together therewith, motion information of the backward movement wire BRW corresponding to the position of the operation member 340 may be set.

Reference information regarding the entire section that the operation member 340 can move in the jaw 303 may be preset and stored. As a specific example, reference information regarding the entire distance that the operation member 340 can move from the proximal end to the distal end of the jaw 303 while being accommodated in the first jaw 301 may be preset and stored, and a current position of the operation member 340 may be determined by comparing the currently determined movement position (displacement) of the backward movement wire BRW and the reference information. As a specific example, if the detected movement position (displacement) of the backward movement wire BRW when the reference information, i.e., the entire distance is 10, is 3, then the operation member 340 may be considered to be in a position that has advanced 30 percent of the entire section.

The description of determining the position of the operation member by comparing the position (displacement) of the backward movement wire BRW with the reference information through such a backward movement wire BRW is optionally applicable to the remaining part of the specification to be described later.

As described above, motion information of the backward movement wire BRW may be detected through the detection member 330, and motion and position information of the operation member 340 may be determined through the detected motion information. Through this, it is possible to precisely determine a status of each of steps in the process of performing an operation using the end tool 310 and precisely control initiation of each step's progression.

For example, a stapling process through the motion of the operation member 340 can be safely and efficiently performed. As a result, each of steps of the stapling process can be precisely controlled.

Figure 11A:
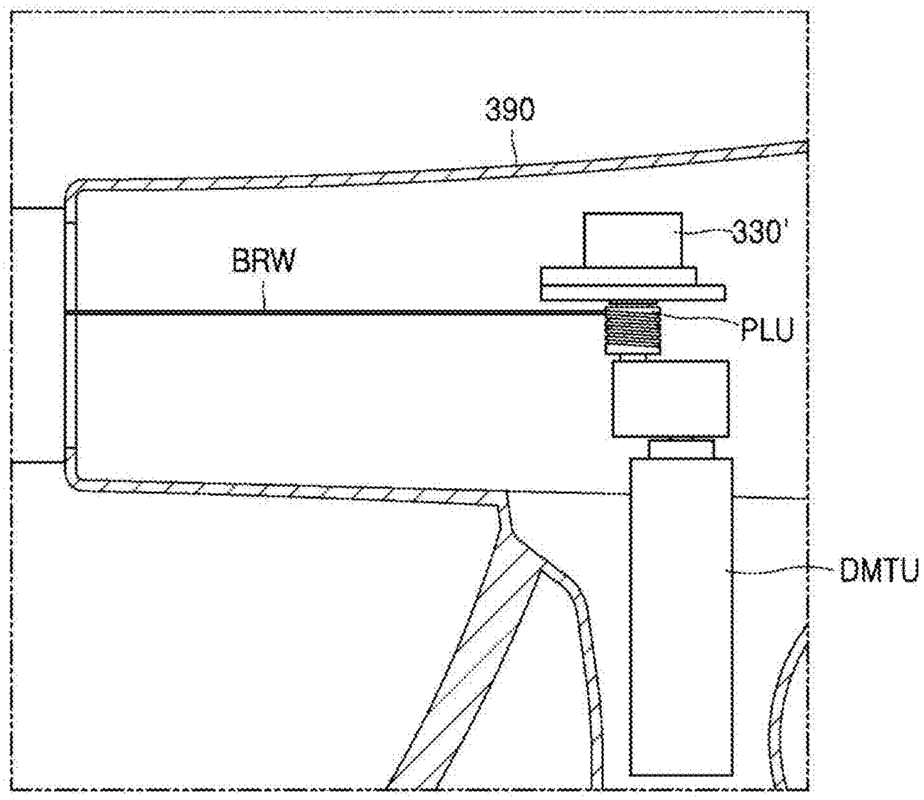
FIGS. 11A to 11C are views for describing modified examples of a detection member of FIGS. 10A and 10B.
Figure 11B:
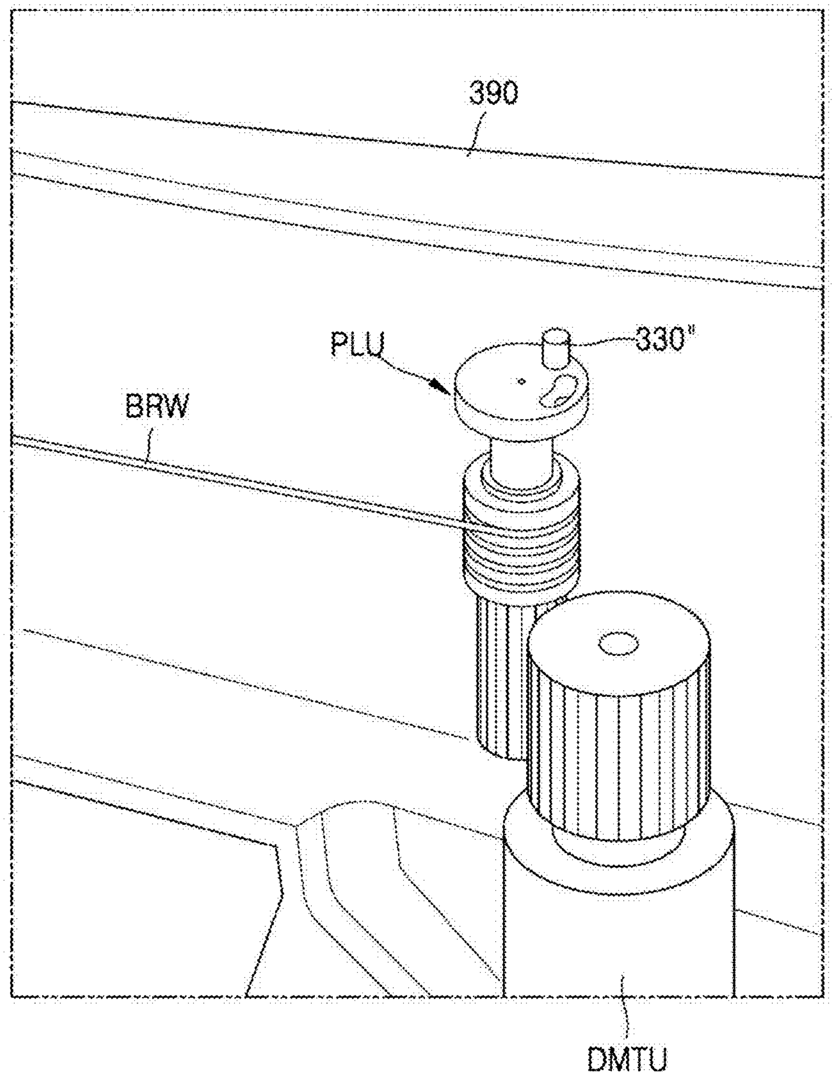
Figure 11C:
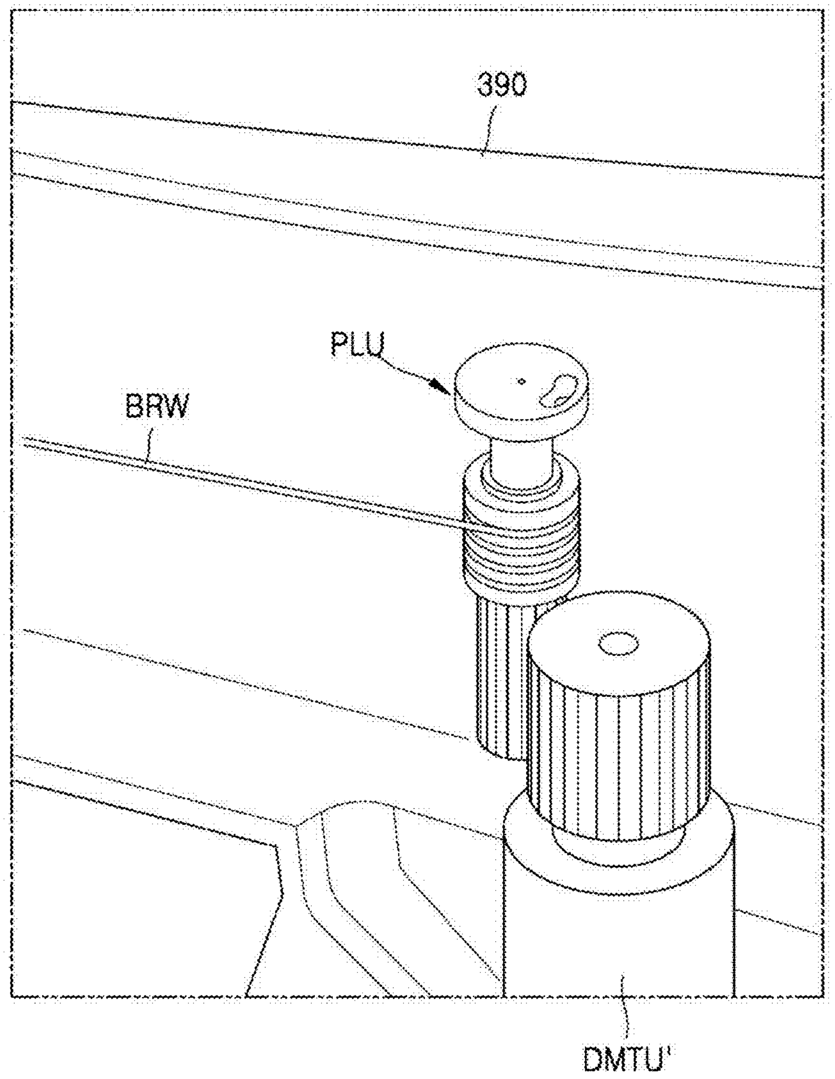

FIGS. 11A to 11C are views for describing modified examples of the detection member of FIGS. 10A and 10B.

The backward movement wire BRW may move by various power sources, such as a backward movement driving part DMTU. The backward movement driving part DMTU may include a motor member as a power source.

The backward movement driving part DMTU may be disposed in one region of a manipulation part 390. In addition, in another optional embodiment, the driving part DMTU may be disposed in another region of the surgical instrument 300, e.g., in one region of the end tool 310, one region of a connection part (not shown) connecting the end tool 310 to the manipulation part 390, or one region outside the surgical instrument 300.

A rotational force of the backward movement driving part DMTU may be transmitted to the backward movement wire BRW, and in an optional embodiment, the backward movement driving part DMTU may be connected to the backward movement wire BRW through one or more pulleys PLU.

During the movement of the backward movement driving part DMTU, such as rotation of the motor member, a driving force, which is determined by a single rotation, may be transmitted to the backward movement driving part DMTU, and the degree of backward movement, i.e., a moving distance, of the operation member 340 may be determined accordingly.

A detection member 330' may detect motion information of the backward movement driving part DMTU, e.g., a rotation amount of the motor member when the motor member of the backward movement driving part DMTU rotates. As a specific example, the detection member 330' may include an encoder configured to detect the number of rotations or rotation amount of the motor member.

The detection member 330' may be of various forms or types that perform the above functions.

The detection member 330' may be disposed at a position adjacent to or spaced apart from the backward movement driving part DMTU, such as above a pulley PLU, which is rotated by the backward movement driving part DMTU, as illustrated in FIG. 11*a*. However, this is one example, and the detection member 330' may be disposed inside the manipulation part 390 to be adjacent to the backward movement driving part DMTU.

The motion information of the backward movement driving part DMTU, such as the rotation amount or the number of rotations of the motor member, may be measured through the detection member 330', and based on this motion information, related information regarding the movement of the backward movement wire BRW, and a moving distance of the operation member 340 resulting therefrom may be determined as described above. Consequently, position information of the operation member 340 may be detected and provided to a user.

At this time, during the forward movement of the operation member 340, a pulling driving force for moving the backward movement wire BRW backward may not be transmitted from the backward movement driving part DMTU, in which case the position of the backward movement wire BRW may be detected using only the detection member 330 described above.

In addition, as another example, during the forward movement of the operation member 340, the backward movement driving part DMTU may also rotate to actively transmit a driving force to the backward movement wire BRW so that the backward movement wire BRW moves forward in coordination with the driving of the driving part MTU for the forward movement of the operation member 340, and in this case, the position of the backward movement driving part DMTU can be indirectly identified by measuring the rotation amount or number of rotations of the backward movement driving part DMTU through the detection member 330' of the present embodiment. In addition, as another example, instead of the backward movement driving part DMTU actively moving during the forward movement of the operation member 340, the pulley PLU or the backward movement driving part DMTU may also be moved passively by the force resulting from the forward movement of the backward movement wire BRW, and even in this case, the position of the backward movement wire BRW can be indirectly identified by measuring the rotation amount or number of rotations of the backward movement driving part DMTU through the detection member 330' of the present embodiment.

FIG. 11B is a view for describing one modified example of the detection member of FIG. 11A.

Referring to FIG. 11B, a detection member 330" may be disposed in one region of the pulley PLU to detect a motion of the pulley PLU, for example, the detection member 330" may be a proximity sensor and may detect a rotational motion of the pulley PLU when the pulley PLU rotates.

FIG. 11C is a view for describing another modified example of the detection member of FIG. 11A.

Referring to FIG. 11C, a backward movement driving part DMTU' may include a detection member. For example, the backward movement driving part DMTU' may have a sensor-embedded or sensor-integrated structure, and may include a Hall sensor or other various types of sensors (as a specific example a position sensor), and when a motor member of the backward movement driving part DMTU' rotationally moves, the rotationally movement may be detected and the number of rotations or a rotation amount of the motor member may be measured.

As described above, in the embodiments of FIGS. 10A and 10B and their modified examples in FIGS. 11A to 11C, position information of the operation member 340 is determined by detecting a motion of the backward movement wire BRW connected to the operation member 340, and steps of an operation process of the end tool 310 are controlled according thereto.

In an optional embodiment, one or more position detection wires (not shown) may be connected to one region of the operation member 340, such as a rear side of the operation member 340, separately from the backward movement wire BRW (or with the backward movement wire BRW omitted), and the position of the operation member 340 may be determined by detecting the position of the position detection wire. For example, the position detection wire may be similar to the backward movement wire BRW except that the position detection wire does not transmit a driving force for the backward movement of the operation member 340 to the operation member 340. Accordingly, motion information of the position detection wire may be determined through a detection member (e.g., 330) configured to detect the position detection wire and a detection member (e.g., 330' or DMTU') configured to detect the driving part connected to the position detection wire, and the position of the operation member 340 may be determined accordingly.

Figure 12:
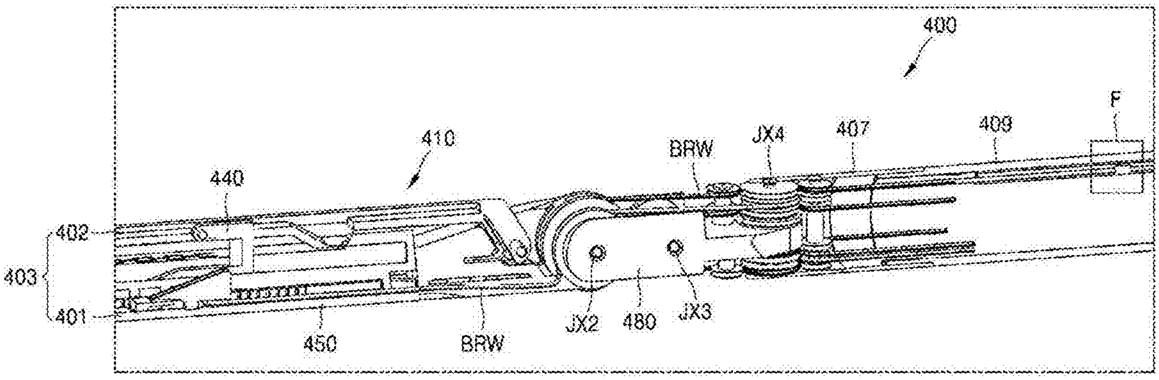
FIG. 12 is a schematic view of a surgical instrument according to another embodiment of the present disclosure.
Figure 13:
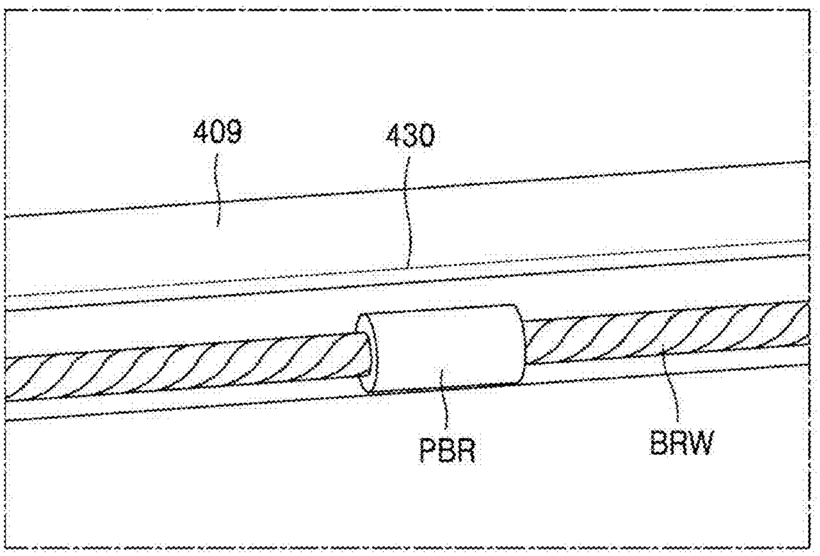
FIG. 13 is an enlarged view of portion F of FIG. 12.

FIG. 12 is a schematic view of a surgical instrument according to another embodiment of the present disclosure. FIG. 13 is an enlarged view of portion F of FIG. 12.

Referring to FIGS. 12 and 13, a surgical instrument 400 of the present embodiment may include an end tool 410. For convenience of description, differences from the above-described embodiment will be mainly described. Specifically, a detection member 430 for detecting a motion of a backward movement wire BRW is different, and thus will be mainly described.

The end tool 410 may include a jaw 403.

The jaw 403 may be formed to accommodate an operation member 440 in at least one region thereof. The jaw 403 may have various forms, such as being configured as one or more jaws, as a specific example, two jaws. For example, the jaw 403 may include a first jaw 401 and a second jaw 402. The first jaw 401 and the second jaw 402 may rotationally move around a rotation shaft JX1.

The backward movement wire BRW may be connected to one region of the operation member 440. The backward movement of the operation member 440 may be performed through the backward movement wire BRW. For example, the backward movement wire BRW may receive a force to move the operation member 440 toward a proximal end of the jaw 403 (the right direction in FIG. 12), and in other words, the backward movement wire BRW may be formed to pull the operation member 440.

Although not shown in the drawings, a driving part or a driving transmission part (e.g., wires, pulleys, and the like) capable of pulling the backward movement wire BRW may be connected to the backward movement wire BRW, and the backward movement wire BRW may be operated according to manual or automatic manipulation.

For example, the backward movement wire BRW may be disposed to extend from the end tool 410 through an end tool shaft 409 to a manipulation part (not shown) and a connection part (not shown) between the end tool shaft 409 and the manipulation part (not shown), and the backward movement wire BRW may be pulled through the manipulation part.

The end tool 410 of the present embodiment may include an end tool hub 480 and a pitch hub 407. The end tool hub 480 may be formed such that one or more rotation shafts JX2 and JX3 are inserted therethrough and one or more pulleys (not shown) corresponding to the one or more rotation shafts JX2 and JX3 are disposed therein. In addition, at least some of the first jaw 401 and the second jaw 402 that are coupled to the rotation shaft JX2 may be accommodated inside the end tool hub 480.

One or more rotation shafts JX4 may be inserted through the pitch hub 407, and the pitch hub 407 may be axially coupled to the end tool hub 480 by the rotation shafts JX4 Accordingly, the end tool hub 480 may be formed to be pitch-rotatable around the rotation shaft JX4 with respect to the pitch hub 407.

The backward movement wire BRW may extend through the end tool hub 480 and the pitch hub 407 to the end tool shaft 409, and may be disposed in the end tool shaft 409 while a path thereof is being guided in correspondence with, for example, one or more pulleys disposed in the end tool hub 480 and the pitch hub 407. The end tool shaft 409 may be an end portion of the manipulation part located at a side of a proximal end of the end tool 410. For example, when the connection part (not shown) connecting the manipulation part to the end tool 410 is disposed, the end tool shaft 409 may be a region of the end tool 410, which is adjacent to or connected to the connection part (not shown).

The detection member 430 may detect motion information of the backward movement wire BRW. For example, the detection member 430 may have the form of a proximity sensor, which detects the motion or position of the backward movement wire BRW. The detection member 430 may have an optically sensing form, or in other cases, may be formed as a contact-type sensor.

The detection member 430 may be disposed in one region, such as, on or adjacent to an inner side surface, of the end tool shaft 409 to detect motion or movement information of the backward movement wire BRW without interrupting the motion thereof. In addition, the detection member 430 may be disposed relatively wide or long, thereby forming a position sensor layer with improved precision.

In an optional embodiment, a measuring member PBR may be disposed in one region of the backward movement wire BRW. The measuring member PBR connected to the backward movement wire BRW moves in response to the movement (forward movement or backward movement) of the backward movement wire BRW, and the moving measuring member PBR is measured by the detection member 430, thereby detecting the motion information of the backward movement wire BRW. Accordingly, it is possible to efficiently detect the motion information of the backward movement wire BRW in a simple manner, and improve the accuracy of detected measurement values.

In addition, as shown in FIG. 13, the detection member 430 and the measuring member PBR may be disposed in the end tool shaft 409 in a relatively large space, may also be disposed in one region adjacent to the end tool 410 and the connection part 1400 connecting the end tool 410 to the manipulation part, or one region of the connection part 1400, thereby improving space utilization and design freedom. As a specific example, with such an arrangement, the relatively small space and structural complexity of the end tool 410 and the manipulation part may be mitigated. By mitigating the structural complexity, the necessary level of accuracy/precision for various components or members disposed in each structure may be reduced, which can improve manufacturing convenience. As a result, the precision and accuracy of the end tool 410 and a surgical instrument including the end tool 410 may be improved.

The operation member 440 is substantially the same as those in the above-described embodiments, and thus a detailed description thereof will be omitted.

As described above, motion information of the backward movement wire BRW may be detected through the detection member 430, and motion and position information of the operation member 440 may be determined through the detected motion information. Through this, it is possible to precisely determine a status of each of steps in the process of performing an operation using the end tool 410 and precisely control initiation of each step's progression.

In addition, the motion of the backward movement wire BRW may be detected stably and with improved precision using the detection member 430 and the measuring member PBR of the backward movement wire BRW, thereby determining the position of the operation member 440.

The detection of the motion and displacement of the backward movement wire BRW during forward or backward movement through the detection member 430 is substantially the same as in the above-described embodiments.

Figure 14:
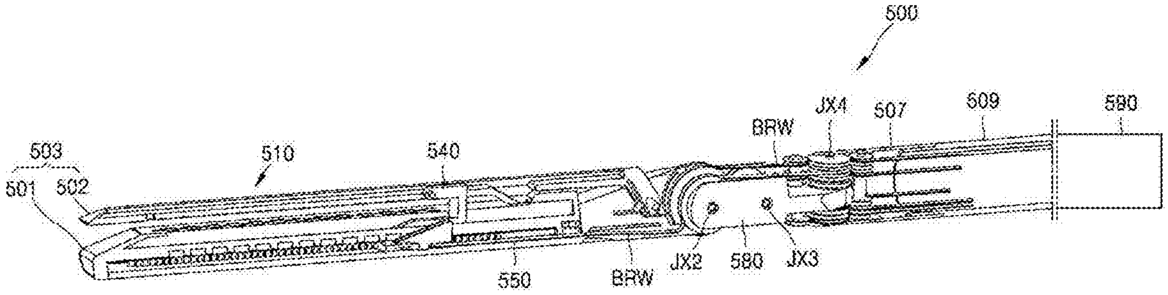
FIG. 14 is a schematic view of a surgical instrument according to another embodiment of the present disclosure.
Figure 15:
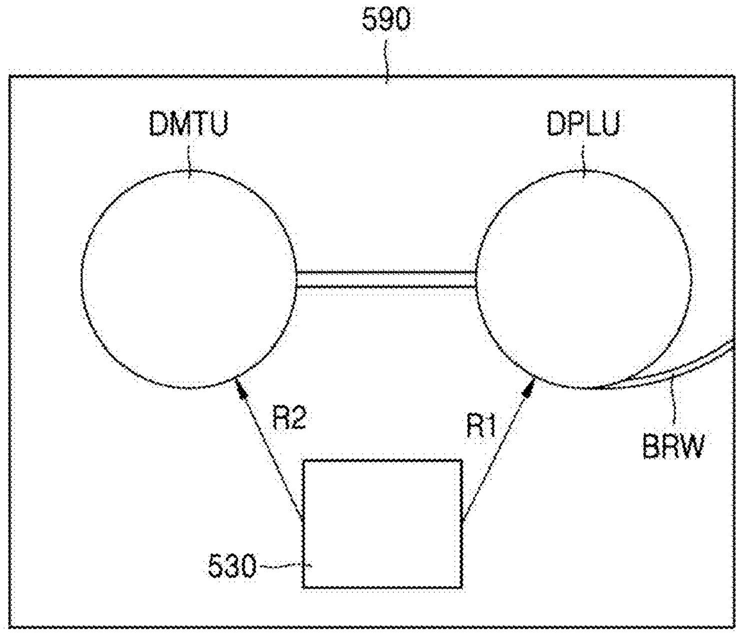
FIG. 15 is a view for describing a detection member of FIG. 14.

FIG. 14 is a schematic view of a surgical instrument according to another embodiment of the present disclosure. FIG. 15 is a view for describing a detection member of FIG. 14.

Referring to FIGS. 14 and 15, a surgical instrument 500 of the present embodiment may include an end tool 510. For convenience of description, differences from the above-described embodiment will be mainly described. Specifically, a detection member 530 for detecting a motion of a backward movement wire BRW is different, and thus will be mainly described.

The end tool 510 is disposed in one region of the surgical instrument 500, such as an end portion thereof, and may be inserted into a surgical site to perform a motion necessary for surgery. In addition, as an example, the end tool 510 may be connected to a manipulation part 590 through one or more connection parts and driven through manipulation of the manipulation part.

The manipulation part 590 may have various forms, including a handle part that can be manipulated by a user, and have the form of a button or the like as another example. The manipulation part 590 may be a robot driving manipulation part when driving a robotic form. The end tool 510 may include a jaw 503.

The jaw 503 may be formed to accommodate an operation member 540 in at least one region thereof. The jaw 503 may have various forms, such as being configured as one or more jaws, as a specific example, two jaws. For example, the jaw 503 may include a first jaw 501 and a second jaw 502. The first jaw 501 and the second jaw 502 may rotationally move around a rotation shaft JX1.

The backward movement wire BRW may be connected to one region of the operation member 540. The backward movement of the operation member 540 may be performed through the backward movement wire BRW. For example, the backward movement wire BRW may receive a force to move the operation member 540 toward a proximal end of the jaw 503 (the right direction in FIG. 14), and in other words, the backward movement wire BRW may be formed to pull the operation member 540.

The backward movement wire BRW may be pulled by a backward movement driving part DMTU capable of pulling the backward movement wire BRW. A driving force of the backward movement driving part DMTU including a driving member such as a motor may be transmitted to the backward movement wire BRW through one or more driving control members DPLU, and the driving control member DPLU may include one or more pulleys.

The backward movement driving part DMTU may be disposed in the manipulation part 590.

The detection member 530 may detect motion information of the backward movement wire BRW. For example, the detection member 530 may detect a motion of the backward movement driving part DMTU, which causes the backward movement wire BRW to move. As a specific example, the detection member 530 may detect a rotation amount of the backward movement driving part DMTU when the backward movement driving part DMTU rotationally moves. In addition, as a specific example, the detection member 530 may include an encoder configured to detect driving information R2 such as the number of rotations or rotation amount of a motor member included in the backward movement driving part DMTU.

In addition, as another example, the driving force of the backward movement driving part DMTU may be transmitted to the backward movement wire BRW through the driving control member DPLU such as a pulley, and the detection member 530 may be formed to detect driving control information R1 such as a rotation amount of the driving control member DPLU.

Further, although not shown in the drawings, in an optional embodiment, the detection member 530 may be disposed inside the backward movement driving part DMTU or integrally formed with the backward movement driving part DMTU.

The operation member 540 is substantially the same as those in the above-described embodiments, and thus a detailed description thereof will be omitted.

As described above, motion information of the backward movement wire BRW may be detected through the detection member 530, and motion and position information of the operation member 540 may be determined through the detected motion information. Through this, it is possible to precisely determine a status of each of steps in the process of performing an operation using the end tool 510 and precisely control initiation of each step's progression.

Further, when the backward movement driving part DMTU moves to transmit a pulling driving force, such as pulling the operation member 540 through the backward movement wire BRW during the backward movement of the operation member 540, the detection member 530 may be used to detect driving information, such as a rotation amount of the backward movement driving part DMTU. By detecting this driving information, the degree of motion, such as the number of rotations, of the backward movement driving part DMTU may be detected, and accordingly, the degree of pulling the backward movement wire BRW may be determined, and a length that the backward movement wire BRW has moved backward may be determined. As a result, the motion information and the position of the operation member 540, which has been moved backward together with the backward movement wire BRW by being connected thereto, may be determined.

Meanwhile, the content described above with reference to FIGS. 11A to 11C is optionally applicable to the present embodiment. That is, as described above, during the forward movement of the operation member 540, the backward movement driving part DMTU connected to the operation member 540 may also rotate to actively transmit a driving force to the backward movement wire BRW to move the backward movement wire BRW forward in coordination with the driving of the driving part for the forward movement of the operation member 540, and in this case, the position of the backward movement driving part DMTU can be indirectly identified by measuring the rotation amount or number of rotations of the backward movement driving part DMTU. In addition, as another example, instead of the backward movement driving part DMTU actively moving during the forward movement of the operation member 540, the driving control member DPLU such as the pulley or the backward movement driving part DMTU may also be moved passively by the force resulting from the forward movement of the backward movement wire BRW, and even in this case, the position of the backward movement wire BRW can be indirectly identified by measuring the rotation amount or number of rotations of the backward movement driving part DMTU.

Figure 16:
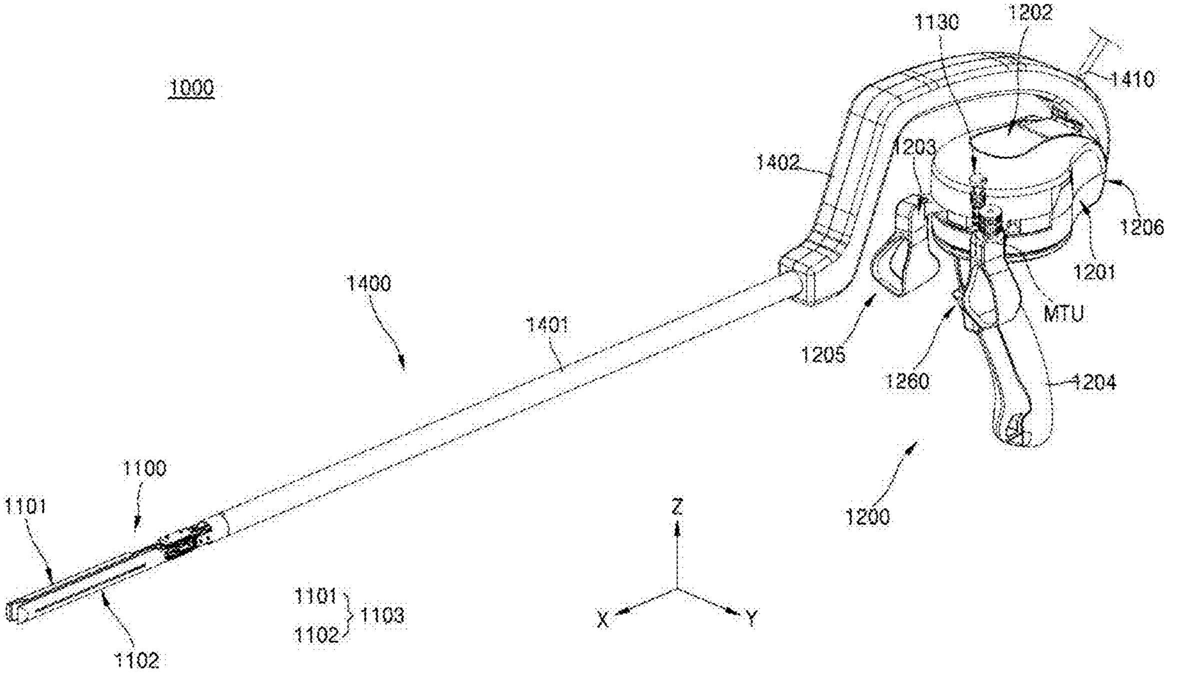
FIG. 16 is a perspective view illustrating a surgical instrument according to another embodiment of the present disclosure.
Figure 17:
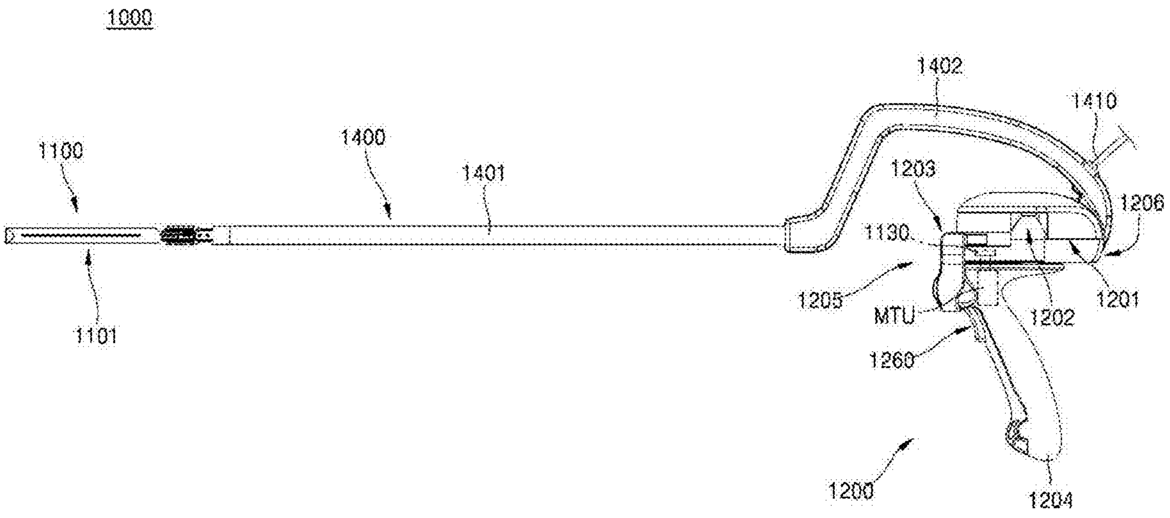
FIG. 17 is a side view of the surgical instrument of FIG. 16.
Figure 18:
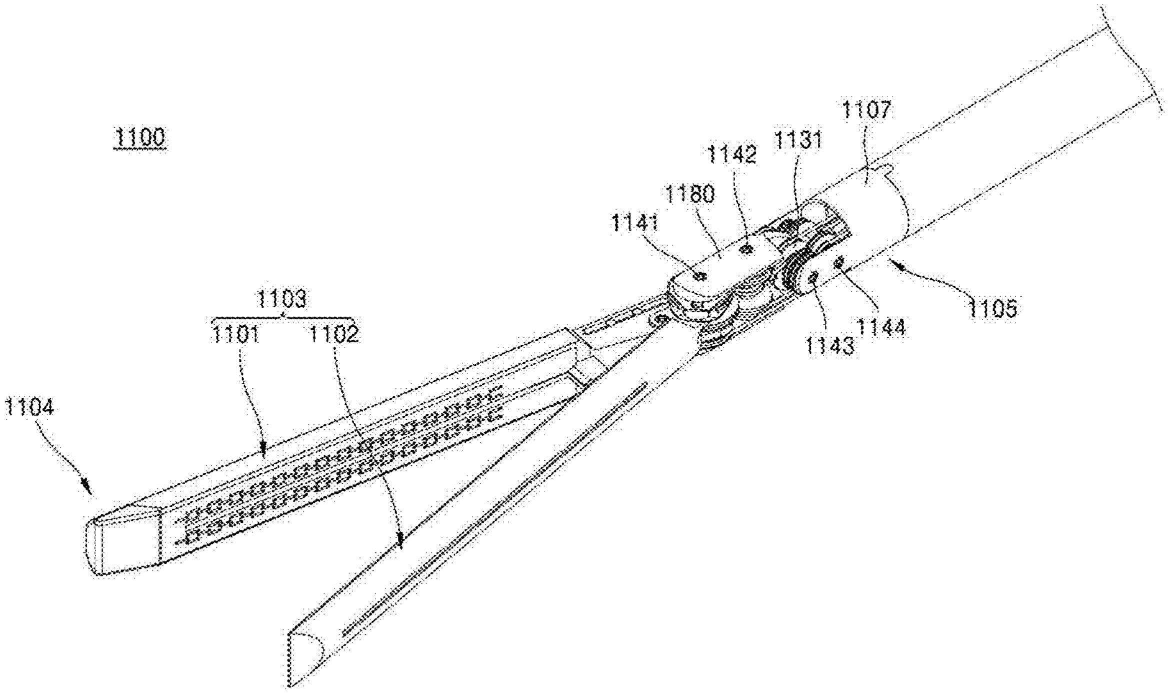
FIG. 18 is a perspective view illustrating an end tool of the surgical instrument of FIG. 16.
Figure 19:
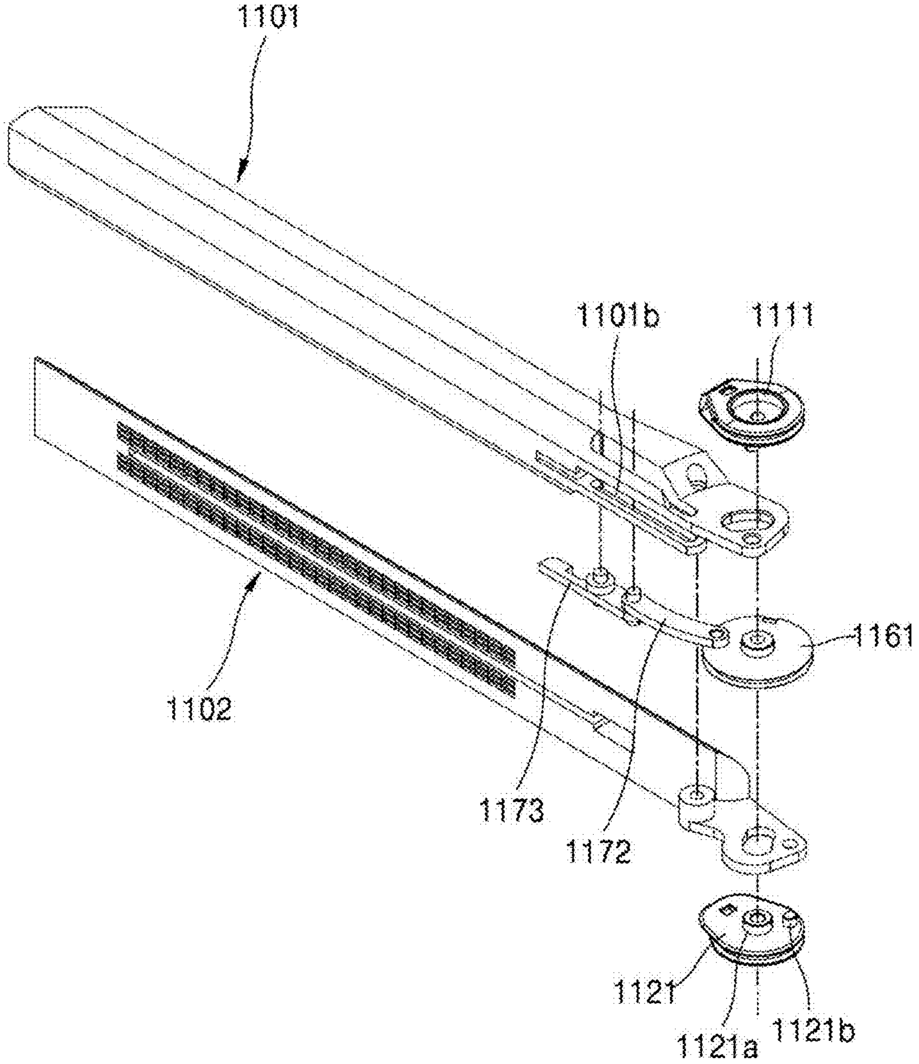
FIGS. 19 and 20 are exploded perspective views of the end tool of the surgical instrument of FIG. 16.
Figure 20:
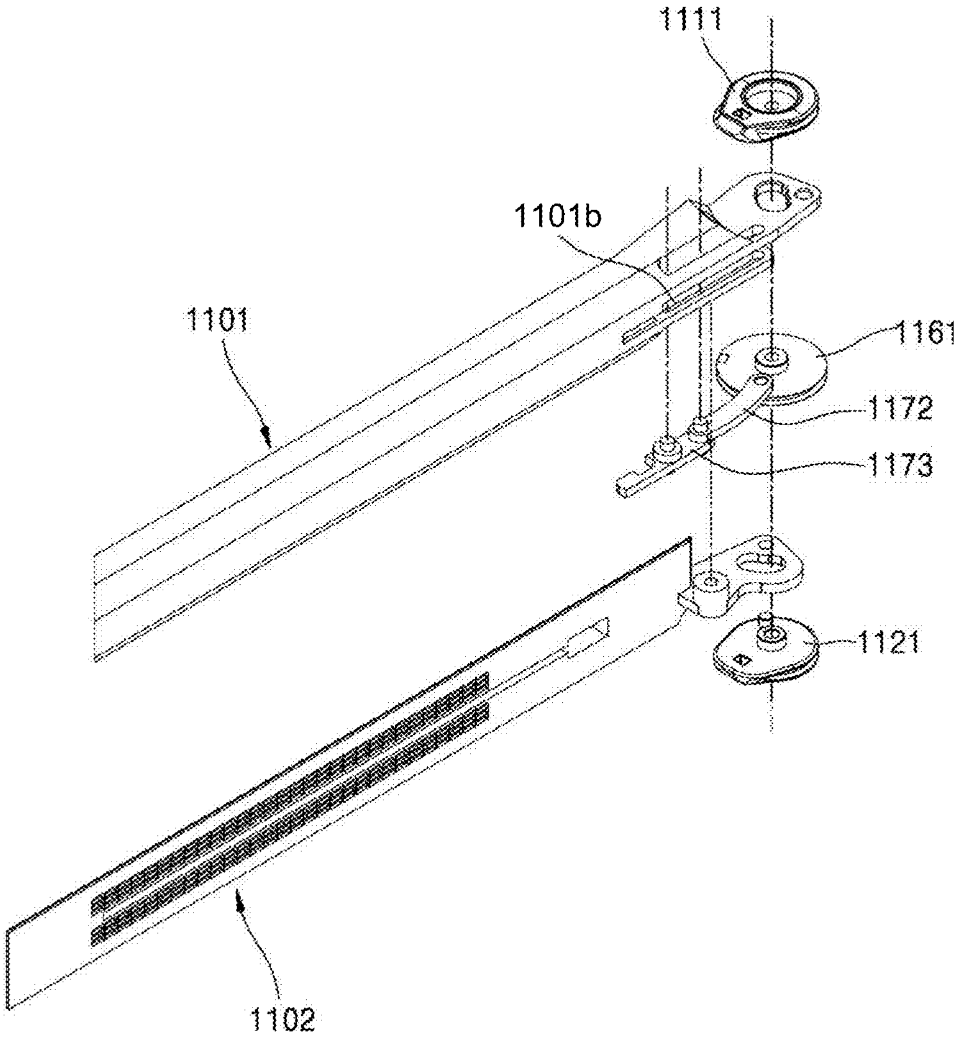
Figure 21:
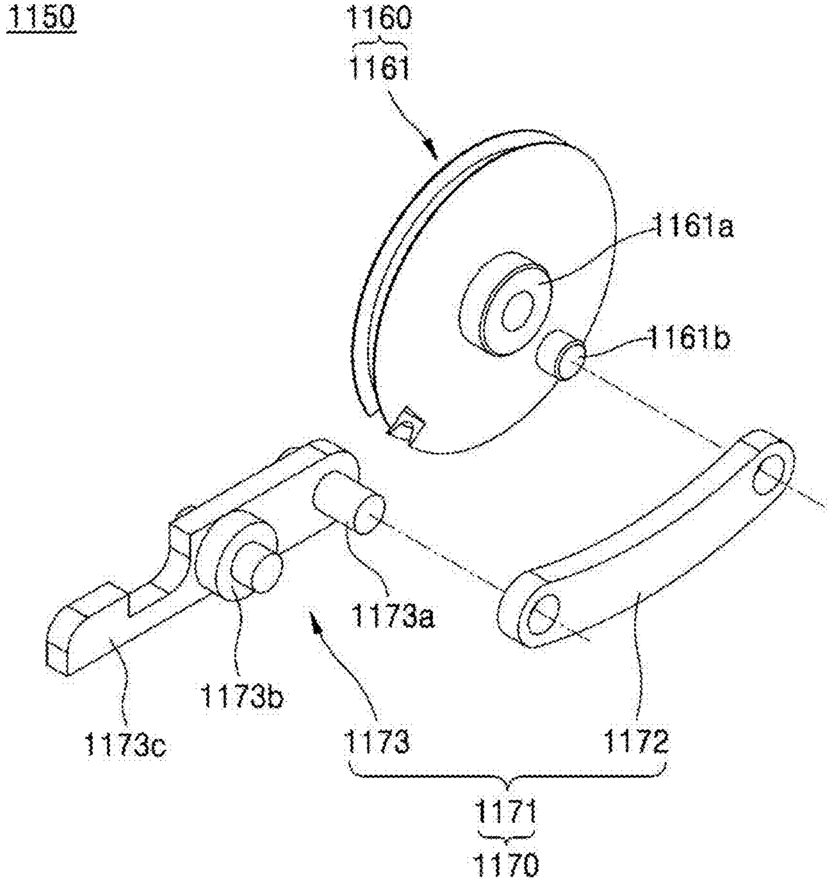
FIG. 21 is an exploded perspective view illustrating a staple pulley and a staple link of the surgical instrument of FIG. 16.
Figure 22:
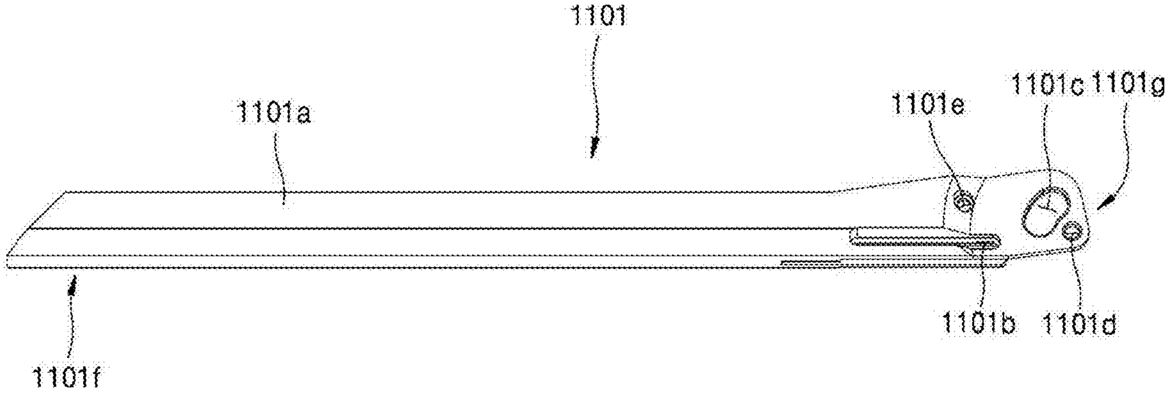
FIG. 22 is a plan view illustrating a first jaw of the surgical instrument of FIG. 16.
Figure 23:
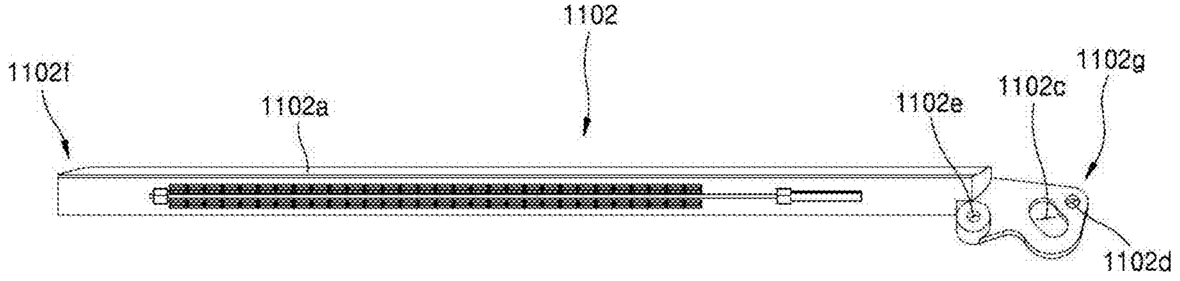
FIG. 23 is a plan view illustrating a second jaw of the surgical instrument of FIG. 16.

FIG. 16 is a perspective view illustrating a surgical instrument according to another embodiment of the present disclosure. FIG. 17 is a side view of the surgical instrument of FIG. 16. FIG. 18 is a perspective view illustrating an end tool of the surgical instrument of FIG. 16. FIGS. 19 and 20 are exploded perspective views of the end tool of the surgical instrument of FIG. 16. FIG. 21 is an exploded perspective view illustrating a staple pulley and the staple link of the surgical instrument of FIG. 16. FIG. 22 is a plan view illustrating a first jaw of the surgical instrument of FIG. 16. FIG. 23 is a plan view illustrating a second jaw of the surgical instrument of FIG. 16.

First, referring to FIGS. 16 and 17, a surgical instrument 1000 according to the present embodiment includes an end tool 1100, a manipulation part 1200, a power transmission part (not shown), and a connection part 1400. In addition, in the surgical instrument 1000 of the present embodiment, position information of an operation member (1540 of FIG. 25) may be determined by detecting its motion.

In addition, a detection member 1130 configured to detect a motion of the operation member (1540 of FIG. 25), e.g., motion information of a driving part MTU, may be disposed, wherein the driving part MTU transmits a driving force causing the operation member 1540 to move to a reciprocating member (1551 of FIG. 25), and the detection member 1130 may be disposed, for example, inside the manipulation part 1200.

The detection member 1130 may include, for example, an encoder for detecting the number of rotations or rotation amount of a motor member of the driving part MTU. As another example, the detection member 1130 may be formed to detect a motion of the pulley that is rotated by the driving part MTU (see FIG. 4). In addition, the detection member 1130 may not be separately provided, and the driving part MTU may have a sensor-embedded or sensor-integrated structure and may include a Hall sensor or other various types of sensors, specifically, as a position sensor. When the motor member of the driving part MTU rotationally moves, the rotational movement may be detected and the number of rotations and rotation amount of the motor member may be measured (see FIG. 5).

The configuration of the surgical instrument 1000 of the present embodiment will be described in more detail.

Here, the connection part 1400 is formed in the shape of a hollow shaft, and one or more wires and electric wires may be accommodated therein. The manipulation part 1200 is coupled to one end portion of the connection part 1400, the end tool 1100 is coupled to the other end portion thereof, and the connection part 1400 may serve to connect the manipulation part 1200 and the end tool 1100. The connection part 1400 includes a straight part 1401 and a bent part 1402, the straight part 1401 is formed on a side of the connection part 1400 coupled to the end tool 1100, and the bent part 1402 is formed on a side of the connection part 1400 to which the manipulation part 1200 is coupled. As such, since the end portion of the connection part 1400 at the side of the manipulation part 1200 is formed to be bent, a pitch manipulation part 1201, a yaw manipulation part 1202, and an actuation manipulation part 1203 may be formed along an extension line of the end tool 1100 or adjacent to the extension line. From another perspective, it may be said that the pitch manipulation part 1201 and the yaw manipulation part 1202 are at least partially accommodated in a concave portion formed by the bent part 1402. Due to the above-described shape of the bent part 1402, the shapes and motions of the manipulation part 1200 and the end tool 1100 may be further intuitively matched with each other.

Meanwhile, a plane on which the bent part 1402 is formed may be substantially the same as a pitch plane, that is, an XZ plane of FIG. 16. As such, as the bent part 1402 is formed on substantially the same plane as the XZ plane, interference with the manipulation part may be reduced. Of course, for intuitive motions of the end tool and the manipulation part, any form other than the XZ plane may be possible.

Meanwhile, a connector 1410 may be formed on the bent part 1402. The connector 1410 may be connected to an external power source (not shown), and the connector 1410 may also be connected to the end tool 1100 via an electric wire, and may transmit, to the end tool 1100, electric energy supplied from the external power source (not shown). In addition, the electric energy transmitted to the end tool 1100 as described above may produce a driving force for rotating a staple pulley (see 1161 of FIG. 19) to be described later in the clockwise or counterclockwise direction. In addition, the electric energy may be supplied to drive the driving part MTU. Of course, a built-in battery may be used.

The manipulation part 1200 is formed at the one end portion of the connection part 1400 and provided as an interface to be directly controlled by a medical doctor, for example, a tongs shape, a stick shape, a lever shape, or the like, and when the medical doctor controls the manipulation part 1200, the end tool 1100, which is connected to the interface and inserted into the body of a surgical patient, performs a certain motion, thereby performing surgery. Here, the manipulation part 1200 is illustrated in FIG. 16 as being formed in a handle shape that is rotatable while the finger is inserted therein, but the concept of the present disclosure is not limited thereto, and various types of manipulation parts that can be connected to the end tool 1100 and manipulate the end tool 1100 may be possible.

The end tool 1100 is formed on the other end portion of the connection part 1400, and performs necessary motions for surgery by being inserted into a surgical site. As an example of the end tool 1100 described above, a pair of jaws 1103 for performing a grip motion may be used as shown in FIG. 16. However, the concept of the present disclosure is not limited thereto, and various devices for performing surgery may be used as the end tool 1100. For example, a configuration of a cantilever cautery may also be used as the end tool. The end tool 1100 is connected to the manipulation part 1200 by a power transmission part (not shown), and receives a driving force of the manipulation part 1200 through the power transmission part (not shown) to perform a motion necessary for surgery, such as gripping, cutting, suturing, or the like.

Here, the end tool 1100 of the surgical instrument 1000 according to another embodiment of the present disclosure is formed to be rotatable in at least one direction, for example, the end tool 1100 may perform a pitch motion around a Y-axis of FIG. 16 and simultaneously perform a yaw motion and an actuation motion around a Z-axis of FIG. 16.

Here, each of the pitch, yaw, and actuation motions used in the present disclosure are defined as follows.

First, the pitch motion means a motion of the end tool 1100 rotating in a vertical direction with respect to an extension direction of the connection part 1400 (an X-axis direction of FIG. 16), that is, a motion rotating around the Y-axis of FIG. 16. In other words, the pitch motion means a motion of the end tool 1100, which is formed to extend from the connection part 1400 in the extension direction of the connection part 1400 (the X-axis direction of FIG. 16), rotating vertically around the Y-axis with respect to the connection part 1400.

Next, the yaw motion means a motion of the end tool 1100 rotating in the left and right directions, that is, a motion rotating around the Z-axis of FIG. 16, with respect to the extension direction of the connection part 1400 (the X-axis direction of FIG. 16). In other words, the yaw motion means a motion of the end tool 1100, which is formed to extend from the connection part 1400 in the extension direction of the connection part 1400 (the X-axis direction of FIG. 16), rotating horizontally around the Z-axis with respect to the connection part 1400. That is, the yaw motion means a motion of the two jaws 1103, which are formed on the end tool 1100, rotating around the Z-axis in the same direction.

Meanwhile, the actuation motion may mean a motion of the end tool 1100 rotating around the same axis of rotation as that of the yaw motion, while the two jaws 1103 rotating in the opposite directions so as to be closed or opened. That is, the actuation motion means rotating motions of the two jaws 1103, which are formed on the end tool 1100, in the opposite directions around the Z-axis.

The power transmission part (not shown) may connect the manipulation part 1200 to the end tool 1100, transmit the driving force of the manipulation part 1200 to the end tool 1100, and include a plurality of wires, pulleys, links, sections, gears, or the like.

The end tool 1100, the manipulation part 1200, and the like of the surgical instrument 1000 of FIG. 16 will be described in detail later.

(Intuitive Driving)

Hereinafter, intuitive driving of the surgical instrument 1000 of the present disclosure will be described.

First, a user may perform a pitch motion by rotating a first handle 1204 around the Y-axis while holding the first handle 1204 with a palm thereof, and perform a yaw motion by rotating the first handle 1204 around the Z-axis. In addition, the user may perform an actuation motion by manipulating the actuation manipulation part 1203 in a state in which the thumb and the index finger are inserted into a hand ring-shaped extension part formed at one end portion of the actuation manipulation part 1203.

Here, in the surgical instrument 1000 according to another embodiment of the present disclosure, when the manipulation part 1200 is rotated in one direction with respect to the connection part 1400, the end tool 1100 is rotated in a direction that is intuitively the same as a manipulation direction of the manipulation part 1200. In other words, when the first handle 1204 of the manipulation part 1200 is rotated in one direction, the end tool 1100 is also rotated in a direction intuitively the same as the one direction, so that a pitch motion or a yaw motion is performed. Here, the phrase "intuitively the same direction" may be further explained as meaning that a direction of movement of the user's finger gripping the manipulation part 1200 and a direction of movement of a distal end of the end tool 1100 form substantially the same direction. Of course, "the same direction" as used herein may not be a perfectly matching direction on a three-dimensional coordinate, and may be understood to be equivalent to the extent that, for example, when the user's finger moves to the left, the distal end of the end tool 1100 is moved to the left, and when the user's finger moves down, the end portion of the end tool 1100 is moved down.

In addition, to this end, in the surgical instrument 1000 according to the present embodiment, the manipulation part 1200 and the end tool 1100 are formed in the same direction with respect to a plane perpendicular to the extension axis (X-axis) of the connection part 1400. That is, when viewed based on a YZ plane of FIG. 16, the manipulation part 1200 is formed to extend in a positive (+) X-axis direction, and the end tool 1100 is also formed to extend in the positive (+) X-axis direction. In other words, it may be said that a formation direction of the end tool 1100 on one end portion of the connection part 1400 is the same as a formation direction of the manipulation part 1200 on the other end portion of the connection part 1400 on the basis of the YZ plane. Further, in other words, it may be said that the manipulation part 1200 may be formed in a direction away from the body of a user holding the manipulation part 1200, that is, in a direction in which the end tool 1100 is formed. In other words, the first handle 1204 or the like, which the user grips and moves to perform the actuation motion, the yaw motion, the pitch motion, and the like, is formed such that the portion that moves to perform each motion extends in the positive (+) X-axis direction beyond the center of rotation of each joint for that motion. In this manner, the manipulation part 1200 may be configured in the same manner as the end tool 1100 in which each moving portion is formed to extend in the positive (+) X-axis direction from the rotation center of a corresponding joint for the motion, and the manipulation direction of the user may be identical to an operation direction of the end tool from the viewpoint of the rotation directions and the left and right directions. As a result, intuitively the same manipulation may be achieved.

(End Tool)

Hereinafter, the end tool 1100 of the surgical instrument 1000 will be described in more detail.

FIG. 18 is a perspective view illustrating the end tool of the surgical instrument of FIG. 16.

FIGS. 19 and 20 are exploded perspective views of the end tool of the surgical instrument of FIG. 16.

The end tool 1100 of the present embodiment includes a pair of jaws for performing a grip motion, that is, a first jaw 1101 and a second jaw 1102. Here, each of the first jaw 1101 and the second jaw 1102, or a component encompassing the first jaw 1101 and the second jaw 1102 may be referred to as the jaw 1103.

In addition, the end tool 1100 may include a plurality of pulleys including a pulley 1111 related to a rotational motion of the first jaw 1101. In addition, the end tool 1100 may include a plurality of pulleys, including a pulley 1121 associated with rotational movement of the second jaw 1102.

Here, the pulleys facing each other are illustrated in the drawings as being formed parallel to each other, but the concept of the present disclosure is not limited thereto, and each of the pulleys may be variously formed with a position and a size suitable for the configuration of the end tool.

Further, the end tool 1100 of the present embodiment may include an end tool hub 1180 and a pitch hub 1107.

A rotation shaft 1141 and a rotation shaft 1142 may be inserted through the end tool hub 1180, and the end tool hub 1180 may internally accommodate at least some of one or more pulleys that are axially coupled to the rotation shaft 1141. In addition, the end tool hub 1180 may internally accommodate at least some of one or more pulleys that are axially coupled to the rotation shaft 1142.

In addition, at least some of a staple pulley assembly (see 1160 of FIG. 21) and a staple link assembly (see 1170 of FIG. 21) to be described later may be formed at one side of the end tool hub 1180, e.g., in a space adjacent to the center of the end tool hub 1180.

Meanwhile, a pulley 1131 serving as an end tool pitch pulley may be formed at one end portion of the end tool hub 1180. Alternatively, the pulley 1131 may be integrally formed with the end tool hub 1180 as one body. That is, a disk-shaped pulley is formed at one end portion of the end tool hub 1180, and a groove around which a wire may be wound may be formed on an outer circumferential surface of the pulley. Alternatively, the pulley 1131 may be formed as a separate member from the end tool hub 1180 to be coupled to the end tool hub 1180.

A rotation shaft 1143 and a rotation shaft 1144 are inserted through the pitch hub 1107, and the pitch hub 1107 may be axially coupled to the end tool hub 1180 (and the pulley 1131) by the rotation shaft 1143. Thus, the end tool hub 1180 and the pulley 1131 may be formed to be rotatable around the rotation shaft 1143 with respect to the pitch hub 1107.

In addition, the pitch hub 1107 may internally accommodate at least some one or more pulleys that are axially coupled to the rotation shaft 1143. In addition, the pitch hub 1107 may internally accommodate at least some one or more pulleys that are axially coupled to the rotation shaft 1144.

In addition, the end tool 1100 of the present embodiment may include the rotation shaft 1141, the rotation shaft 1142, the rotation shaft 1143, and the rotation shaft 1144. As described above, the rotation shaft 1141 and the rotation shaft 1142 may be inserted through the end tool hub 1180, and the rotation shaft 1143 and the rotation shaft 1144 may be inserted through the pitch hub 1107.

The rotation shaft 1141, the rotation shaft 1142, the rotation shaft 1143, and the rotation shaft 1144 may be arranged sequentially from a distal end 1104 of the end tool 1100 toward a proximal end 1105. Accordingly, starting from the distal end 1104, the rotation shaft 1141 may be referred to as a first pin, the rotation shaft 1142 may be referred to as a second pin, the rotation shaft 1143 may be referred to as a third pin, and the rotation shaft 1144 may be referred to as a fourth pin.

Here, the rotation shaft 1141 may function as an end tool jaw pulley rotation shaft, the rotation shaft 1142 may function as an end tool jaw auxiliary pulley rotation shaft, the rotation shaft 1143 may function as an end tool pitch rotating shaft, and the rotation shaft 1144 may function as an end tool pitch auxiliary rotating shaft of the end tool 1100.

One or more pulleys may be inserted into each of the rotation shafts 1141 1142, 1143, and 1144.

Meanwhile, a rotation shaft may be further formed on one side of the rotation shaft 1141, specifically, one side of the rotation shaft 1141 at the distal end 1104 side.

The pulley 1111 functions as an end tool first jaw pulley, and the pulley 1121 functions as an end tool second jaw pulley. The pulley 1111 may also be referred to as a first jaw pulley, and the pulley 1121 may also be referred to as a second jaw pulley, and these two components may also be referred to collectively as an end tool jaw pulley or simply a jaw pulley.

The pulley 1111 and the pulley 1121, which are end tool jaw pulleys, are formed to face each other, and are formed to be rotatable independently of each other around the rotation shaft 1141, which is an end tool jaw pulley rotation shaft. In this case, the pulley 1111 and the pulley 1121 are formed to be spaced apart from each other by a certain extent, and the staple assembly accommodation part may be formed therebetween. In addition, at least some of a staple pulley assembly 1160 and a staple link assembly 1170, which will be described later, may be disposed inside the staple assembly accommodation part.

Here, in the drawings, it is illustrated that the pulley 1111 and the pulley 1121 are formed to rotate around one rotation shaft 1141, but it is of course possible that each end tool jaw pulley may be formed to be rotatable around a separate shaft. Here, the first jaw 1101 is fixedly coupled to the pulley 1111 and rotates together with the pulley 1111, and the second jaw 1102 is fixedly coupled to the pulley 1121 and rotates together with the pulley 1121. Yaw and actuation motions of the end tool 1100 are performed in response to the rotation of the pulley 1111 and the pulley 1121. That is, when the pulley 1111 and the pulley 1121 are rotated in the same direction around the rotation shaft 1141, the yaw motion is performed, and when the pulley 1111 and the pulley 1121 are rotated in opposite directions around the rotation shaft 1141, the actuation motion is performed.

Here, the first jaw 1101 and the pulley 1111 may be formed as separate members and coupled to each other, or the first jaw 1101 and the pulley 1111 may be integrally formed as one body. Similarly, the second jaw 1102 and the pulley 1121 may be formed as separate members and coupled to each other, or the second jaw 1102 and the pulley 1121 may be integrally formed as one body.

In addition, one or more auxiliary pulleys may be disposed adjacent to the pulley 1111 and the pulley 1112.

These pulleys may be formed such that one or more wires are wound therearound, the pulleys may be rotated by the wires, and the wires may move along the pulleys, thereby transmitting a driving force to the end tool 1100.

(Components Related to Staple Pulley)

Hereinafter, the staple pulley 1161 of the end tool 1100 of the surgical instrument 1000 of FIG. 16 will be described in more detail.

FIGS. 19 and 20 are exploded perspective views of the end tool of the surgical instrument of FIG. 16.

FIG. 21 is an exploded perspective view illustrating the staple pulley and the staple link of the surgical instrument of FIG. 16.

The end tool 1100 of the present embodiment may include one or more pulleys including the staple pulley 1161 associated with linear motion/rotational motion of the respective pulleys and links for stapling and cutting.

The staple pulley 1161 is formed to face each of the pulley 1111 and the pulley 1121, which are end tool jaw pulleys, and the staple pulley 1161 and the pulley 1111 and the pulley 1121 are formed to be rotatable independently of each other around the rotation shaft 1141, which is an end tool jaw pulley rotation shaft. Here, the staple pulley 1161 is illustrated as being disposed between the pulley 1111 and the pulley 1121, but the concept of the present disclosure is not limited thereto, and the staple pulley 1161 may be disposed at various positions adjacent to the pulley 1111 or the pulley 1121.

Here, in the present disclosure, the staple pulley 1161, the pulley 1111, and the pulley 1121 are formed to rotate around substantially the same shaft. As the staple pulley 1161, the pulley 1111, and the pulley 1121 are formed to rotate around the same shaft as described above, it is possible to perform a pitch motion/yaw motion/actuation motion as well as stapling and cutting motions.

Although the staple pulley 1161, the pulley 1111, and the pulley 1121 are illustrated in the drawing as being formed to rotate around one rotation shaft 1141, it is of course possible that each jaw pulley may be formed to be rotatable around a separate shaft that is concentric therewith.

In other words, it may also be described as a structure in which the first jaw pulley, pulley 1111, the staple pulley 1161, and the pulley 1121 that is a second jaw pulley are sequentially stacked along the rotation shaft 1141. Alternatively, it may be also described as a structure in which the staple pulley 1161 is disposed between the pulley 1111 and the pulley 1121 facing each other. Here, the first jaw pulley 1111, the staple pulley 1161, and the second jaw pulley 1121 may be formed to be rotatable independently of each other.

One or more staple auxiliary pulleys (not shown) may further be provided on one side of the staple pulley 1161.

In addition, one or more pulleys (not shown) may function as staple pitch main pulleys, and the other one or more pulleys may function as staple pitch sub-pulleys.

As one or more wires are pulled and released by the driving part MTU of FIG. 16, the staple pulley 1161 coupled thereto may be rotated in one direction, and stapling may be performed accordingly.

In addition, in an optional embodiment, one or more staple auxiliary pulleys (not shown) are disposed to increase a radius of rotation of the staple pulley 1161, thereby increasing a yaw motion range in which normal stapling and cutting operations may be performed.

(Staple Drive Assembly)

Hereinafter, a staple drive assembly 1150 will be described in more detail.

Referring to FIG. 21 and the like, the staple drive assembly 1150 may include the staple pulley assembly 1160 and the staple link assembly 1170. Here, the staple drive assembly 1150 is connected to a reciprocating assembly 1550 of a cartridge 1500 to be described later, and converts a rotational motion of the staple pulley 1161 into a linear motion of the reciprocating assembly 1550. In other embodiments of the present disclosure, which will be described later, the staple drive assembly may be understood as a concept including the staple pulley assembly and the staple link assembly. A driving force is transmitted to the staple drive assembly 1150 through the driving part MTU, and the reciprocating assembly 1550 and the operation member 1540 connected thereto are moved due to the movement of the staple drive assembly 1150. Since the driving part MTU is detected (e.g., the number of rotations of the motor member is detected) through the detection member 1130, the motion and position information of the operation member 1540 may be precisely identified.

The staple pulley assembly 1160 may include one or more staple pulleys 1161. The staple pulley assembly 1160 may be formed between the pulley 1111 and the pulley 1121 to be adjacent to the pulley 1111 and the pulley 1121. In the present embodiment, it is assumed that the staple pulley assembly 1160 includes one staple pulley 1161.

A shaft pass-through part 1161*a* may be formed in the staple pulley 1161. The shaft pass-through part 1161*a* may be formed in the form of a hole, and the rotation shaft 1141, which is an end tool jaw pulley rotation shaft, may be inserted through the shaft pass-through part 1161*a*. In addition, a link coupling part 1161*b* may be formed on the staple pulley 1161. The staple link assembly 1170 to be described later may be coupled to the link coupling part 1161*b*. This will be described in more detail later.

Meanwhile, the end tool 1100 of the present embodiment may further include the staple link assembly 1170 connected to the staple pulley assembly 1160. The staple link assembly 1170 may include one or more link members 1171. The staple link assembly 1170 may serve to connect the staple pulley assembly 1160 to the reciprocating assembly 1550 of the cartridge 1500 to be described later. In the present embodiment, it is assumed that the staple link assembly 1170 includes one link member 1171, and the link member 1171 includes a first link 1172 and a second link 1173.

The first link 1172 is formed in the form of an elongated bar, which may have through holes formed at both end portions. The link coupling part 1161*b* of the staple pulley 1161 may be inserted through the through hole at one end portion of the first link 1172. The second link 1173 may be inserted through the through hole at the other end portion of the first link 1172.

The second link 1173 is formed in the form of an elongated bar, and may be coupled to the first link 1172. The second link 1173 may include a first protrusion 1173*a*, a second protrusion 1173*b*, and a coupling part 1173*c*.

In detail, the first protrusion 1173*a* may be formed at one end portion of the second link 1173. The first protrusion 1173*a* is axially coupled to the first link 1172 by being fitted into the through hole of the first link 1172, so that the second link 1173 may be coupled to the first link 1172. In addition, the first protrusion 1173*a* may be fitted into a guide groove 1101*b* of the first jaw 1101, which will be described later.

Meanwhile, the second protrusion 1173*b* may be formed in one region of a central portion of the second link 1173. The second protrusion 1173*b* may be fitted into the guide groove 1101*b* of the first jaw 1101, which will be described later.

As described above, as the first protrusion 1173*a* and the second protrusion 1173*b* are moved along the guide groove 1101*b* in a state in which the first protrusion 1173*a* and the second protrusion 1173*b* of the second link 1173 formed in a protruding shape are fitted into the groove-shaped guide groove 1101*b*, the staple link assembly 1170 is moved with respect to the first jaw 1101 (and the cartridge 1500 therein). This will be described in more detail later.

Meanwhile, the coupling part 1173*c* may be formed at the other end portion of the second link 1173. The coupling part 1173*c* may be coupled to a coupling part 1551*a* of the reciprocating assembly 1550 of the cartridge 1500, which will be described later.

In the state as shown in FIG. 21, when the staple pulley 1161 is rotated in the clockwise direction, the link member 1171 connected to the staple pulley 1161 may be moved as a whole toward a distal end (see 1101*f* of FIG. 22) of the first jaw 1101. In contrast, when the staple pulley 1161 is rotated in the counterclockwise direction, the link member 1171 connected to the staple pulley 1161 may be moved as a whole toward a proximal end (see 1101*g* of FIG. 22) of the first jaw 1101.

Thus, a bidirectional rotational motion of the staple pulley assembly 1160 causes a reciprocating linear motion of the reciprocating assembly 1550 of the cartridge 1500 through the staple link assembly 1170. This will be described in more detail later.

(Motion of First and Second Jaws)

FIG. 22 is a plan view illustrating the first jaw of the surgical instrument of FIG. 16. FIG. 23 is a plan view illustrating the second jaw of the surgical instrument of FIG. 16.

Referring to FIGS. 22 and 23 and the like, the first jaw 1101 includes a cartridge accommodation part 1101*a*, the guide groove 1101*b*, a movable-coupling hole 1101*c*, a jaw pulley coupling hole 1101*d*, and a shaft pass-through part 1101*e*.

The first jaw 1101 is formed entirely in the shape of an elongated bar, the cartridge (1500 of FIG. 24) is accommodated in the distal end 1101*f* side, and the pulley 1111 is coupled to the proximal end 1101*g*, so that the first jaw 1101 is formed to be rotatable around the rotation shaft 1141. In other words, the first jaw 1101 may be formed entirely in the form of a hollow box with one surface (upper surface) thereof is removed, such that the cartridge accommodation part 1101*a* capable of accommodating the cartridge 1500 may be formed inside the first jaw 1101. That is, the first jaw 1101 may be formed in an approximately "U" shape in cross section.

The guide groove 1101*b* configured to guide the movement of the staple link assembly 1170, which will be described later, may be formed on one side of the cartridge accommodation part 1101*a* of the first jaw 1101, e.g., on the proximal end 1101*g* side. The guide groove 1101*b* may be formed in the shape of a groove formed along a moving path of the staple link assembly 1170. In addition, as the first protrusion 1173*a* and the second protrusion 1173*b* are moved along the guide groove 1101*b* in a state in which the first protrusion 1173*a* and the second protrusion 1173*b* of the second link 1173 formed in a protruding shape are fitted into the groove-shaped guide groove 1101*b*, the staple link assembly 1170 is moved with respect to the first jaw 1101

(and the cartridge 1500 therein). That is, the staple link assembly 1170 may be moved along the guide groove 1101*b* of the first jaw 1101.

Meanwhile, the movable-coupling hole 1101*c*, the jaw pulley coupling hole 1101*d*, and the shaft pass-through part 1101*e* may be formed on the proximal end side of the first jaw 1101.

Here, the movable-coupling hole 1101*c* may be formed to have a predetermined curvature, and may be formed in an approximately elliptical shape. A shaft coupling part of the pulley 1111 may be fitted into the movable-coupling hole 1101*c*. Here, a short radius of the movable-coupling hole 1101*c* may be formed to be substantially the same as or slightly greater than a radius of the shaft coupling part. Meanwhile, a long radius of the movable-coupling hole 1101*c* may be formed to be greater than the radius of the shaft coupling part. Thus, in a state in which the shaft coupling part of the pulley 1111 is fitted into the movable-coupling hole 1101*c* of the first jaw 1101, the shaft coupling part is movable to a certain extent in the movable-coupling hole 1101*c*.

Meanwhile, the jaw pulley coupling hole 1101*d* is formed in the form of a cylindrical hole, and a jaw coupling part of the pulley 1111 may be fitted into the jaw pulley coupling hole 1101*d*. Here, a radius of the jaw pulley coupling hole 1101*d* may be formed to be substantially the same as or slightly greater than a radius of the jaw coupling part. Thus, the jaw coupling part of the pulley 1111 may be formed to be rotatably coupled to the jaw pulley coupling hole 1101*d* of the first jaw 1101.

The shaft pass-through part 1101*e* may be formed at the distal end 1101*f* side of the first jaw 1101 relative to the movable-coupling hole 1101*c* and the jaw pulley coupling hole 1101*d*. The shaft pass-through part 1101*e* may be formed in the form of a hole, and the rotation shaft 1145, which is a jaw rotation shaft, may be inserted through the shaft pass-through part 1101*e*.

The second jaw 1102 includes an anvil 1102*a*, a movable-coupling hole 1102*c*, a jaw pulley coupling hole 1102*d*, and a shaft pass-through part 1102*e*.

The second jaw 1102 is formed entirely in the shape of an elongated bar, the anvil 1102*a* is formed on a distal end 1102*f* side, and the pulley 1112 is coupled to a proximal end 1102*g*, so that the second jaw 1102 is formed to be rotatable around the rotation shaft 1141.

In detail, the anvil 1102*a* is formed in the form of a flat plane, on one surface of which shapes corresponding to the shapes of staples 1530 to be described later may be formed. The above-described anvil 1102*a* may serve as a support for supporting the staple 1530 on the opposite side of the operation member 1540 when the operation member 1540 pushes and raises the staple 1530 during a stapling motion, so that the staple 1530 is bent.

Meanwhile, the movable-coupling hole 1102*c*, the jaw pulley coupling hole 1102*d*, and the shaft pass-through part 1102*e* may be formed on the proximal end side of the second jaw 1102.

Here, the movable-coupling hole 1102*c* may be formed to have a predetermined curvature, and may be formed in an approximately elliptical shape. A shaft coupling part of the pulley 1121 may be fitted into the movable-coupling hole 1102*c*. Here, a short radius of the movable-coupling hole 1102*c* may be formed to be substantially the same as or slightly greater than a radius of the shaft coupling part. Meanwhile, a long radius of the movable-coupling hole 1102*c* may be formed to be greater than the radius of the shaft coupling part. Thus, in a state in which the shaft coupling part of the pulley 1121 is fitted into the movable-coupling hole 1102*c* of the second jaw 1102, the shaft coupling part is movable to a certain extent in the movable-coupling hole 1102*c*.

Meanwhile, the jaw pulley coupling hole 1102*d* is formed in the form of a cylindrical hole, and a jaw coupling part of the pulley 1121 may be fitted into the jaw pulley coupling hole 1102*d*. Here, a radius of the jaw pulley coupling hole 1102*d* may be formed to be substantially the same as or slightly greater than a radius of the jaw coupling part. Thus, the jaw coupling part of the pulley 1121 may be formed to be rotatably coupled to the jaw pulley coupling hole 1102*d* of the second jaw 1102.

Meanwhile, the shaft pass-through part 1102*e* may be formed at the proximal end 1102*g* side of the second jaw 1102 relative to the movable-coupling hole 1102*c* and the jaw pulley coupling hole 1102*d*. The shaft pass-through part 1102*e* may be formed in the form of a hole, and the jaw rotation shaft may be inserted through the shaft pass-through part 1102*e*.

The coupling relationship between the components described above is as follows.

The rotation shaft 1141, which is an end tool jaw pulley rotation shaft, is sequentially inserted through the shaft coupling part of the pulley 1111, the movable-coupling hole 1101*c* of the first jaw 1101, the shaft pass-through part 1161*a* of the staple pulley 1161, the movable-coupling hole 1102*c* of the second jaw 1102, and a shaft coupling part 1121*a* of the pulley 1121.

The jaw rotation shaft is sequentially inserted through the shaft pass-through part 1101*e* of the first jaw 1101 and the shaft pass-through part 1102*e* of the second jaw 1102.

The shaft coupling part of the pulley 1111 is fitted into the movable-coupling hole 1101*c* of the first jaw 1101, and the jaw coupling part of the pulley 1111 is fitted into the jaw pulley coupling hole 1101*d* of the first jaw 1101.

At this time, the jaw pulley coupling hole 1101*d* of the first jaw 1101 and the jaw coupling part of the pulley 1111 are axially coupled to each other so as to be rotatable, and the movable-coupling hole 1101*c* of the first jaw 1101 and the shaft coupling part of the pulley 1111 are movably coupled to each other.

The shaft coupling part 1121*a* of the pulley 1121 is fitted into the movable-coupling hole 1102*c* of the second jaw 1102, and a jaw coupling part 1121*b* of the pulley 1121 is fitted into the jaw pulley coupling hole 1102*d* of the second jaw 1102.

At this time, the jaw pulley coupling hole 1102*d* of the second jaw 1102 and the jaw coupling part 1121*b* of the pulley 1121 are axially coupled to each other to be rotatable, and the movable-coupling hole 1102*c* of the second jaw 1102 and the shaft coupling part 1121*a* of the pulley 1121 are movably coupled to each other.

Here, the pulley 1111 and the pulley 1121 are rotated around the rotation shaft 1141, which is an end tool jaw pulley rotation shaft. The first jaw 1101 and the second jaw 1102 are rotated around the jaw rotation shaft. That is, the pulley 1111 and the first jaw 1101 have different shafts of rotation. Similarly, the pulley 1121 and the second jaw 1102 have different shafts of rotation.

That is, the rotation angle of the first jaw 1101 is limited to a certain extent by the movable-coupling hole 1101*c*, but the first jaw 1101 is essentially rotated around a rotation shaft 1145, which is a jaw rotation shaft. Similarly, the rotation angle of the second jaw 1102 is limited to a certain extent by the movable-coupling hole 1102*c*, but second jaw 1102 is essentially rotated around the rotation shaft 1145, which is a jaw rotation shaft.

This allows a grip force to be amplified. That is, in the surgical instrument 1000 according to an embodiment of the present disclosure, the coupling structure of the first jaw 1101 and the second jaw 1102 forms an X-shaped structure, and thus, when the first jaw 1101 and the second jaw 1102 are rotated in directions close to each other (i.e., when the first jaw 1101 and the second jaw 1102 are closed), the grip force is greater in a direction in which the first jaw 1101 and the second jaw 1102 are closed. This will be described below in more detail.

As described above, in motions of the first jaw 1101 and the second jaw 1102 being opened and closed, there are two axes that become the center of rotation of the jaws. That is, the first jaw 1101 and the second jaw 1102 perform opening and closing motions around two axes of the rotation shaft 1141 and a shaft that is different from the rotation shaft 1141.

Meanwhile, although not shown in the drawings, in an optional embodiment, the first jaw 1101 and the second jaw 1102 may perform a motion around one rotation shaft, and for example, the jaw pulley rotation shaft and the jaw rotation shaft may be the same.

(Cartridge)

Hereinafter, the cartridge 1500 of the surgical instrument 1000 of FIG. 16 will be described in more detail.

Figure 24:
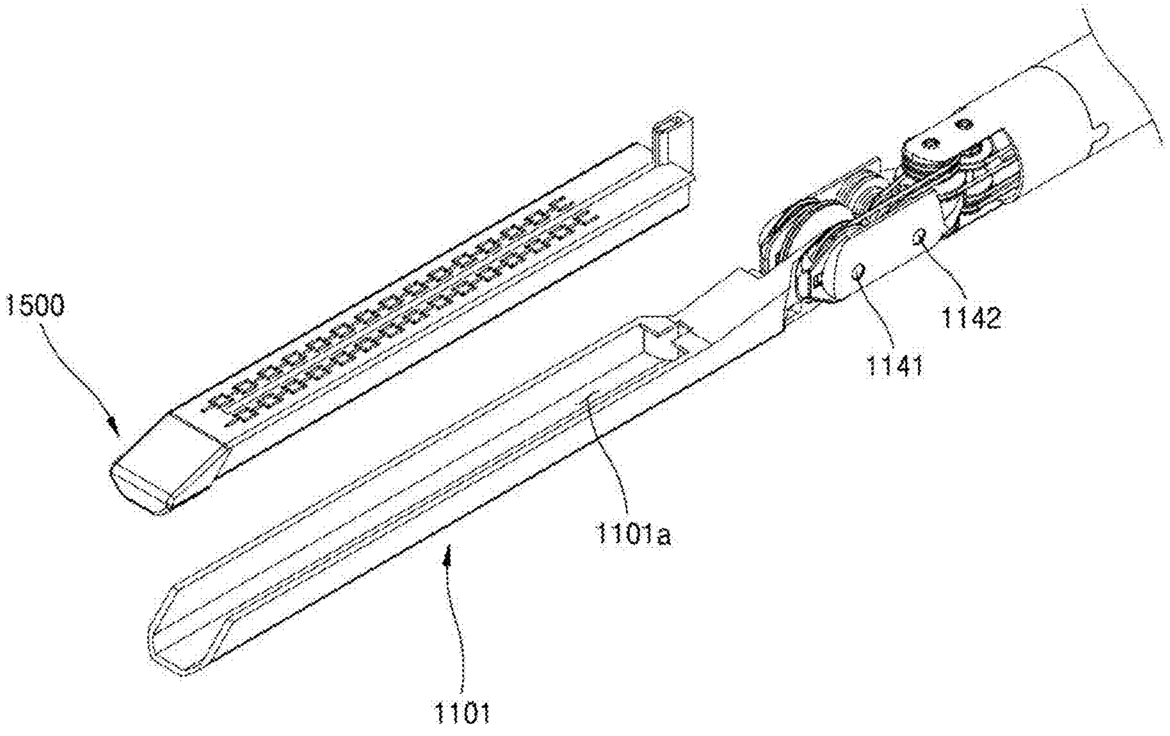
FIG. 24 is a perspective view illustrating the first jaw and a cartridge of the surgical instrument of FIG. 16.
Figure 25:
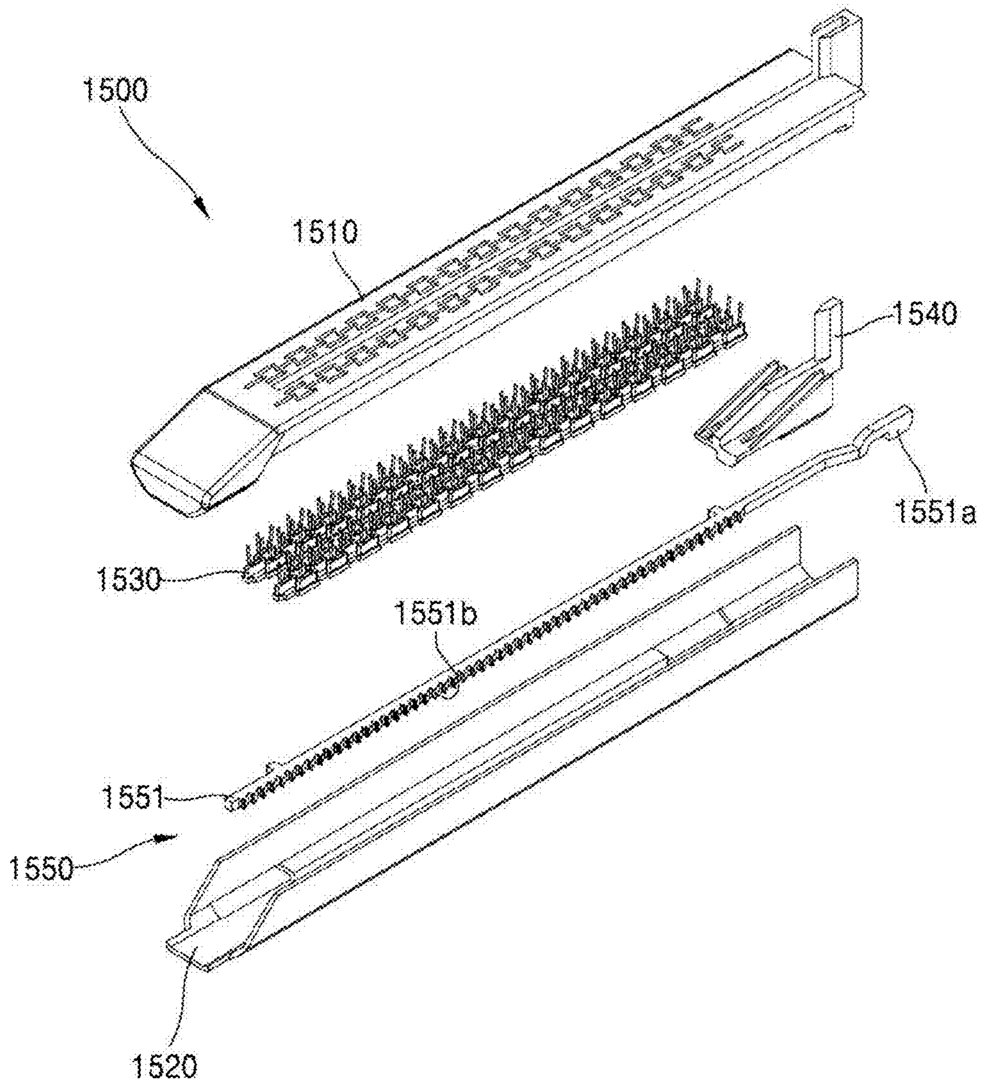
FIG. 25 is an exploded perspective view illustrating the cartridge of FIG. 24.
Figure 26:
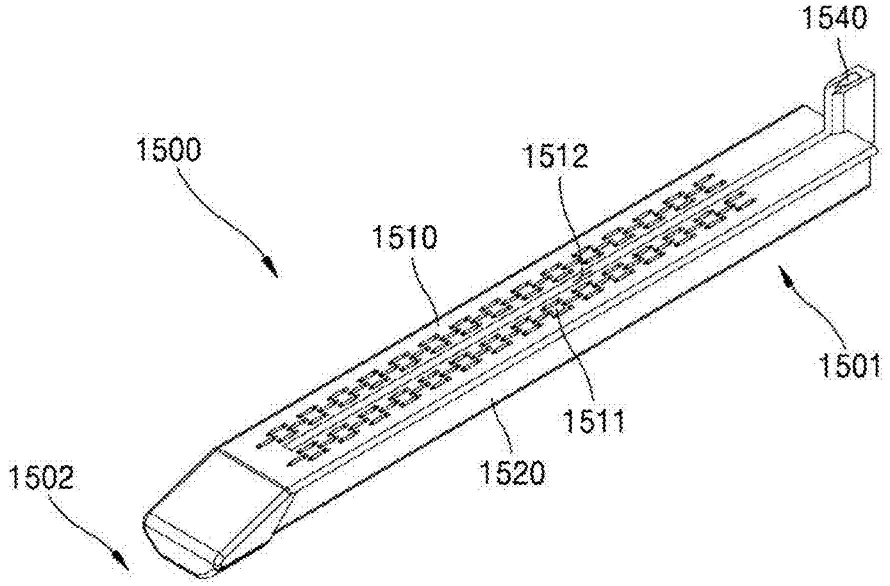
FIG. 26 is an assembled perspective view illustrating the cartridge of FIG. 24.
Figure 27:
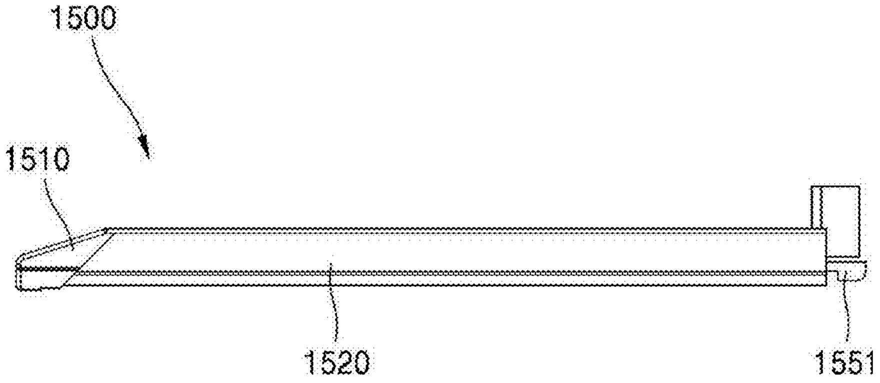
FIG. 27 is a side view illustrating the cartridge of FIG. 24.
Figure 28:
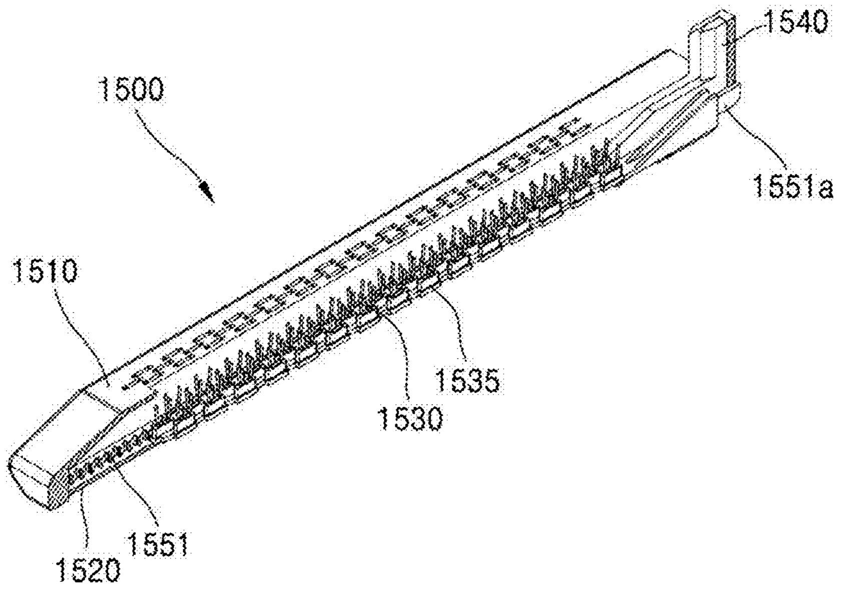
FIG. 28 is a perspective cross-sectional view illustrating the cartridge of FIG. 24.
Figure 29:
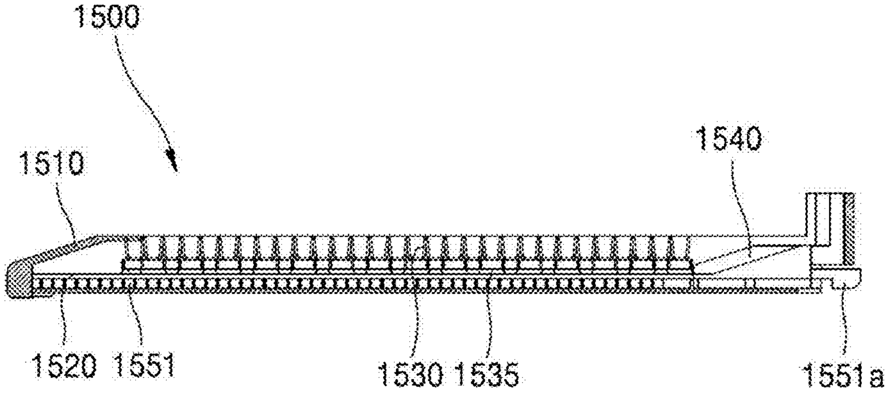
FIG. 29 is a side cross-sectional view illustrating the cartridge of FIG. 24.
Figure 30:
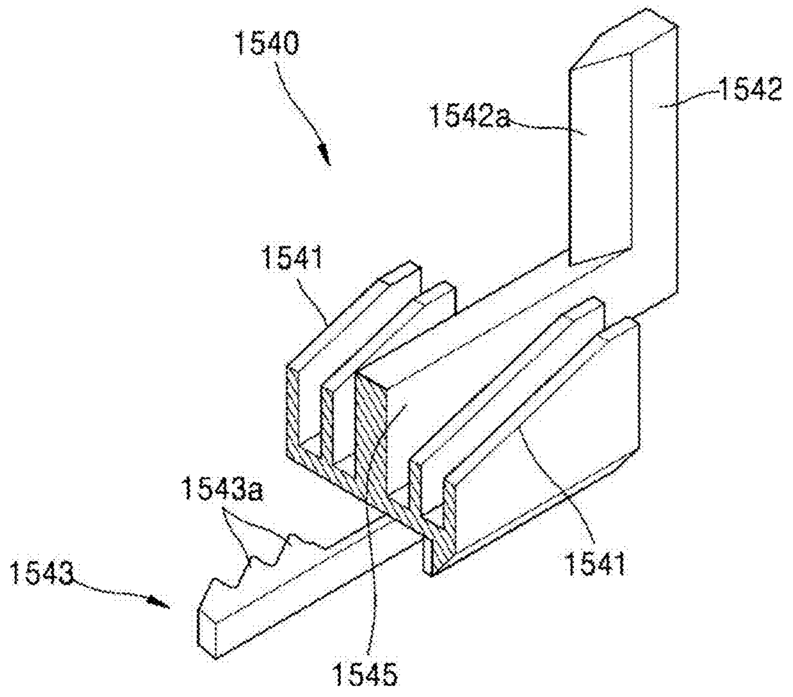
FIGS. 30 and 31 are perspective views illustrating an operation member of the cartridge of FIG. 24.
Figure 31:
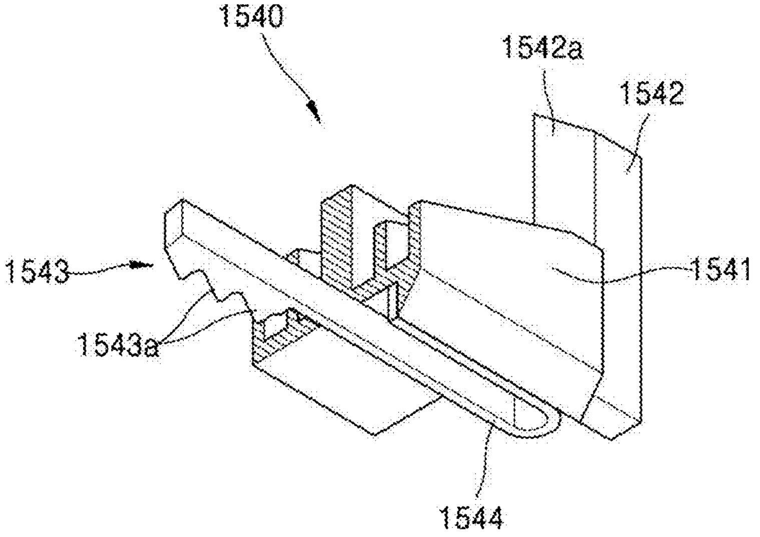
Figure 32:
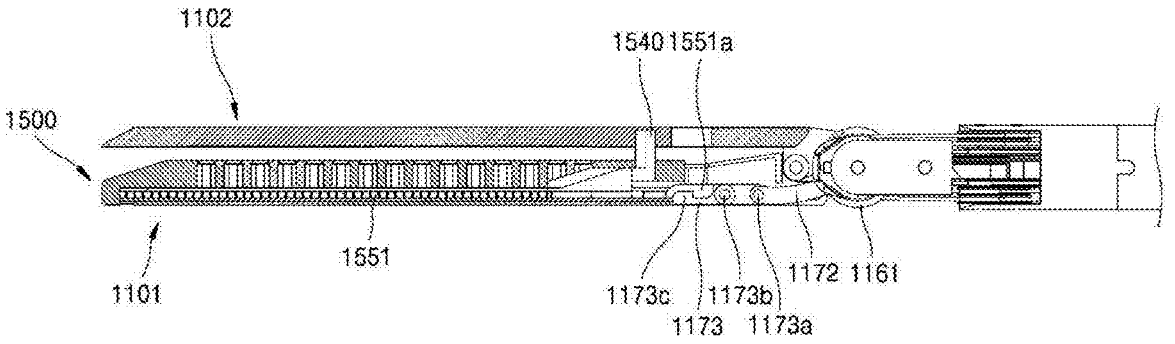
FIG. 32 is a side cross-sectional view illustrating a stapling-related structure of the end tool of the surgical instrument of FIG. 16.
Figure 33:
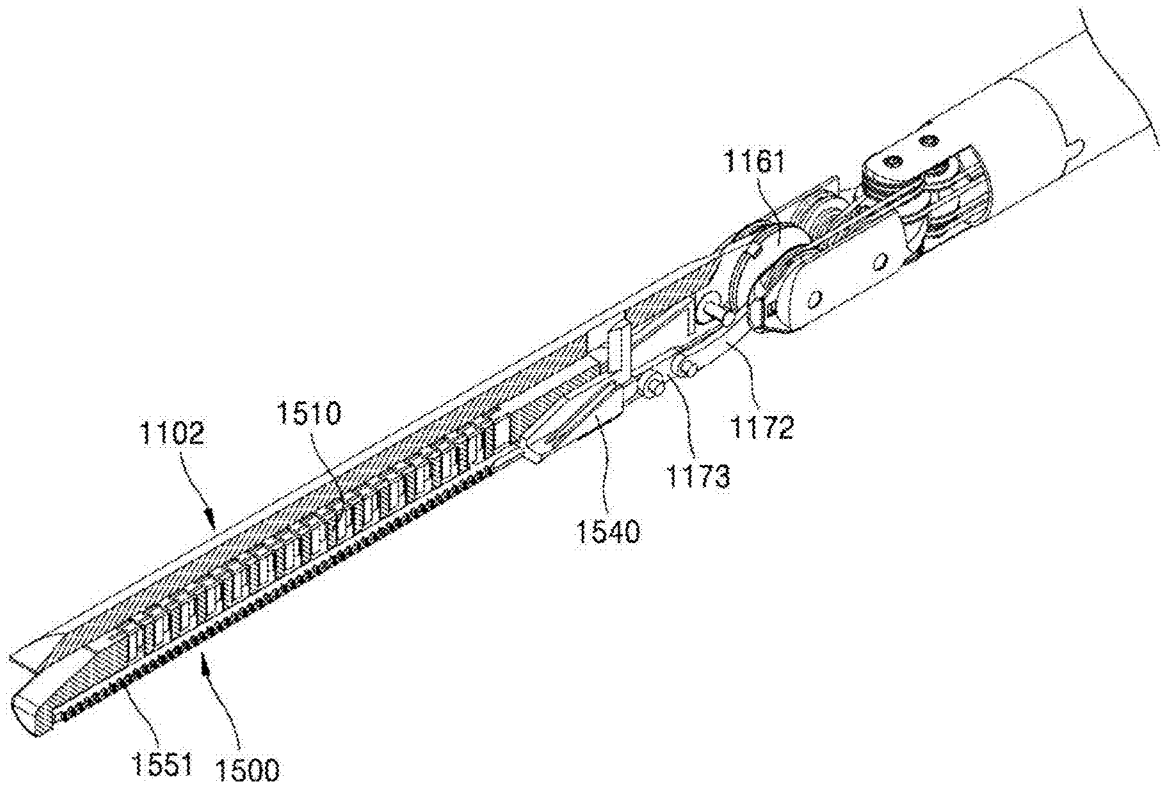
FIGS. 33 and 34 are perspective cross-sectional views illustrating a stapling structure of the end tool of the surgical instrument of FIG. 16.
Figure 34:
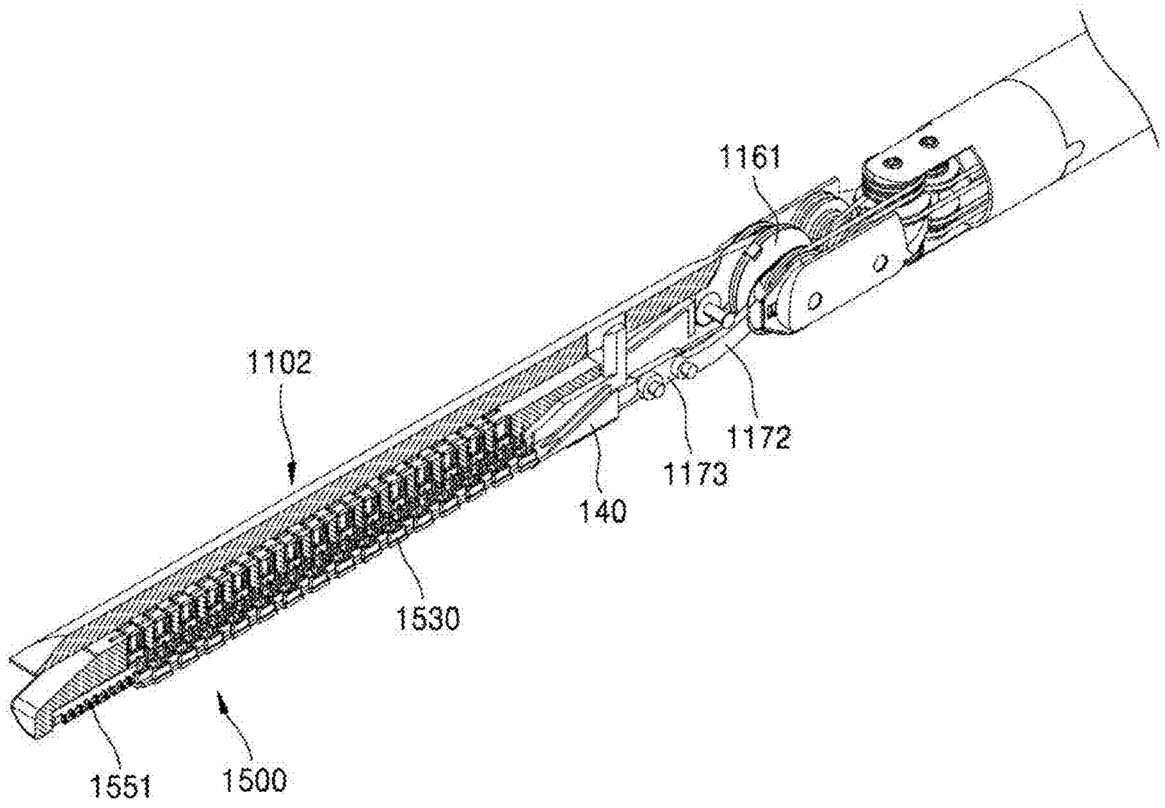
Figure 35:
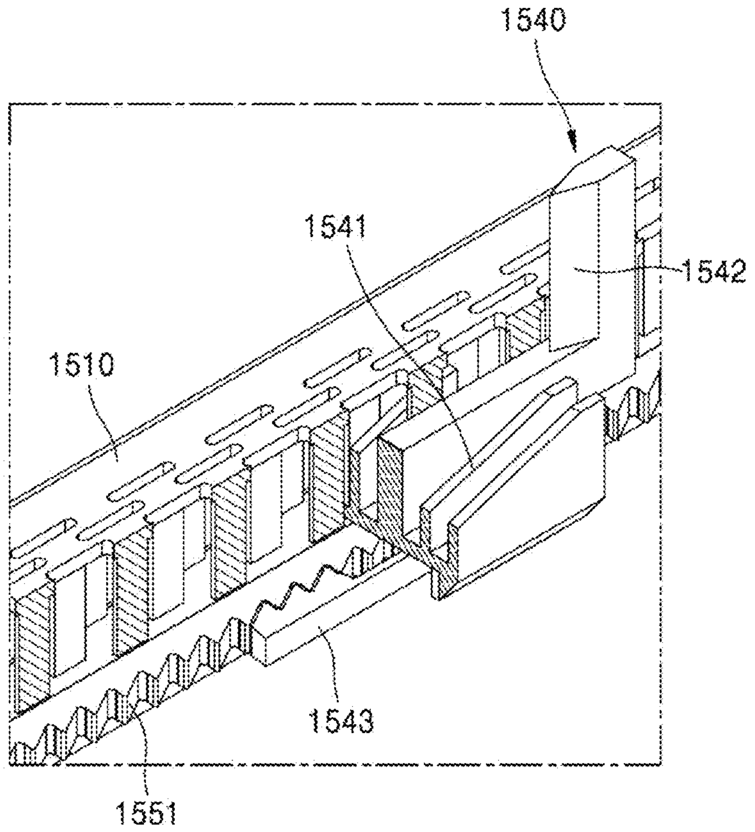
FIGS. 35 to 38 are perspective views illustrating a ratchet drive operation of the end tool of FIG. 33.
Figure 36:
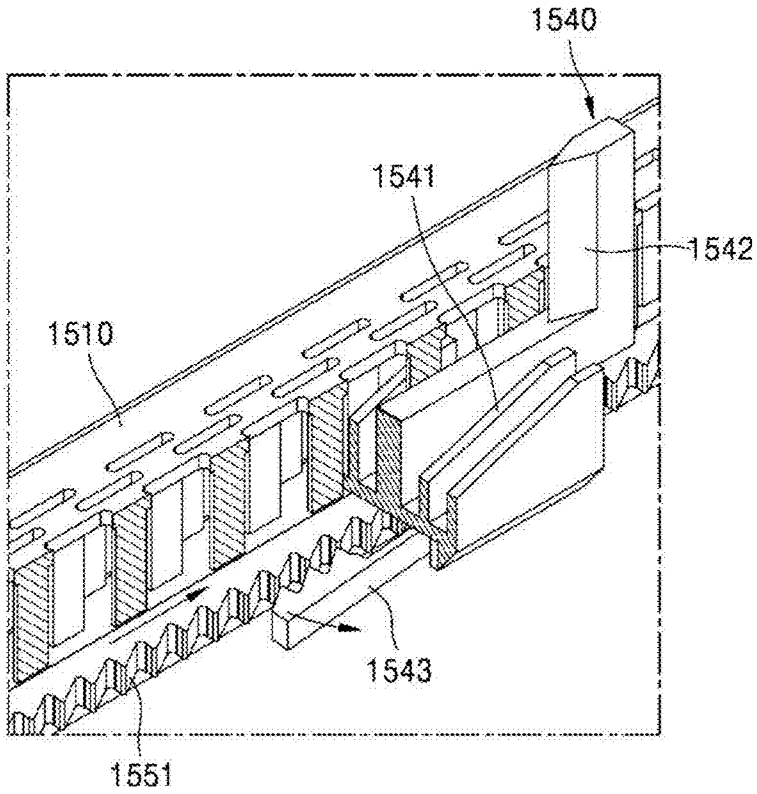

FIG. 24 is a perspective view illustrating the first jaw and the cartridge of the surgical instrument of FIG. 16. FIG. 25 is an exploded perspective view illustrating the cartridge of FIG. 24. FIG. 26 is an assembled perspective view illustrating the cartridge of FIG. 24. FIG. 27 is a side view illustrating the cartridge of FIG. 24. FIG. 28 is a perspective cross-sectional view illustrating the cartridge of FIG. 24. FIG. 29 is a side cross-sectional view illustrating the cartridge of FIG. 24. FIGS. 30 and 31 are perspective views illustrating the operation member of the cartridge of FIG. 24. FIG. 32 is a side cross-sectional view illustrating a stapling-related structure of the end tool of the surgical instrument of FIG. 16. FIGS. 33 and 34 are perspective cross-sectional views illustrating a stapling structure of the end tool of the surgical instrument of FIG. 16. FIGS. 35 to 38 are perspective views illustrating a ratchet drive operation of the end tool of FIG. 33. FIGS. 39 and 40 are plan views illustrating a ratchet drive operation of the end tool of FIG. 33. FIG. 41 is a cross-sectional view illustrating an entire stapling motion of the end tool of FIG. 33.

Referring to FIGS. 24 to 41 and the like, the cartridge 1500 is formed to be mountable to and dismountable from the first jaw 1101, and includes a plurality of staples 1530 and a blade 1542 therein to perform suturing and cutting tissue. Here, the cartridge 1500 may include a cover 1510, a housing 1520, the staples 1530, withdrawal members 1535, the operation member 1540, and the reciprocating assembly 1550.

The housing 1520 forms an outer shape of the cartridge 1500, and may be formed entirely in the form of a hollow box with one surface (upper surface) thereof is removed to accommodate the reciprocating assembly 1550, the operation member 1540, and the staple 1530 therein. Here, the housing 1520 may be formed in an approximately "U" shape in cross section.

The cover 1510 is formed to cover an upper portion of the housing 1520. Staple holes 1511 through which the plurality of staples 1530 may be ejected to the outside may be formed in the cover 1510. As the staples 1530, which are accommodated inside the housing 1520 before a stapling operation, are pushed and raised upward by the operation member 1540 during a stapling motion, and pass through the staple holes 1511 of the cover 1510 to be withdrawn to the outside of the cartridge 1500, stapling is performed.

Meanwhile, a slit 1512 may be formed in the cover 1510 along a length direction of the cover 1510. The blade 1542 of the operation member 1540 may protrude out of the cartridge 1500 through the slit 1512. As the blade 1542 of the operation member 1540 passes along the slit 1512, staple-completed tissue may be cut.

The plurality of staples 1530 may be disposed inside the housing 1520. As the operation member 1540, which will be described later, is linearly moved in one direction, the plurality of staples 1530 are sequentially pushed and raised from the inside of the housing 1520 to the outside, thereby performing suturing, that is, stapling. Here, the staples 1530 may be made of a material that may include titanium, stainless steel, or the like.

Meanwhile, the withdrawal member 1535 may be further disposed between the housing 1520 and the staple 1530. In other words, it may be said that the staple 1530 is disposed above the withdrawal member 1535. In this case, the operation member 1540 is linearly moved in one direction to push and raise the withdrawal member 1535, and the withdrawal member 1535 may push and raise the staple 1530.

As such, the operation member 1540 may be described as pushing and raising the staples 1530 in both the case in which the operation member 1540 directly pushes and raises the staples 1530 and the case in which the operation member 1540 pushes and raises the withdrawal members 1535 and the withdrawal members 1535 pushes and raises the staples 1530 (i.e., the operation member 1540 indirectly pushes and raises the staples 1530).

The reciprocating assembly 1550 may be disposed at an inner lower side of the housing 1520. The reciprocating assembly 1550 may include one or more reciprocating member 1551. In the present embodiment, it is illustrated that one reciprocating member 1551 is provided, but in embodiments to be described later, a plurality of reciprocating members 1551 may be provided.

In the present embodiment, the reciprocating member 1551 may be a rack. The reciprocating member 1551 may include recesses 1551*b* and the coupling part 1551*a*. In detail, the reciprocating member 1551 may be formed in the form of an elongated bar, and a plurality of recesses 1551*b* having a sawtooth shape may be formed on one surface thereof. The recess 1551*b* may be formed to be in contact with the operation member 1540 to be described later, in particular, a ratchet member 1543 of the operation member 1540. In other words, the reciprocating member 1551 may include the plurality of recesses 1551*b* shaped to engage with ratchets 1543*a* of the ratchet member 1543.

Meanwhile, although not shown in the drawings, in addition to a rack shape, the reciprocating member 1551 may be provided as various shapes of members, which are directly or indirectly connected to the staple pulley 1161 and may perform a linear reciprocating motion in response to a rotational motion of the staple pulley 1161. For example, the reciprocating member 1551 may be in the form of a clutch in which recesses are not present.

Here, the reciprocating member 1551 is not fixedly coupled to the other components of the cartridge 1500, and may be formed to be movable relative to the other components of the cartridge 1500. That is, the reciprocating member 1551 may perform a reciprocating linear motion with respect to the housing 1520 and the cover 1510 coupled to the housing 1520.

Meanwhile, in the reciprocating member 1551, the coupling part 1551*a* may be formed at a proximal end 1501 side adjacent to the pulley 1111, and the coupling part 1551*a* may be fastened and coupled to the staple link assembly 1170 of the end tool 1100. Thus, when the staple link assembly 1170 performs a reciprocating linear motion in the extension direction (i.e., the Y-axis direction) of the connection part 1400, the reciprocating member 1551 coupled thereto may also perform a reciprocating linear motion in the extension direction (i.e., the Y-axis direction) of the connection part 1400. This will be described in more detail later.

The operation member 1540 may be disposed inside the housing 1520. The operation member 1540 is formed to be in contact with the reciprocating member 1551, and may be formed to linearly move in one direction in response to a reciprocating linear motion of the reciprocating member 1551. In other words, the operation member 1540 interacts with the reciprocating member 1551 to perform stapling and cutting motions while moving in the extension direction of the connection part 1400.

The operation member 1540 may include a wedge 1541, the blade 1542, the ratchet member 1543, an elastic member 1544, and a body 1545.

The body 1545 may be formed in the shape of an elongated square column, and forms a base of the operation member 1540.

The wedge 1541 is formed on at least one side of the body 1545, and may be formed to have a predetermined inclined surface. That is, the wedge 1541 may be formed to be inclined to a certain extent in the extension direction of the connection part 1400. In other words, the wedge 1541 may be formed to have a greater height at a proximal end 1501 side of the cartridge 1500 than a distal end 1502 side of the cartridge 1500. In the drawing, it is illustrated that two wedges 1541 are formed on each side of the body 1545, but the concept of the present disclosure is not limited thereto, and the wedge 1541 may be formed in various numbers and shapes depending on the shape of the staple 1530 or the withdrawal member 1535 that is in contact with the wedge 1541.

The wedge 1541 may be formed to be in contact with the withdrawal members 1535 or the plurality of staples 1530 in turn and may serve to sequentially push and raise the staples 1530. As shown in FIG. 41 to be described later and elsewhere herein, the operation member 1540 may serve to withdraw the staples 1530 to the outside of the cartridge 1500 by sequentially pushing and raising the staples 1530 while moving toward the distal end 1502.

The blade 1542 may be formed at one side of the wedge 1541, more specifically, at one side of the wedge 1541 at the proximal end 1501 side. An edge 1542*a* formed to be sharp to cut tissue is formed in one region of the blade 1542. As at least a portion of the edge 1542*a* is withdrawn to the outside of the first jaw 1101 and the cartridge 1500, tissue disposed between the first jaw 1101 and the second jaw 1102 may be cut. The edge 1542*a* of the blade 1542 may be always withdrawn to the outside of the first jaw 1101. Alternatively, the edge 1542*a* of the blade 1542 may normally be accommodated inside the first jaw 1101 or inside the cartridge 1500, and may be withdrawn to the outside of the first jaw 1101 only when the operation member 1540 is moved in a length direction.

The ratchet member 1543 is formed on one side of the wedge 1541, more specifically, below wedge 1541, and may be formed to face the reciprocating member 1551 to be described later. The ratchet member 1543 may be formed in the form of a bar and may include a plurality of ratchets 1543*a* on one surface. The operation member 1540 is moved only in one direction (i.e., toward the distal end) with respect to the reciprocating member 1551 by the ratchet member 1543. The ratchets 1543*a* of the ratchet member 1543 may be formed to be in contact with the recess 1551*b* of the reciprocating member 1551 described above.

The elastic member 1544 is formed on one side of the body 1545 or the wedge 1541 and serves to apply a predetermined elastic force to the ratchet member 1543. In an example, one region of the elastic member 1544 may be connected to the wedge 1541 or the body 1545, and another region of the elastic member 1544 may be connected to the ratchet member 1543, so that the elastic member 1544 may connect the wedge 1541 or the body 1545 to the ratchet member 1543. Here, the elastic member 1544 may apply an elastic force in a direction in which the ratchet member 1543 comes into close contact with the reciprocating member 1551. To this end, the elastic member 1544 may be formed in the form of a leaf spring, and may be provided in various forms capable of providing a predetermined elastic force to the ratchet member 1543, such as a coil spring, a dish spring, and the like.

Here, the ratchet 1543*a* of the ratchet member 1543 may be formed such that a first surface 1543*a*1 (specifically, at the distal end 1502 side) is formed to have a gentle slope with a predetermined angle, and a second surface 1543*a*2 (specifically, at the proximal end 1501 side) is formed to be vertical or near vertical.

In addition, in order to be engaged with the ratchet 1543*a* of the ratchet member 1543, the recess 1551*b* of the reciprocating member 1551 may also be formed such that a first surface 1551*b*1 (specifically, at the proximal end 1501 side) is formed to have a gentle slope with a predetermined angle, and a second surface 1551*b*2 (specifically, at the distal end 1502 side) is formed to be vertical or near vertical.

In a state in which the reciprocating member 1551 and the ratchet member 1543 are coupled to each other (or engaged or in close contact with each other), the inclined first surface 1543*a*1 of the ratchet 1543*a* and the inclined first surface 1551*b*1 of the recess 1551*b* may be disposed to face each other (that is, in contact with each other). In addition, the vertically formed second surface 1543*a*2 of the ratchet 1543*a* and the vertically formed second surface 1551*b*2 of the recess 1551*b* may be disposed to face each other (i.e., in contact with each other).

With this configuration, in a state in which the ratchet 1543*a* and the recess 1551*b* are coupled to (or engaged with) each other, the ratchet 1543*a* and the recess 1551*b* may be allowed to move only in one direction, acting as a kind of ratchet.

In an example, when it is assumed that the reciprocating member 1551 is in a fixed state, the operation member 1540 is movable in a direction in which the second surface 1543*a*2 and the second surface 1551*b*2, which are vertically formed, are away from each other, but when the second surface 1543*a*2 and the second surface 1551*b*2 are in contact with each other, the operation member 1540 is not movable in a direction in which the second surface 1543*a*2 and the second surface 1551*b*2 are closer to each other.

From another perspective, when the reciprocating member 1551 is moved toward the distal end 1502 in a state in which the reciprocating member 1551 and the ratchet member 1543 are coupled to each other (or engaged or in close contact with each other), the ratchet member 1543 is moved together toward the distal end 1502 by the reciprocating member 1551. That is, the vertically formed second surface 1551*b*2 of the reciprocating member 1551 pushes the vertically formed second surface 1543*a*2 of the operation member 1540 such that the ratchet member 1543 is moved together toward the distal end 1502 by the reciprocating member 1551.

In contrast, when the reciprocating member 1551 is moved toward the proximal end 1501 in a state in which the reciprocating member 1551 and the ratchet member 1543 are coupled to each other (or engaged or in close contact with each other), only the reciprocating member 1551 is moved alone toward the proximal end 1501 while the ratchet member 1543 a fixed. That is, the inclined first surface 1551*b*1 of the reciprocating member 1551 is moved along the inclined first surface 1543*a*1 of the operation member 1540 in a state in which the operation member 1540 is fixed, so that only the reciprocating member 1551 is moved alone toward the proximal end 1501.

Figure 37:
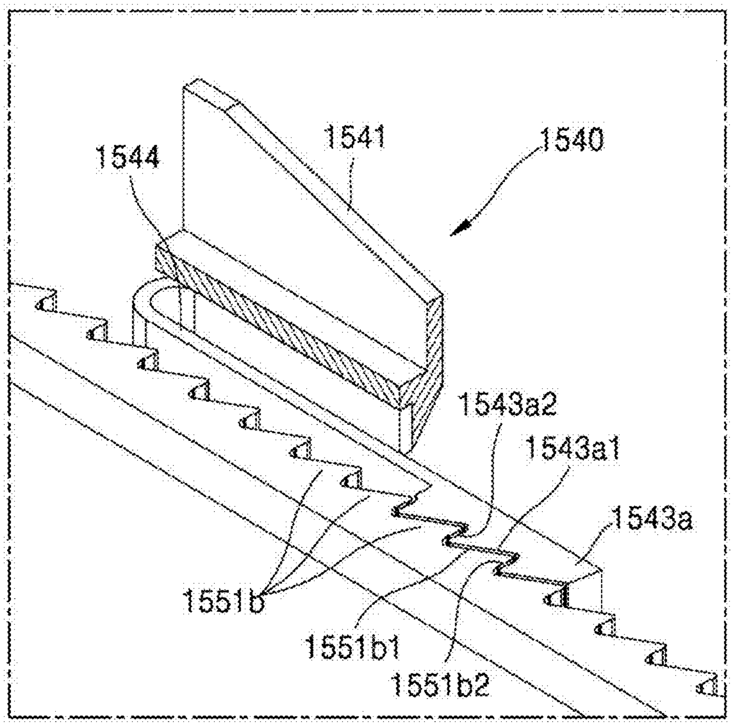
Figure 38:
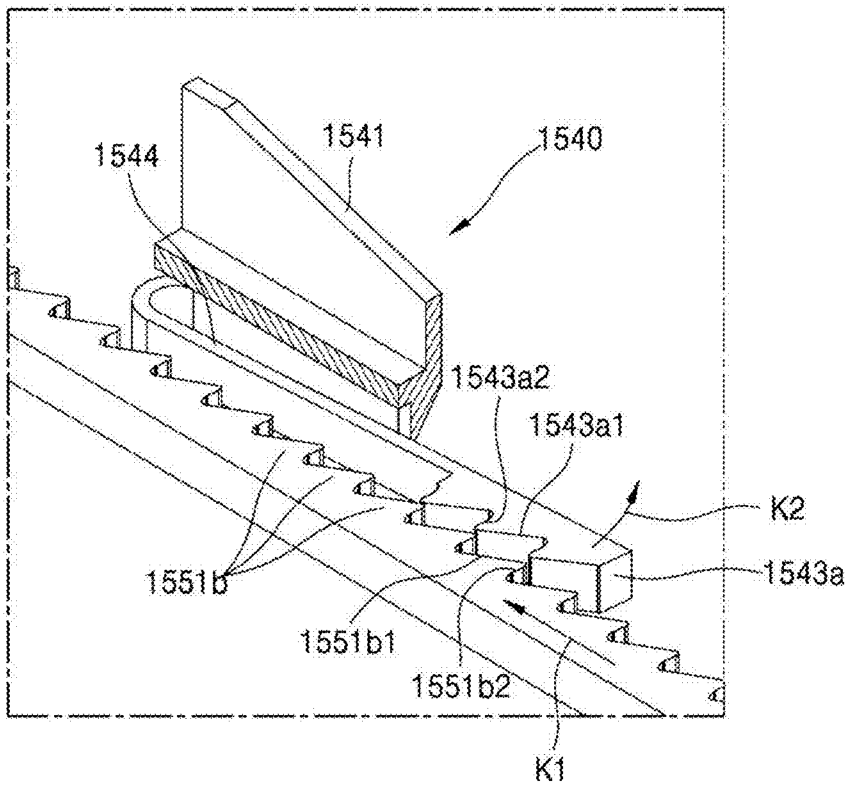
Figure 39:
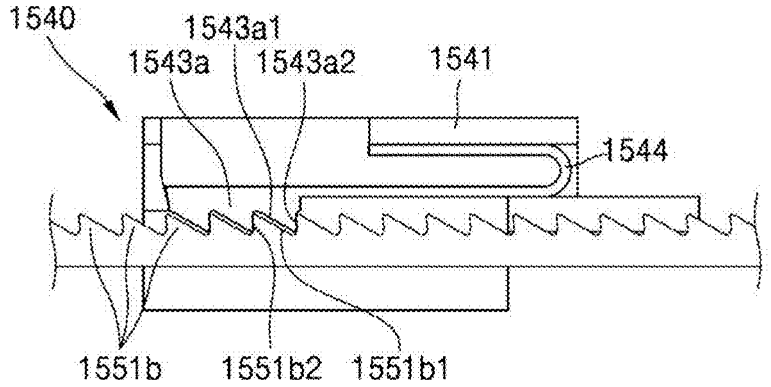
FIGS. 39 and 40 are plan views illustrating a ratchet drive operation of the end tool of FIG. 33.
Figure 40:
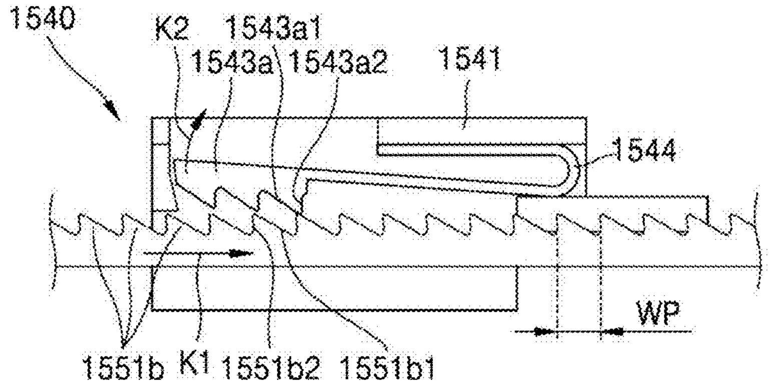
Figure 41:
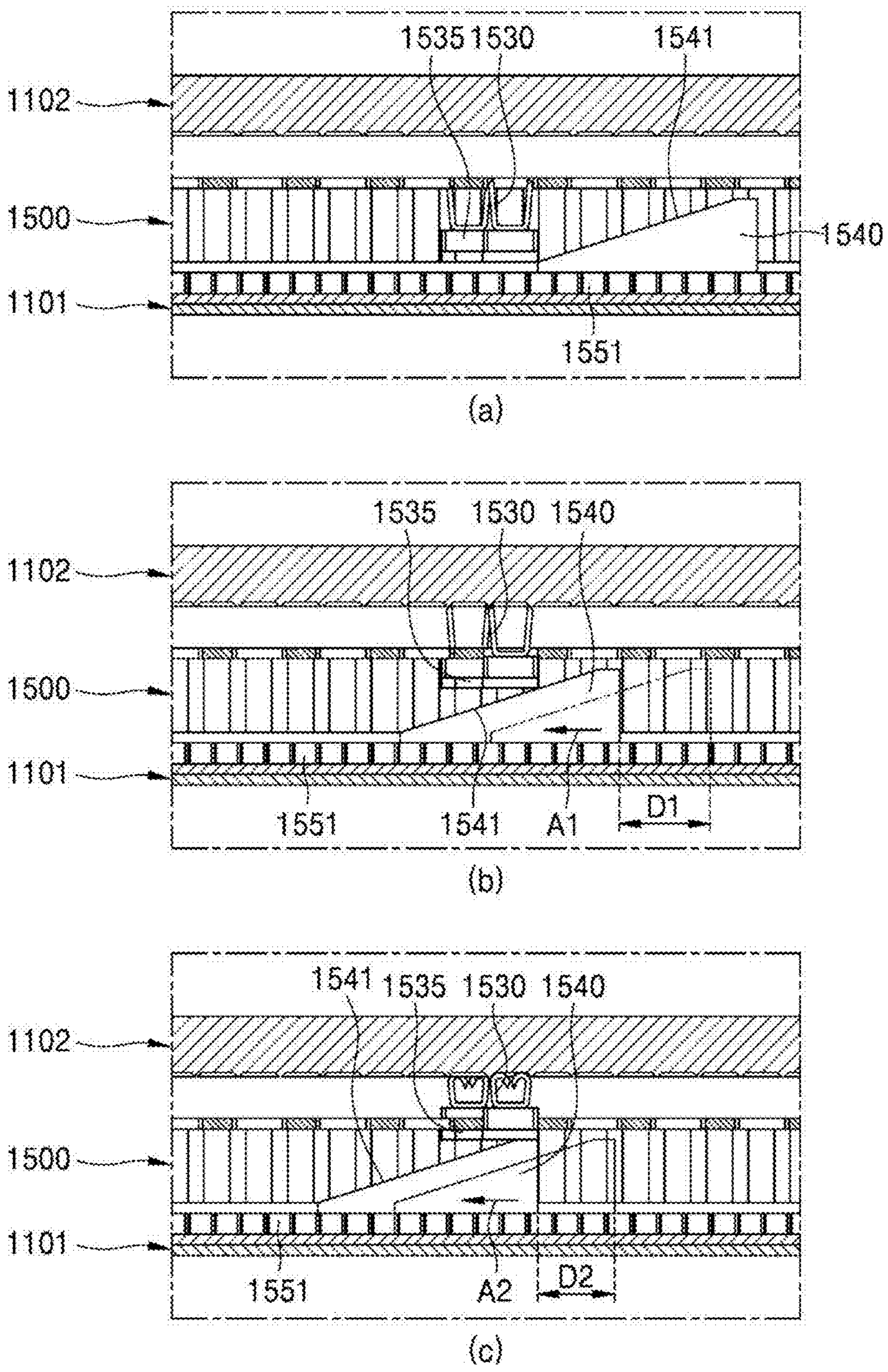
FIG. 41 is a cross-sectional view illustrating an entire stapling motion of the end tool of FIG. 33.

Referring to FIGS. 37 to 40, when the reciprocating member 1551 is moved toward (in the direction of an arrow K1 of FIGS. 38 and 40) of the proximal end 1501 in the state as shown in FIGS. 37 and 39, as the inclined first surface 1551*b*1 of the reciprocating member 1551 is moved along the inclined first surface 1543*a*1 of the operation member 1540, the ratchet member 1543 is pushed as a whole in the direction of an arrow K2 of FIG. 38. In addition, at this time, the elastic member 1544 is elastically deformed to a certain extent.

In this state, when the reciprocating member 1551 is further moved toward the proximal end 1501, and the inclined first surface 1551*b*1 of the reciprocating member 1551 is moved beyond an end of the inclined first surface 1543*a*1 of the operation member 1540, the recess 1551*b* of the reciprocating member 1551 meets the next ratchet 1543*a* of the ratchet member 1543. In this case, since the elastic member 1544 applies an elastic force in a direction in which the ratchet member 1543 comes into close contact with the reciprocating member 1551, front surfaces of the reciprocating member 1551 and the ratchet member 1543 are brought into close contact with each other again.

The cartridge 1500 is accommodated in the cartridge accommodation part 1101*a* of the first jaw 1101, and in this case, the reciprocating member 1551 of the cartridge 1500 is coupled to the staple link assembly 1170 of the end tool 1100. Accordingly, the rotational motion of the staple pulley 1161 of the end tool 1100 is converted into a linear motion of the reciprocating member 1551 through the staple link assembly 1170.

In this case, when the coupling part 1551*a* of the reciprocating member 1551 is connected to the staple pulley 1161 through the staple link assembly 1170, and the staple pulley 1161 is rotated alternately in the clockwise/counterclockwise directions, the reciprocating member 1551 may be repeatedly moved forward and backward. In addition, when the reciprocating member 1551 is moved forward, the operation member 1540 may be moved forward together with the reciprocating member 1551, and when the reciprocating member 1551 is moved backward, only the reciprocating member 1551 may be moved backward and the operation member 1540 may remain stationary in place. As the operation member 1540 is moved forward while repeating this process, the staple 1530 may be stapled by the wedge 1541 while the blade 1542 cuts stapled tissue.

This will be described in more detail as follows.

(Stapling and Cutting Motions)

When the driving force is transmitted to the staple pulley 1161 through the driving transmission part such as a wire by the driving part MTU, the staple pulley 1161 is rotated in one of the clockwise direction and the counterclockwise direction, and the staple link assembly 1170 connected to the staple pulley 1161 and the reciprocating assembly 1550 of the cartridge 1500 connected to the staple link assembly 1170 are moved toward the distal end 1502 of the cartridge 1500.

In addition, when the reciprocating assembly 1550 is moved toward the distal end 1502 of the cartridge 1500, the operation member 1540 in contact with the reciprocating assembly 1550 is moved toward the distal end 1502 of the cartridge 1500 together with the reciprocating assembly 1550.

In addition, as the operation member 1540 is moved toward the distal end 1502 of the cartridge 1500, the blade 1542 of the operation member 1540 is moved toward the distal end 1502 of the cartridge 1500 while the operation member 1540 ejects the staples 1530 out of the cartridge 1500.

Meanwhile, when the staple pulley 1161 is rotated in the other one of the clockwise direction and the counterclockwise direction, the staple link assembly 1170 connected to the staple pulley 1161 and the reciprocating assembly 1550 of the cartridge 1500 connected to the staple link assembly 1170 are moved toward the proximal end 1501 of the cartridge 1500, and in this case, the operation member 1540 is stationary.

In addition, as the above-described operations are repeatedly performed, a stapling motion by the wedge 1541 and a cutting motion by the blade 1542 are simultaneously performed.

FIG. 41 is a cross-sectional view illustrating an entire stapling motion of the end tool of FIG. 33.

Referring to FIG. 41, in the state as shown in FIG. 41A, as the operation member 1540 is moved in the direction of an arrow A1 of FIG. 41B, the wedge 1541 of the operation member 1540 pushes and raises the withdrawal member 1535, and the withdrawal member 1535 pushes and raises one side of a lower portion of the staple 1530. In addition, due thereto, the staple 1530 is ejected to the outside of the first jaw 1101 and the cartridge 1500.

In this state, when the operation member 1540 is further moved in the direction of an arrow A2 of FIG. 41C, the ejected staple 1530 is continuously pushed and raised by the operation member 1540 while in contact with the anvil 1102*a* of the second jaw 1102, so that stapling is performed while both end portions of the staple 1530 are bent.

As such motions are continuously performed, stapling is sequentially performed in the plurality of staples 1530 from the staple 1530 at the proximal end 1501 side to the staple 1530 at the distal end 1502 side.

At this time, information on the driving force transmitted by the driving part MTU to the reciprocating assembly 1550 may be determined by measuring driving information of the driving part MTU, such as a rotation amount of the motor member, through the detection member 1130. As a specific example, through information on forward and backward movements of the reciprocating members 1551, the number of forward and backward movements of the reciprocating assembly 1550, and the position information of the reciprocating assembly 1550 according thereto may be determined. Accordingly, information on the driving force transmitted to the operation member 1540 and information on a moving distance and position of the operation member 1540 may be easily determined. Accordingly, the stapling step can be precisely controlled by identifying the position state of the operation member 1540 during the stapling.

(Correlation Between Stapling and Cutting Motions and Other Motions)

Hereinafter, a correlation between stapling and cutting motions and other motions (pitch, yaw, and actuation motions) will be described.

First, when the end tool 1100 performs a pitch motion, the staple pulley 1161 also performs a pitch motion. That is, when the pulley 1111 and the pulley 1121 perform pitch motions of being rotated in the same direction around the rotation shaft 1143, the staple pulley 1161 should also be rotated in the same direction as the pulley 1111 and the pulley 1121. If the staple pulley 1161 is not rotated together with the pulley 1111 and the pulley 1121 when the pulley 1111 and the pulley 1121 are rotated around the rotation shaft 1143, there is a risk that the cartridge 1500 connected to the staple pulley 1161 is moved relative to the first jaw 1101 and is disconnected from the first jaw 1101. Further, rotation of the staple pulley 1161 that is not synchronized with that of the pulley 1111 may cause the reciprocating member 1551 to unintentionally move forward, which in turn may cause an unintended stapling motion.

Next, when the end tool 1100 performs a yaw motion, the staple pulley 1161 also performs a yaw motion. That is, when the pulley 1111 and the pulley 1121 perform yaw motions of being rotated in the same direction around the rotation shaft 1141, the staple pulley 1161 should also be rotated in the same direction as the pulley 1111 and the pulley 1121. If the staple pulley 1161 is not rotated together with the pulley 1111 and the pulley 1121 when the pulley 1111 and the pulley 1121 are rotated around the rotation shaft 1141, there is a risk that the cartridge 1500 connected to the staple pulley 1161 is moved relative to the first jaw 1101 and is disconnected from the first jaw 1101. Further, rotation of the staple pulley 1161 that is not synchronized with that of the pulley 1111 may cause the reciprocating member 1551 to unintentionally move forward, which in turn may cause an unintended stapling motion.

Next, when the end tool 1100 performs an actuation motion, the staple pulley 1161 is rotated together with the pulley 1111. That is, when the pulley 1111 and the pulley 1121 perform actuation motions of being rotated the opposite directions around the rotation shaft 1141, the staple pulley 1161 should be rotated in the same direction as the pulley 1111. If the staple pulley 1161 is not rotated together with the pulley 1111 when the pulley 1111 is rotated around the rotation shaft 1143, there is a risk that the cartridge 1500 connected to the staple pulley 1161 is moved relative to the first jaw 1101 and is disconnected from the first jaw 1101. Further, rotation of the staple pulley 1161 that is not synchronized with that of the pulley 1111 may cause the reciprocating member 1551 to unintentionally move forward, which in turn may cause an unintended stapling motion.

Meanwhile, when the end tool 1100 performs stapling and cutting motions, the pulley 1111 and the pulley 1121 are not rotated. That is, when the staple pulley 1161 is rotated around the rotation shaft 1141 and the reciprocating member 1551 of the link member 1171 and the cartridge 1500 connected thereto performs a linear reciprocating motion, the pulley 1111 and the pulley 1121 should not be rotated. Otherwise, the first jaw 1101 or the second jaw 1102 is rotated during the stapling and cutting motion, and the stapling and cutting motions will not be performed normally.

As a result, when the pulley 1111, which is a first jaw pulley, is rotated, the staple pulley 1161 accommodated in the first jaw 1101 should be also rotated together with the pulley 1111. On the other hand, when the staple pulley 1161 is rotated for the stapling and cutting motions, the pulley 1111 and the pulley 1121 should be formed to maintain positions thereof without rotating. As such, the correlation between the stapling and cutting motions and other motions (the yaw and actuation motions) has been discussed above.

In other words, the pulley 1111 and the pulley 1121 may be said to be independent of the rotation of the staple pulley 1161. That is, even when the staple pulley 1161 is rotated by the staple wire, the pulley 1111 and the pulley 1121 may not be rotated. In contrast, the staple pulley 1161 may be said to be dependent of the rotation of the pulley 1111. That is, when the pulley 1111 is rotated by the jaw wire, the staple pulley 1161 may be formed to be rotated together with the pulley 1111.

Figure 42:
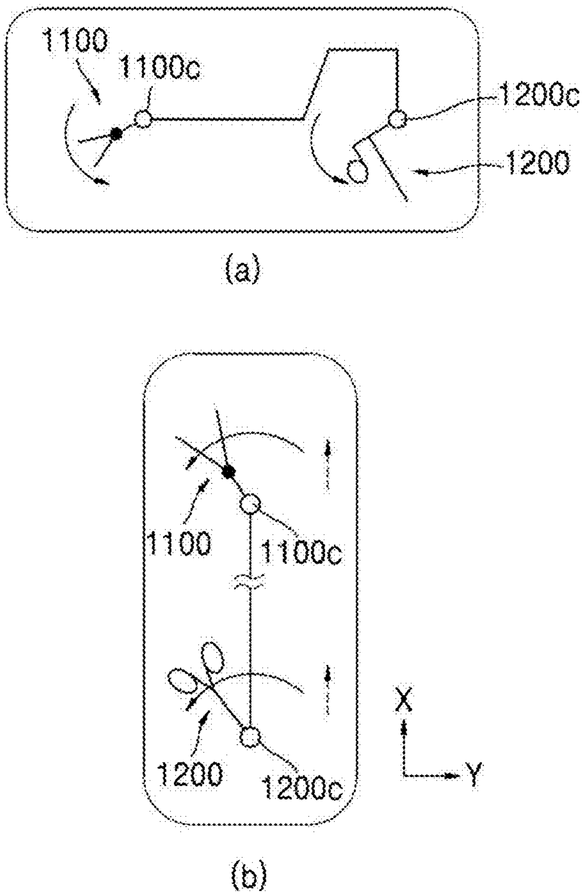
FIG. 42 is a diagram for schematically describing the concept of an operation of the surgical instrument of FIG. 16.

FIG. 42 is a diagram for schematically describing the operation concept of the surgical instrument of FIG. 16.

Specifically, referring to FIGS. 42A and 42B, in the surgical instrument of the present embodiment, the end tool 1100 is formed in front of a rotation center 1100*c* of the end tool, and the manipulation part 1200 is also formed in front of a rotation center 1200*c* of the manipulation part so that motions of the manipulation part 1200 and the end tool 1100 are intuitively matched. In other words, in the surgical instrument according to an embodiment of the present disclosure, at least a portion of the manipulation part may become closer to the end tool than the joint of the manipulation part in more than one moments during a manipulation process.

FIGS. 43 to 46 are perspective views illustrating a pitch motion of the surgical instrument of FIG. 16.

Figure 43:
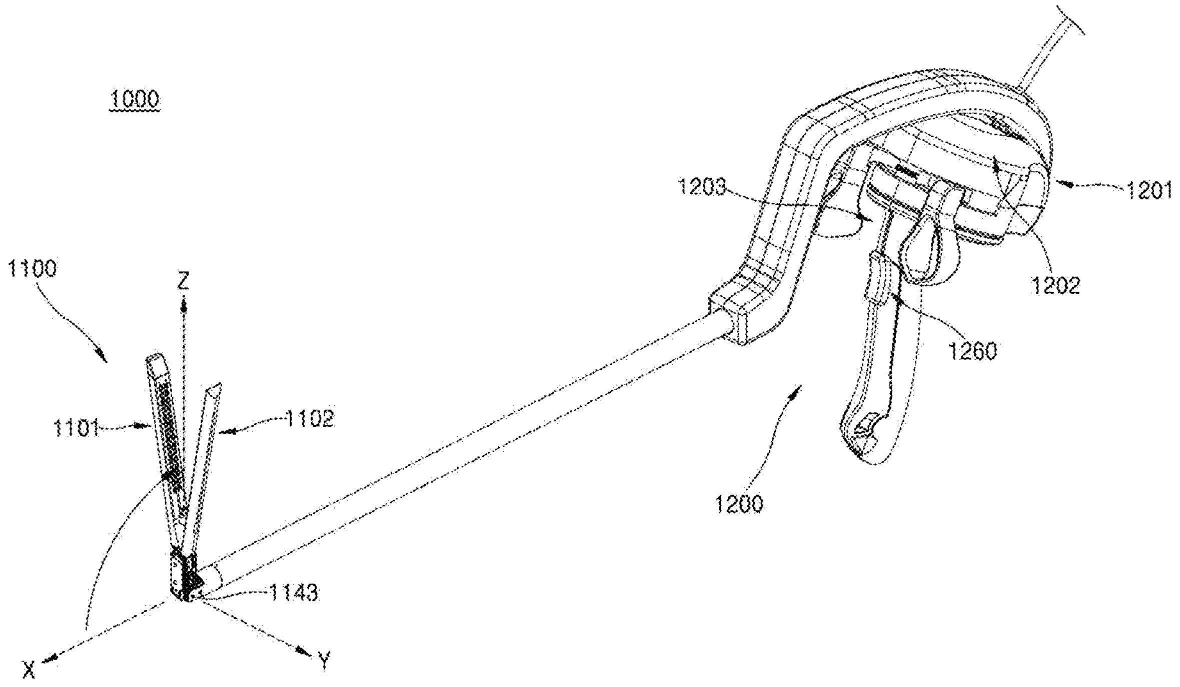
FIGS. 43 to 46 are perspective views illustrating a pitch motion of the surgical instrument of FIG. 16.
Figure 44:
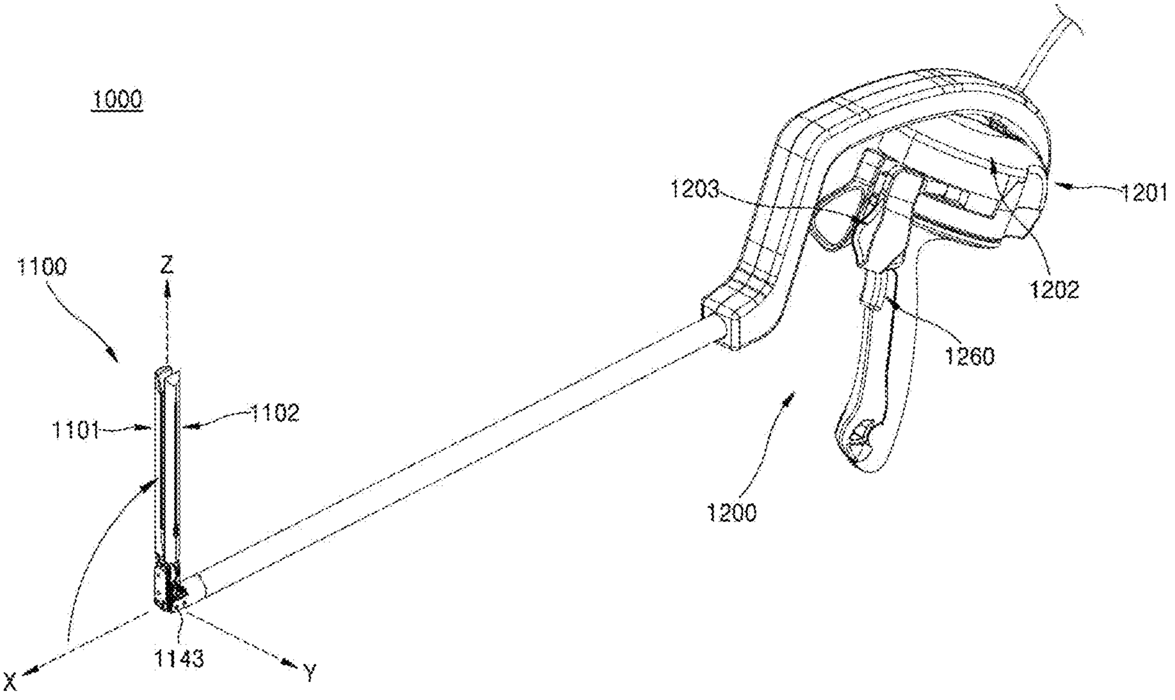
Figure 45:
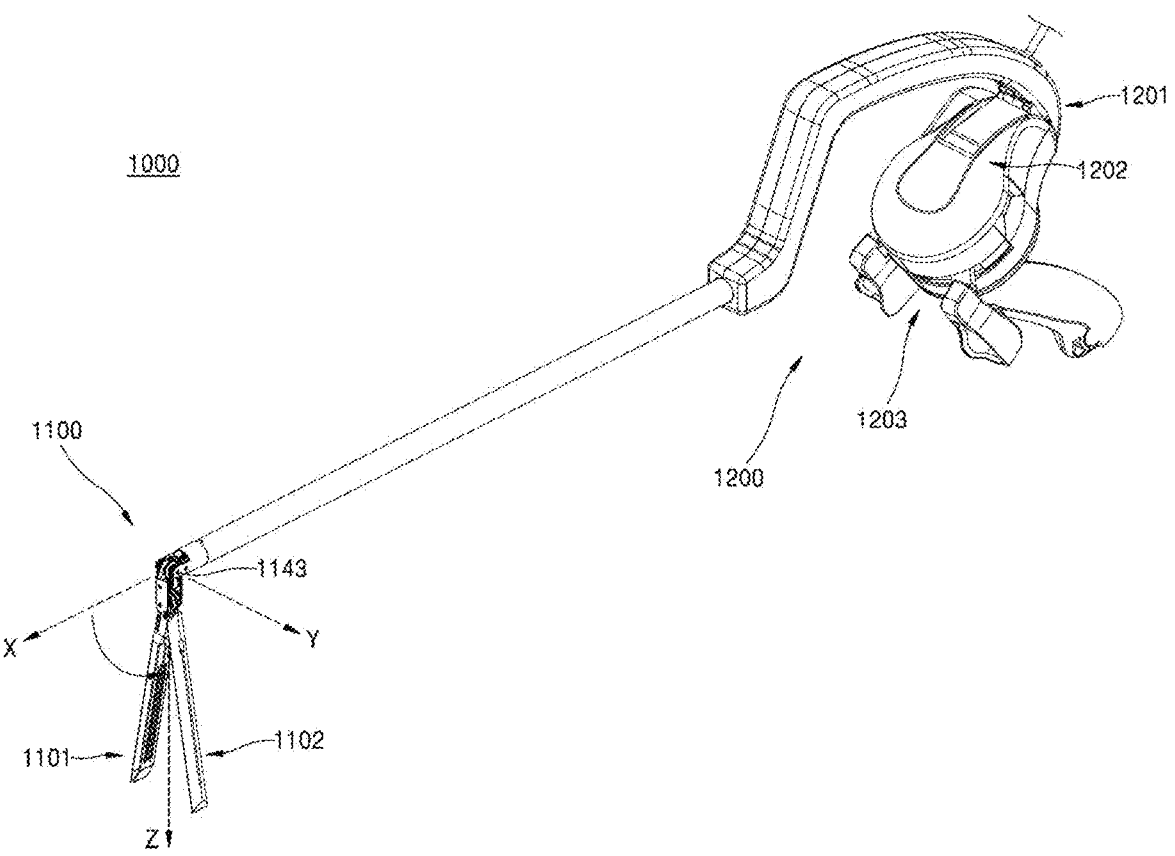
Figure 46:
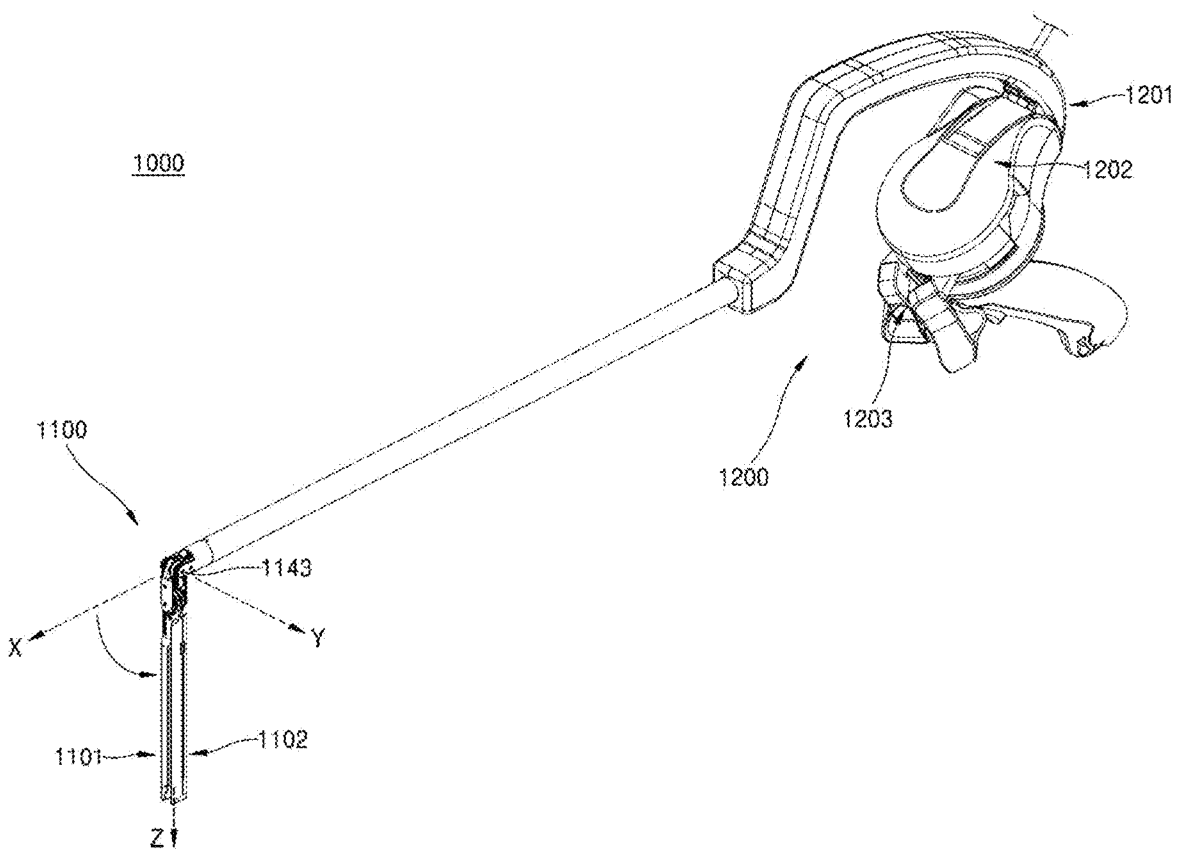

In detail, FIG. 43 is a view illustrating a state in which the jaws are pitch-rotated by −90°, and FIG. 44 is a view illustrating a process of performing an actuation motion in a state in which the jaws are pitch-rotated by −90°. FIG. 45 is a view illustrating a state in which the jaws are pitch-rotated by +90°, and FIG. 46 is a view illustrating a process of performing an actuation motion in a state in which the jaws are pitch-rotated by +90°.

Referring to FIGS. 43 to 46, it can be seen that, in performing a pitch motion, the motions of the manipulation part 1200 and the end tool 1100 are intuitively matched. That is, when the manipulation part 1200 is rotated in a positive (+) direction with respect to the pitch rotation shaft (Y-axis), the end tool 1100 is also rotated in the positive (+) direction with respect to the pitch rotation shaft (Y-axis). In addition, when the manipulation part 1200 is rotated in a negative (−) direction with respect to the pitch rotation shaft (Y-axis), the end tool 1100 is also rotated in the negative (−) direction with respect to the pitch rotation shaft (Y-axis). Here, the rotation angle of the manipulation part 1200 and the rotation angle of the end tool 1100 may be variously set according to the ratio of the pulleys.

FIGS. 47 to 50 are perspective views illustrating a yaw motion of the surgical instrument of FIG. 16.

Figure 47:
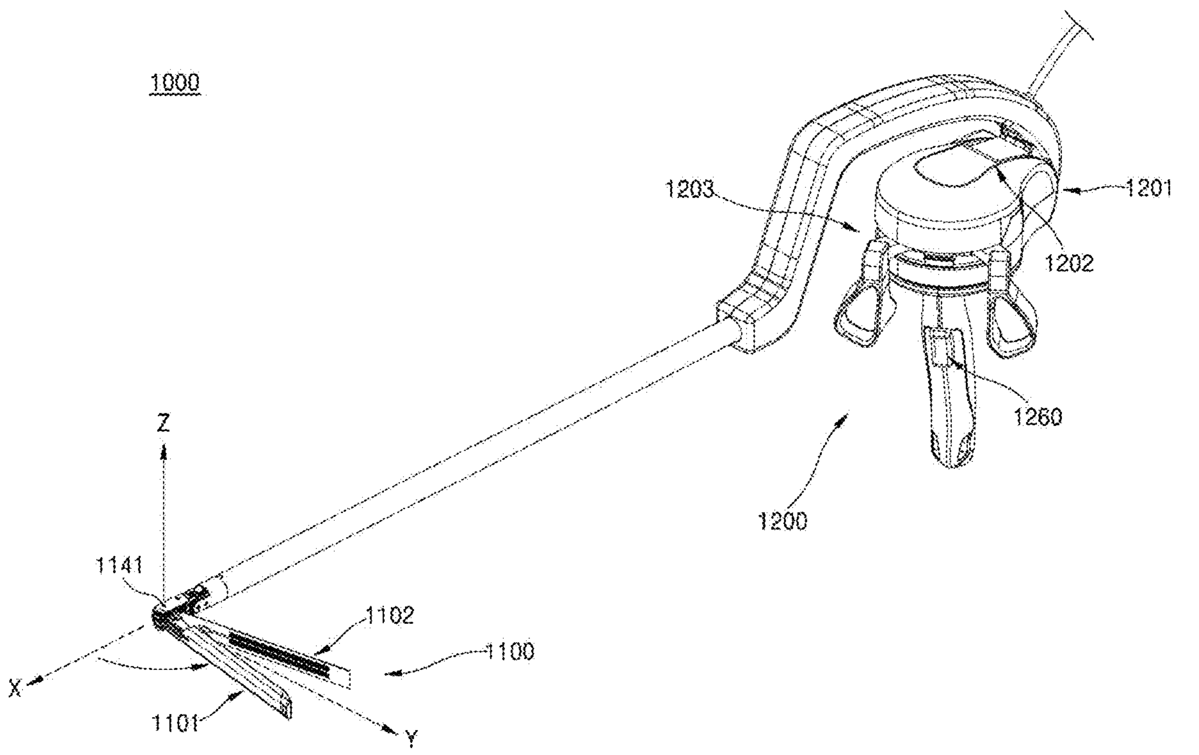
FIGS. 47 to 50 are perspective views illustrating a yaw motion of the surgical instrument of FIG. 16.
Figure 48:
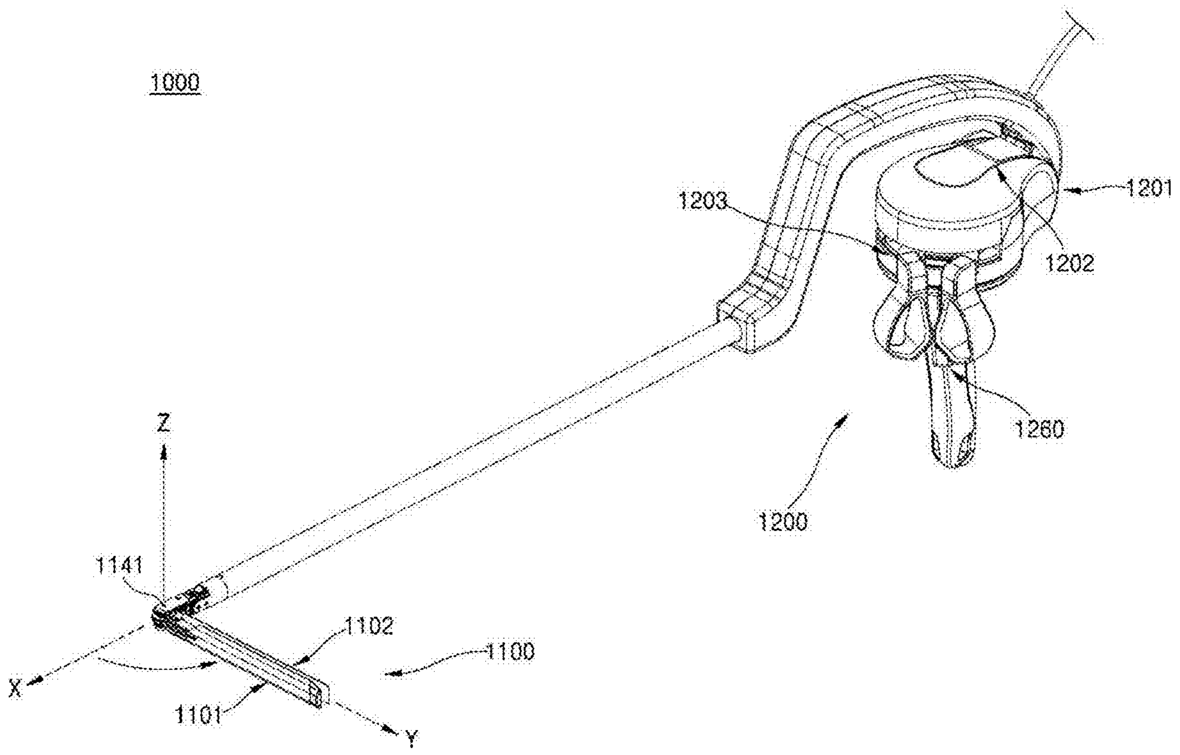
Figure 49:
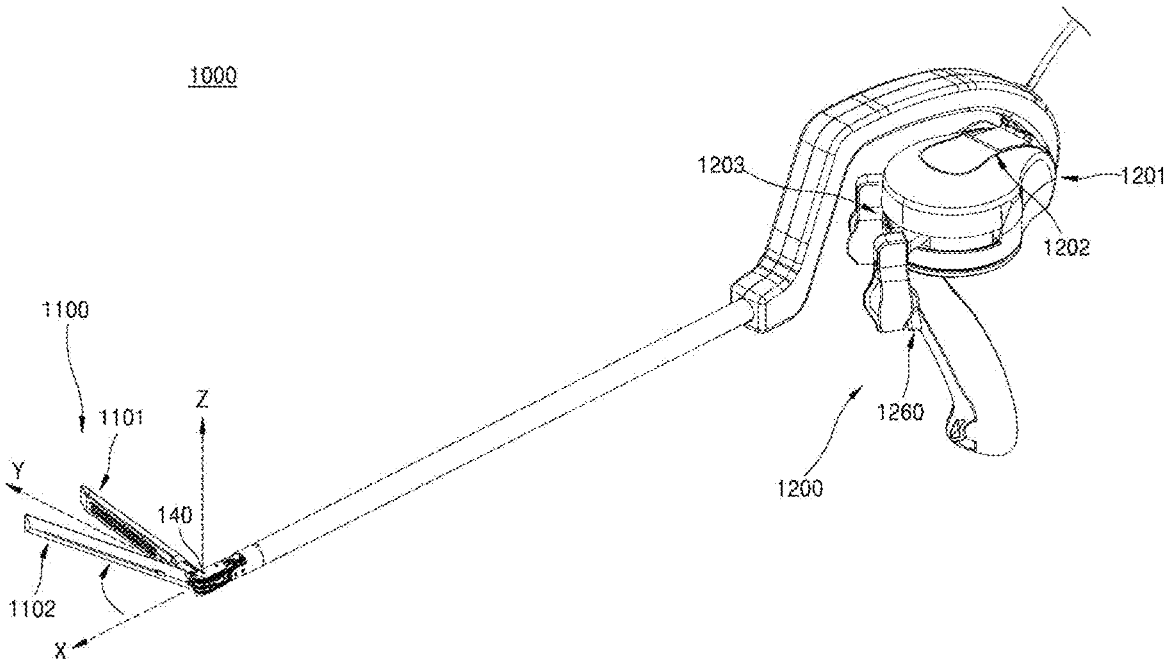
Figure 50:
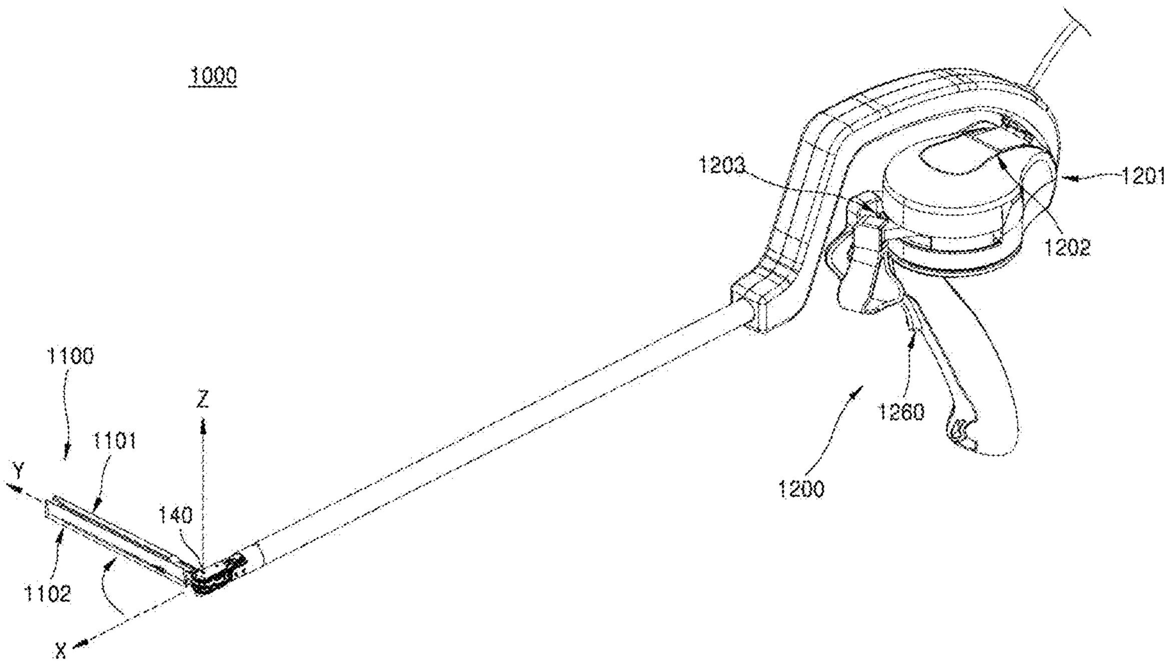

FIG. 47 is a view illustrating a state in which the jaws are yaw-rotated by +90°, and FIG. 48 is a view illustrating a process of performing an actuation motion in a state in which the jaws are yaw-rotated by +90°. FIG. 49 is a view illustrating a state in which the jaws are yaw-rotated by −90°, and FIG. 50 is a view illustrating a process of performing an actuation motion in a state in which the jaws are yaw-rotated by −90°.

Referring to FIGS. 47 to 50, it can be seen that, in performing a yaw motion, the motions of the manipulation part 1200 and the end tool 1100 are intuitively matched. That is, when the manipulation part 1200 is rotated in a positive (+) direction with respect to the yaw rotation shaft (Z-axis), the end tool 1100 is also rotated in the positive (+) direction with respect to the yaw rotation shaft (Z-axis). In addition, when the manipulation part 1200 is rotated in a negative (−) direction with respect to the yaw rotation shaft (Z-axis), the end tool 1100 is also rotated in the negative (−) direction with respect to the yaw rotation shaft (Z-axis). Here, the rotation angle of the manipulation part 1200 and the rotation angle of the end tool 1100 may be variously set according to the ratio of the pulleys.

FIGS. 51 to 54 are plan views illustrating a state in which the end tool of the surgical instrument of FIG. 16 is pitch-rotated and yaw-rotated.

Figure 51:
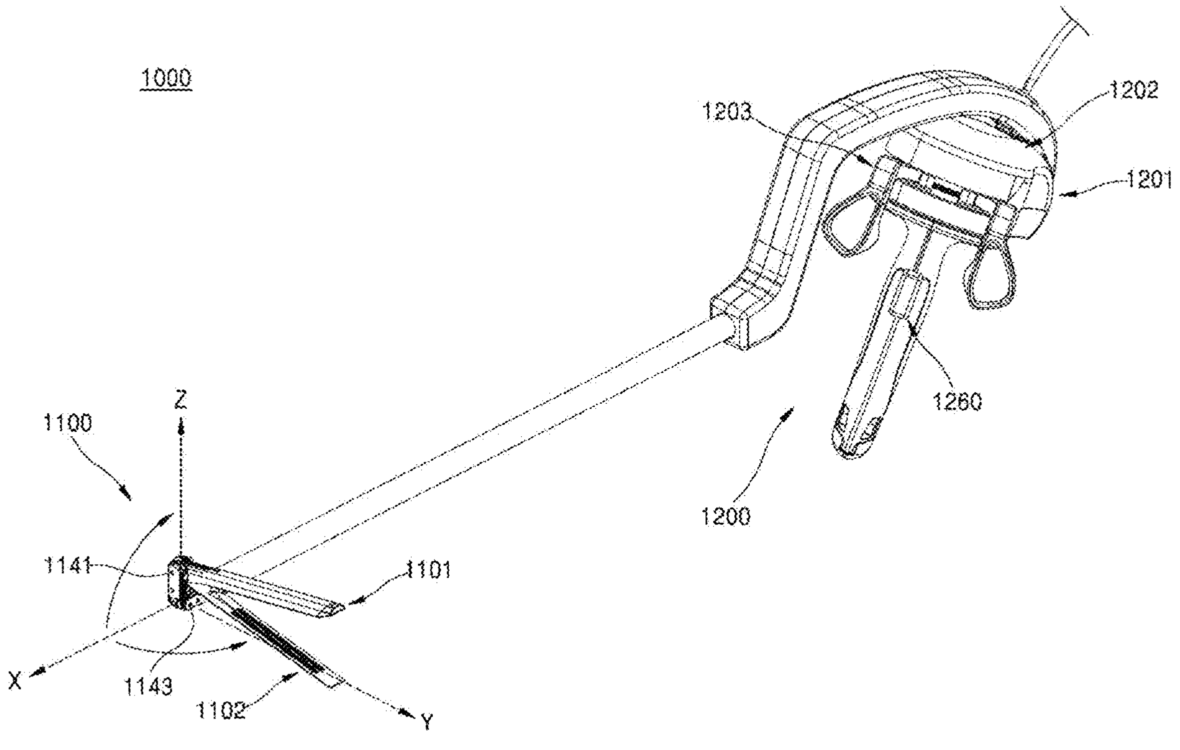
FIGS. 51 to 54 are plan views illustrating a state in which the end tool of the surgical instrument of FIG. 16 is pitch-rotated and yaw-rotated.
Figure 52:
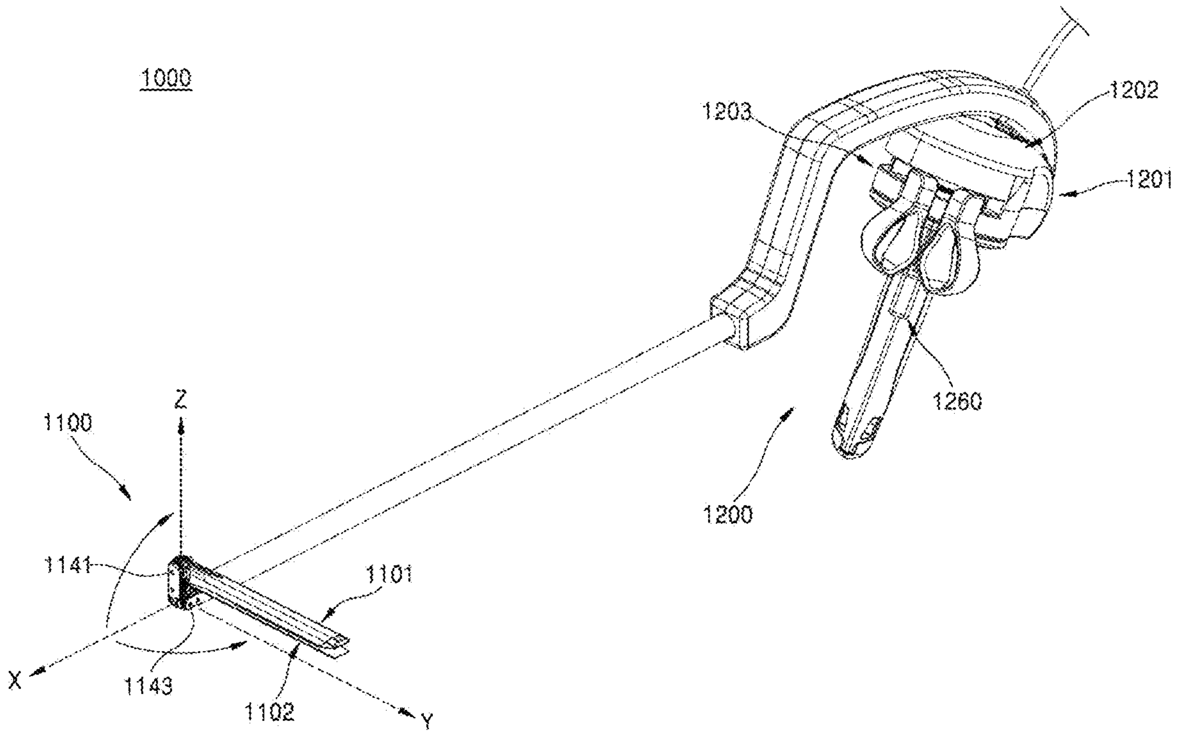
Figure 53:
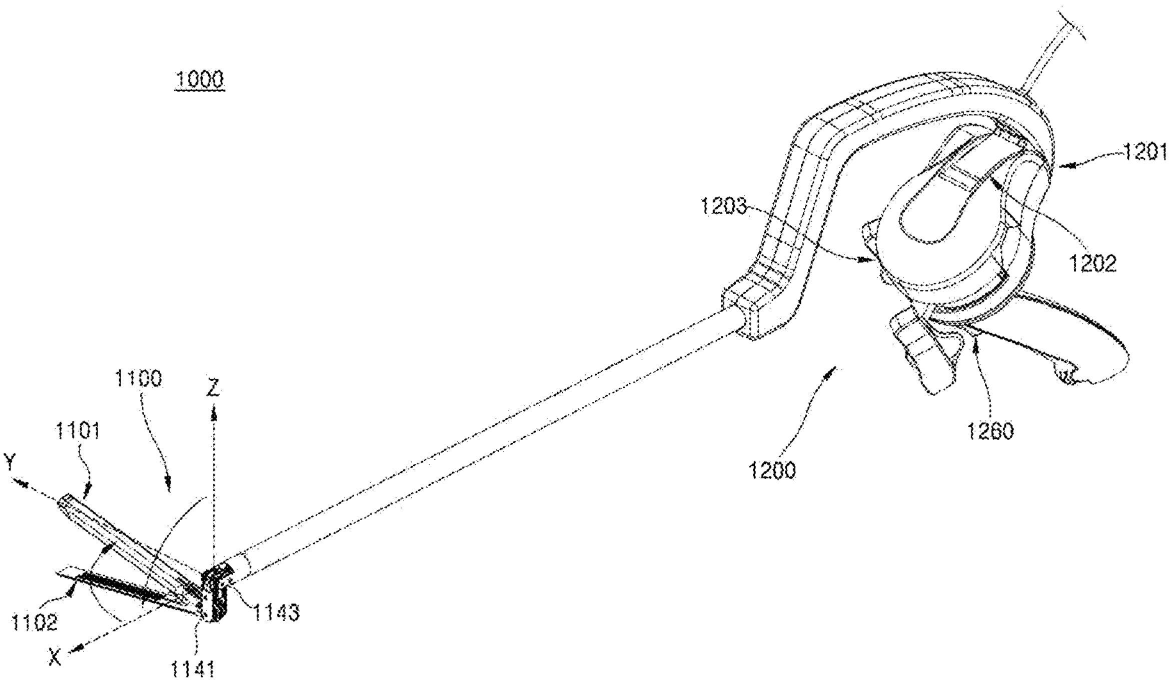
Figure 54:
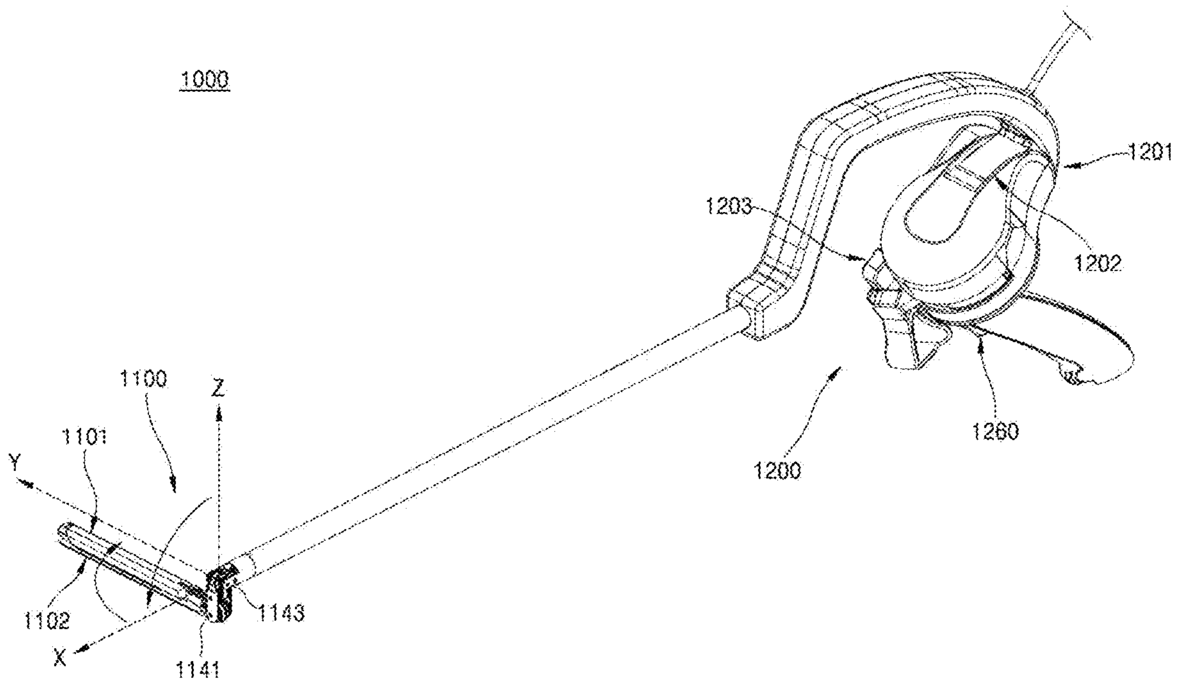

FIG. 51 is a view illustrating a state in which the jaws are pitch-rotated by −90° and at the same time yaw-rotated by +90°, and FIG. 52 is a view illustrating a process of performing an actuation motion in the state in which the jaws are pitch-rotated by −90° and at the same time yaw-rotated by +90°, FIG. 53 is a view illustrating a state in which the jaws are pitch-rotated by +90° and at the same time yaw-rotated by −90°, and FIG. 54 is a view illustrating a process of performing an actuation motion in the state in which the jaws are pitch-rotated by +90° and at the same time yaw-rotated by −90°, Referring to FIGS. 51 to 54, it can be seen that the motions of the manipulation part 1200 and the end tool 1100 are intuitively matched, even when performing the pitch and yaw motions simultaneously.

(Modified Example of Staple Drive Assembly)

Hereinafter, one modified example of the staple drive assembly (1150 in FIG. 21 or the like) of the surgical instrument 1000 of FIG. 16 will be described.

Figure 55:
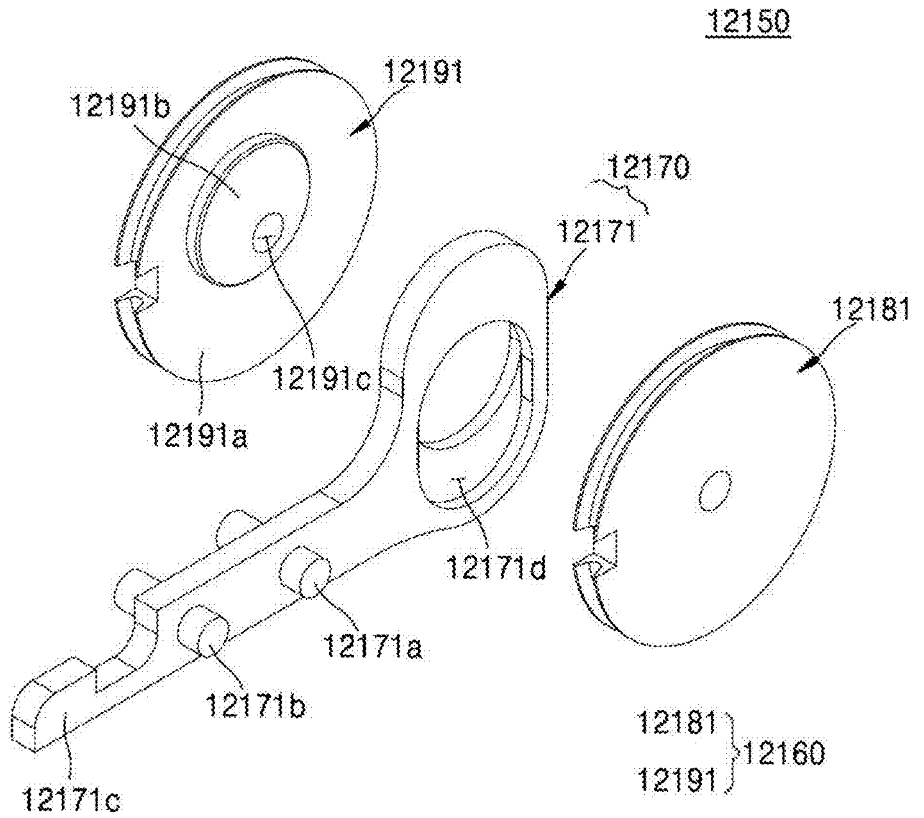
FIGS. 55 and 56 are exploded perspective views illustrating one modified example of a staple drive assembly of the surgical instrument of FIG. 16.
Figure 56:
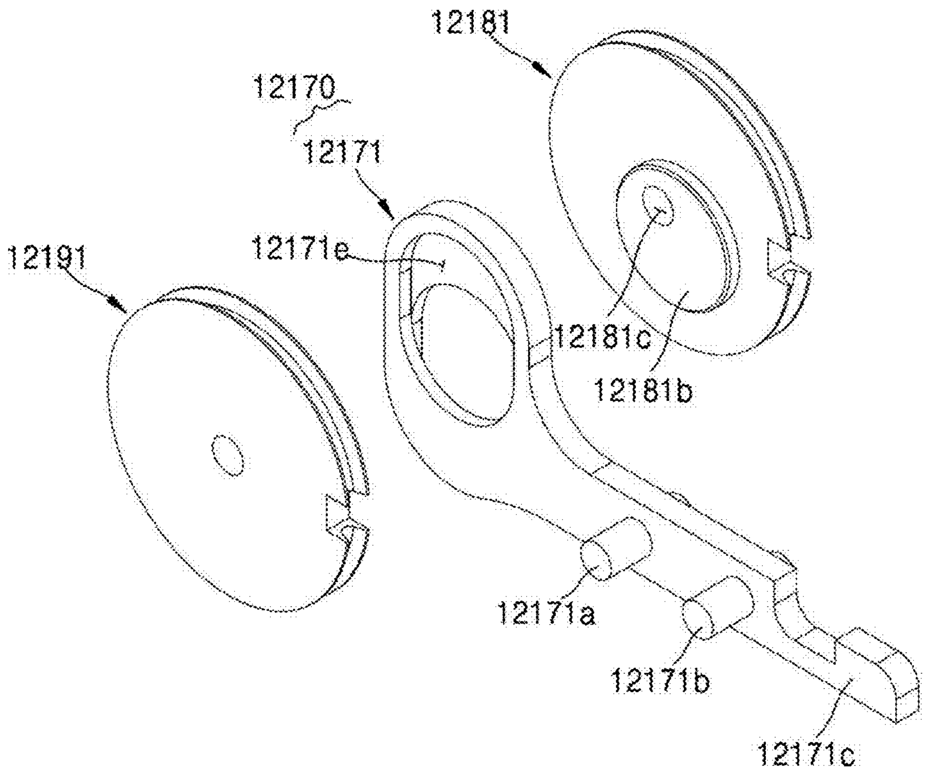

FIGS. 55 and 56 are exploded perspective views illustrating one modified example of the staple drive assembly of the surgical instrument of FIG. 16.

Figure 57:
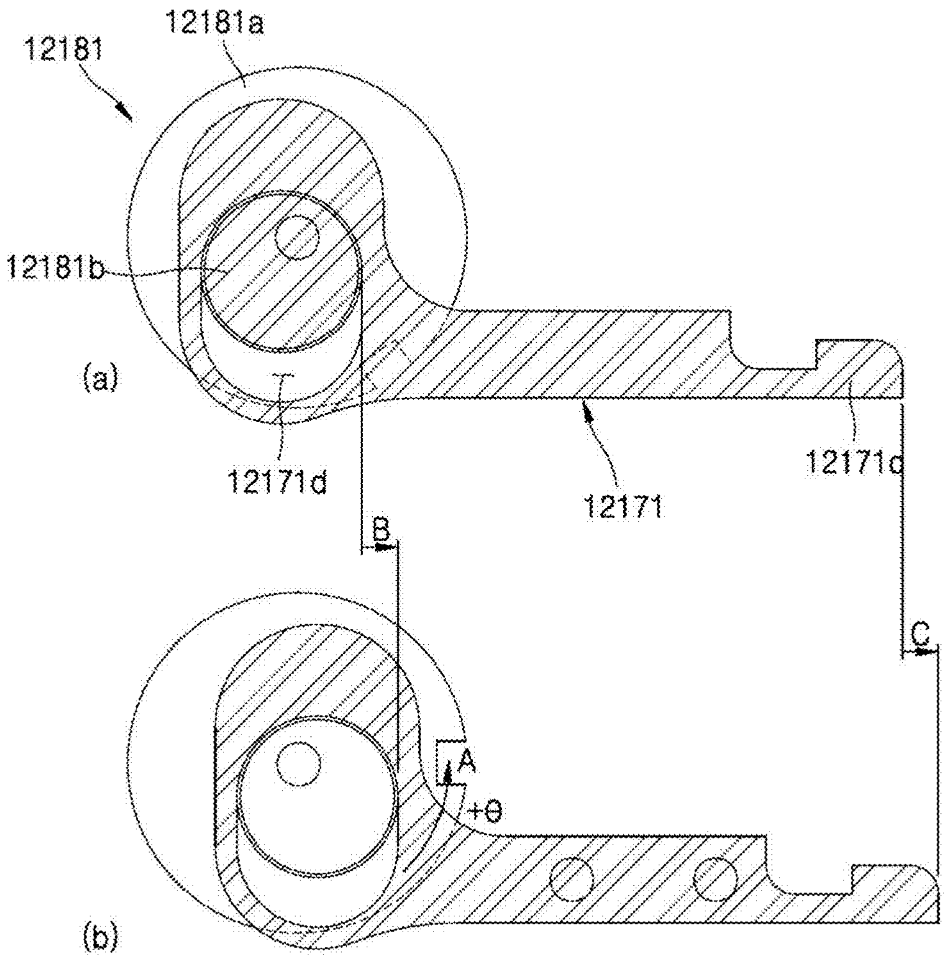
FIGS. 57 and 58 are side views illustrating one modified example of the staple drive assembly of the surgical instrument of FIG. 16.
Figure 58:
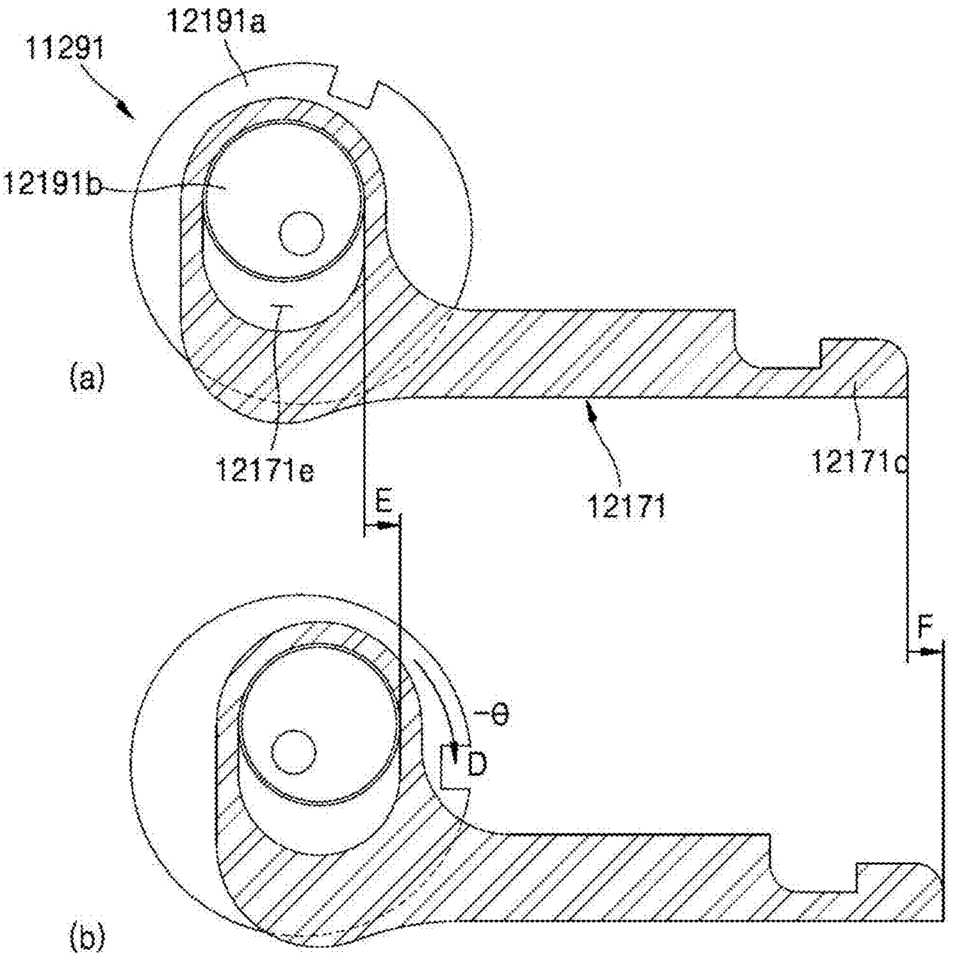

FIGS. 57 and 58 are side views illustrating one modified example of the staple drive assembly of the surgical instrument of FIG. 16.

Figure 59:
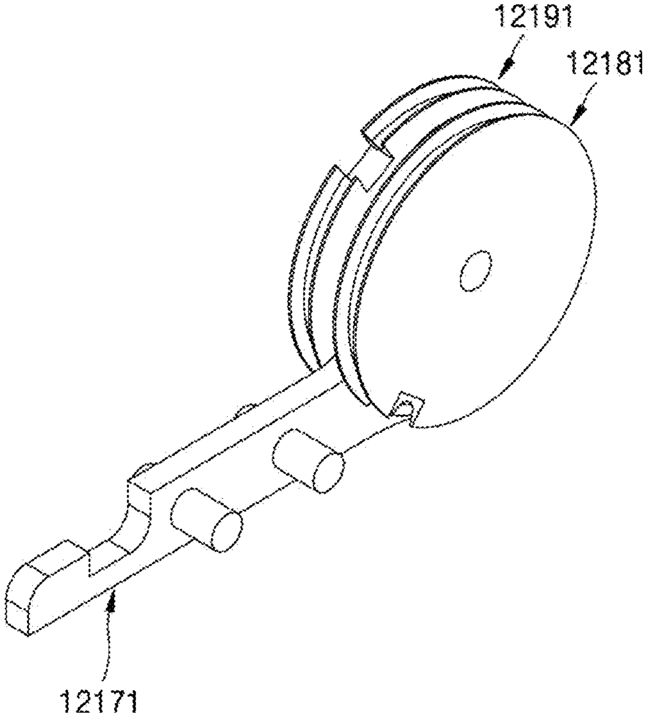
FIGS. 59 and 60 are perspective views illustrating motions of the staple drive assembly of FIGS. 55 to 58.
Figure 60:
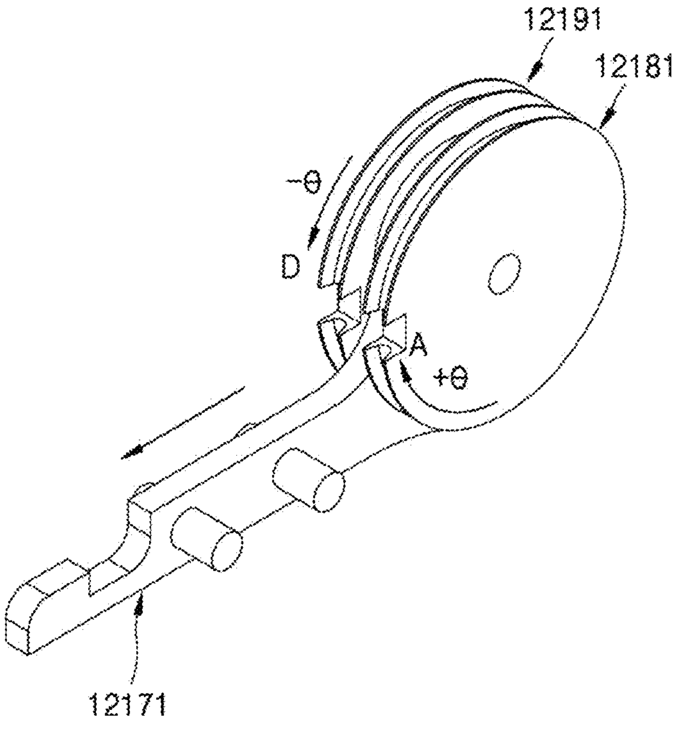

FIGS. 59 and 60 are perspective views illustrating motions of the staple drive assembly of FIGS. 55 to 58.

Referring to FIGS. 55 to 60, a staple drive assembly 12150 may include a staple pulley assembly 12160 and a staple link assembly 12170. Here, the staple drive assembly 12150 is connected to the reciprocating assembly 1550 of the cartridge 1500 described above, and converts a rotational motion of the staple pulley assembly 12160 into a linear motion of the reciprocating assembly 1550.

The staple pulley assembly 12160 may include one or more staple pulleys. In detail, the staple pulley assembly 12160 may include a first staple pulley 12181 and a second staple pulley 12191.

The staple link assembly 12170 may include one or more link members 12171. In addition, the link member 12171 may include one or more links. For example, in the present modified example, it is assumed that the staple link assembly 12170 includes one link member 12171, and the link member 12171 includes one link.

In the present modified example, the staple pulley assembly 12160 and the staple link assembly 12170 form a cam-slot structure. In addition, with such a structure, a force for moving the reciprocating assembly 1550 forward may be amplified.

In detail, the staple pulley assembly 12160 may include the first staple pulley 12181 and the second staple pulley 12191.

The first staple pulley 12181 may include a body 12181*a*, a protruding member 12181*b*, and a shaft pass-through part 12181*c*.

The body 12181*a* is formed in the shape of a disk.

The shaft pass-through part 12181*c* may be formed in a center portion of the body 12181*a*. The shaft pass-through part 12181*c* may be formed in the form of a hole, and the end tool jaw pulley rotation shaft may be inserted through the shaft pass-through part 12181*c*.

In addition, the protruding member 12181*b* may be formed on the body 12181*a* of the first staple pulley 12181. The protruding member 12181*b* may be coupled to the link member 12171 of the staple link assembly 12170. Here, the center of the protruding member 12181*b* may not coincide with the center of the first staple pulley 12181, and the protruding member 12181*b* may be formed to be eccentric to a certain extent with respect to the first staple pulley 12181. The protruding member 12181*b* may be fitted into a first slot 12171*d* of the link member 12171, which will be described later.

The second staple pulley 12191 may include a body 12191*a*, a protruding member 12191*b*, and a shaft pass-through part 12191*c*.

The body 12191*a* is formed in the shape of a disk.

The shaft pass-through part 12191*c* may be formed in a center portion of the body 12191*a*. The shaft pass-through part 12191*c* may be formed in the form of a hole, and the end tool jaw pulley rotation shaft may be inserted through the shaft pass-through part 12191*c*.

In addition, the protruding member 12191*b* may be formed on the body 12191*a* of the second staple pulley 12191. The protruding member 12191*b* may be coupled to the link member 12171 of the staple link assembly 12170. Here, the center of the protruding member 12191*b* may not coincide with the center of the second staple pulley 12191, and the protruding member 12191*b* may be formed to be eccentric to a certain extent with respect to the second staple pulley 12191. The protruding member 12191*b* may be fitted into a second slot 12171*e* of the link member 12171, which will be described later.

Meanwhile, the end tool 1100 of the present disclosure may further include the staple link assembly 12170 connected to the staple pulley assembly 12160, and the staple link assembly 12170 may include the link member 12171. Here, the staple link assembly 12170 may serve to connect the staple pulley assembly 12160 to the reciprocating assembly 1550 of the cartridge 1500 to be described later.

In the present embodiment, the staple link assembly 12170 includes one link member 12171, and the link member 12171 includes only one link. That is, by coupling the staple pulley assembly 12160 and the staple link assembly 12170 by a cam-slot structure, it is possible to convert a rotational motion of the staple pulley assembly 12160 into a linear motion of the staple link assembly 12170 even when the staple link assembly 12170 includes only one link.

In detail, the link member 12171 may be formed as a single link.

The link member 12171 is formed in a shape in which an elongated bar and an elliptical-shaped flat plate are coupled, and may have a bent portion, for example, formed approximately in the shape of the alphabet letter "L." Here, the link member 12171 may include a first protrusion 12171*a*, a second protrusion 12171*b*, a coupling part 12171*c*, the first slot 12171*d*, and the second slot 12171*e*.

The first protrusion 12171*a* and the second protrusion 12171*b* may be formed in one region of a central portion of the link member 12171. The first protrusion 12171*a* and the second protrusion 12171*b* may be fitted into a guide groove (1101*b* of FIG. 22) of the first jaw.

As described above, as the first protrusion 12171*a* and the second protrusion 12171*b* are moved along the guide groove 1101*b* in a state in which the first protrusion 12171*a* and the second protrusion 12171*b* of the link member 12171 formed in a protruding shape are fitted into the groove-shaped guide groove 1101*b*, the link member 12171 is moved with respect to a first jaw 12101 (and the cartridge 1500 therein). This will be described in more detail later.

Meanwhile, the coupling part 12171*c* may be formed at one end portion of the link member 12171. The coupling part 12171*c* may be coupled to the coupling part 1551*a* of the reciprocating member 1551 of the cartridge 1500.

Meanwhile, the first slot 12171*d* and the second slot 12171*e* may be formed at an end portion of the link member 12171 opposite to the one end portion at which the coupling part 12171*c* is formed.

In detail, the first slot 12171*d* may be formed in a surface of the link member 12171 facing the first staple pulley 12181. Here, the first slot 12171*d* is formed in the form of an elongated hole, into which the protruding member 12181*b* of the first staple pulley 12181 may be fitted. The first slot 12171*d* is formed to have a predetermined curvature, and may be formed in an approximately elliptical shape. At this time, the first slot 12171*d* may be formed to be larger than the protruding member 12181*b* by a certain extent. Thus, the protruding member 12181*b* is formed to be movable in the first slot 12171*d* by a certain extent in a state in which the protruding member 12181*b* of the first staple pulley 12181 is fitted into the first slot 12171*d* of the link member 12171.

As described above, the protruding member 12181*b* may be formed to be eccentric to a certain extent with respect to the center of the first staple pulley 12181. Thus, when the first staple pulley 12181 is rotated, the protruding member 12181*b*, while in contact with the first slot 12171*d*, may push the first slot 12171*d* to move the link member 12171. That is, when the first staple pulley 12181 is rotated, the protruding member 12181*b*, while in contact with the first slot 12171*d*, is moved in the first slot 12171*d*, which causes the link member 12171 to be linearly moved along the guide groove 1101*b* of the first jaw 12101.

Here, the first slot 12171*d* may be formed not to pass through the entire thickness of the link member 12171 but to pass through approximately half of the entire thickness of the link member 12171. In other words, the first slot 12171*d* may be formed to have substantially the same thickness as the thickness of the protruding member 12181*b* of the first staple pulley 12181.

Meanwhile, the second slot 12171*e* may be formed in the link member 12171. In detail, the second slot 12171*e* may be formed in a surface of the link member 12171 facing the second staple pulley 12191. Here, the second slot 12171*e* is formed in the form of an elongated hole, into which the protruding member 12191*b* of the second staple pulley 12191 may be fitted. The second slot 12171*e* is formed to have a predetermined curvature, and may be formed in an approximately elliptical shape. At this time, the second slot 12171*e* may be formed to be larger than the protruding member 12191*b* by a certain extent. Thus, the protruding member 12191*b* is formed to be movable in the second slot 12171*e* by a certain extent in a state in which the protruding member 12191*b* of the second staple pulley 12191 is fitted into the second slot 12171*e* of the link member 12171.

As described above, the protruding member 12191*b* may be formed to be eccentric to a certain extent with respect to the center of the second staple pulley 12191. Thus, when the second staple pulley 12191 is rotated, the protruding member 12191*b*, while in contact with the second slot 12171*e*, may push the second slot 12171*e* to move the link member 12171. That is, when the second staple pulley 12191 is rotated, the protruding member 12191*b*, while in contact with the second slot 12171*e*, is moved in the second slot 12171*e*, which causes the link member 12171 to be linearly moved along the guide groove 1101*b* of the first jaw (1101 of FIG. 22).

Here, the second slot 12171*e* may be formed not to pass through the entire thickness of the link member 12171 but to pass through approximately half of the entire thickness of the link member 12171. In other words, the second slot 12171*e* may be formed to have substantially the same thickness as the thickness of the protruding member 12191*b* of the second staple pulley 12191.

Here, the first slot 12171*d* and the second slot 12171*e* may be formed to at least partially overlap. In addition, the sum of the y-axis directional thickness of the first slot 12171*d* and the second slot 12171*e* may be formed to be approximately equal to the y-axis direction thickness of the link member 12171.

Here, the first slot 12171*d* and the second slot 12171*e* may be formed to be vertically symmetrical with respect to the rotation shaft. As such, since the first slot 12171*d* and the second slot 12171*e* are formed to be vertically symmetrical with respect to the rotation shaft, the protruding member 12181*b* of the first staple pulley 12181 coupled to the link member 12171 and the protruding member 12191*b* of the second staple pulley 12191 may be disposed to be symmetrical to each other. This will be described in more detail later.

(Displacement and Motion of Staple Link Assembly According to Rotation of Staple Pulley)

Hereinafter, displacement of the staple link assembly 12170 according to the rotation of the first staple pulley 12181 and the second staple pulley 12191 will be described.

Referring to FIG. 57, the first staple pulley 12181 and the staple link assembly 12170 are coupled in the form of a cam-slot That is, the cam-shaped protruding member 12181*b* formed on the first staple pulley 12181 is coupled to the first slot 12171*d* formed in the link member 12171. Accordingly, when the first staple pulley 12181 is rotated in the direction of an arrow A, the displacement of the protruding member 12181*b* of the first staple pulley 12181 in the X-axis direction becomes B. In addition, a displacement of the staple link assembly 12170 in the X-axis direction becomes C.

Similarly, referring to FIG. 58, in the present embodiment, the second staple pulley 12191 and the staple link assembly 12170 are coupled in the form of a cam-slot. That is, the cam-shaped protruding member 12191*b* formed on the second staple pulley 12191 is coupled to the second slot 12171*e* formed in the link member 12171. Accordingly, when the second staple pulley 12191 is rotated in the direction of an arrow D, the displacement of the protruding member 12191*b* of the second staple pulley 12191 in the X-axis direction becomes E. In addition, the displacement of the staple link assembly 12170 in the X-axis direction becomes F.

When the staple pulley and the staple link assembly are coupled in a link-shaft manner rather than a cam-slot manner as compared with the above case, the displacement of the staple link assembly in the X-axis direction will be much increased.

In other words, as compared to the case in which the staple pulley and the staple link assembly are axially coupled, when the staple pulley and the staple link assembly are cam-slot coupled as in the present modified example, the displacement of the staple link assembly in the X-axis direction will be reduced even when the staple pulley is rotated by the same amount.

Meanwhile, since work is the product of force and displacement, assuming that the work for rotating the staple pulley is the same, the displacement and the force are inversely proportional to each other. Accordingly, when the displacement is reduced, the force is increased in inverse proportion to the displacement.

As a result, in the present modified example, each of the first staple pulley 12181 and the second staple pulley 12191 is coupled in the form of a cam-slot to the staple link assembly 12170, and the displacement of the staple link assembly 12170 in the X-axis direction caused by the rotation of the first staple pulley 12181 and the second staple pulley 12191 is relatively reduced as compared to the embodiments described above, and thus the force received by the staple link assembly 12170 in the X-axis direction is increased relative to a simple link structure.

According to the present modified example described above, a force for moving the staple link assembly 12170 and the reciprocating assembly 1550 connected thereto forward is amplified, and thus a stapling motion may be performed more robustly.

In particular, in the present modified example, since two staple pulleys (i.e., the first staple pulley 12181 and the second staple pulley 12191) that are symmetrical to each other are provided, a force with which the staple pulley assembly 12160 pushes the staple link assembly 12170 may be amplified approximately twice as compared to when only one staple pulley is provided.

In addition, the first staple pulley 12181 and the second staple pulley 12191 are symmetrically disposed in a left and right direction with respect to the XZ plane, and thus balanced in the left and right direction in performing a stapling motion, so that the end tool stably performs motions with respect to the yaw rotation shaft without moving in the left and right direction as a whole. In addition, by making winding directions of the wire corresponding to the first staple pulley 12181 and the wire corresponding to the second staple pulley 12191 to be opposite to each other, movements with respect to the rotation shaft 1143 may also be mutually canceled.

Hereinafter, rotation directions of the first staple pulley 12181 and the second staple pulley 12191 will be described.

Referring to FIGS. 57 to 60, the staple link assembly 12170 is moved forward when the first staple pulley 12181 rotates in the direction of an arrow A in FIG. 60 (i.e., in the clockwise direction), and the staple link assembly 12170 is moved forward when the second staple pulley 12191 rotates in the direction of an arrow D in FIG. 60 (i.e., in the counterclockwise direction).

In contrast, the first staple pulley 12181 moves the staple link assembly 12170 backward when rotated in the counterclockwise direction, and the second staple pulley 12191 moves the staple link assembly 12170 backward when rotated in the clockwise direction.

As a result, when the first staple pulley 12181 and the second staple pulley 12191 are rotated in opposite directions, the staple link assembly 12170 is moved (forward or backward). In contrast, when the first staple pulley 12181 and the second staple pulley 12191 are rotated in the same direction, the rotations of the two pulleys are canceled out and thus the staple link assembly 12170 is not moved.

As a result, in the state as shown in FIG. 59, when the first staple pulley 12181 is rotated in the clockwise direction while the second staple pulley 12191 is rotated in the counterclockwise direction, the link member 12171 connected to the first staple pulley 12181 and the second staple pulley 12191 may be moved as a whole toward the distal end (see 1101*f* of FIG. 22) of the first jaw (1101 of FIG. 22).

In contrast, when the first staple pulley 12181 is rotated in the counterclockwise direction while the second staple pulley 12191 is rotated in the clockwise direction, the link member 12171 connected to the first staple pulley 12181 and the second staple pulley 12191 may be moved as a whole toward the proximal end (see 1101*g* of FIG. 22) of the first jaw (1101 of FIG. 22).

Thus, a bidirectional rotational motion of the staple pulley assembly 12160 causes a reciprocating linear motion of the reciprocating assembly 1550 of the cartridge 1500 through the staple link assembly 12170.

The driving part MTU may simultaneously drive the first staple pulley 12181 and the second staple pulley 12191 of the staple pulley assembly 12160. For example, the driving part MTU may drive the first staple pulley 12181 and the second staple pulley 12191 by reversing the driving of two wires through an intermediate conversion member such as a slide member or the like from the rotational motion of the motor member.

The driving information, such as a rotation amount, of the driving part MTU may be measured using the detection member 1130 to determine motion information of the staple pulley assembly 12160 and motion information of the staple link assembly 12170 connected to the staple pulley assembly 12160. As a result, information on the forward and backward movements of the reciprocating member (1551 of FIG. 25) may be determined, and finally, motion and position information of the operation member 1540 may be determined.

Figure 61:
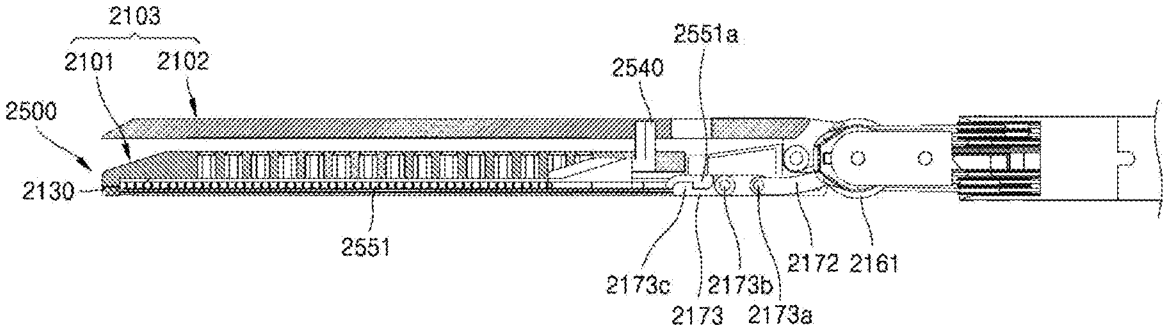
FIG. 61 is a schematic side cross-sectional view illustrating a surgical instrument according to another embodiment of the present disclosure.

FIG. 61 is a schematic side cross-sectional view illustrating a surgical instrument according to another embodiment of the present disclosure.

Figure 62:
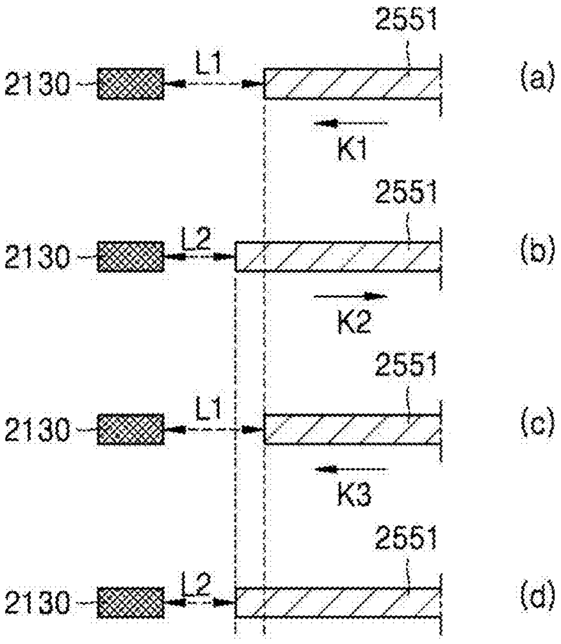
FIG. 62 is a view for describing a motion of a detection member of FIG. 61.

FIG. 62 is a view for describing a motion of a detection member of FIG. 61.

Referring to FIGS. 61 and 62, an end tool 2100 of the surgical instrument according to the present embodiment may include a jaw 2103 and a detection member 2130.

The jaw 2103 may be formed to accommodate an operation member 2540 in at least one region thereof. The jaw 2103 may have various forms, such as being configured as one or more jaws, as a specific example, two jaws. For example, the jaw 2103 may include a first jaw 2101 and a second jaw 2102.

The jaw 2103 is substantially the same as the jaw 1103 of the above-described embodiment, and thus a detailed description thereof will be omitted.

For example, the operation member 2540 may move forward (move toward a distal end) from the state of FIG. 61. A detailed description of the configuration and motion of the operation member 2540 is substantially the same as the operation member 1540 of the above-described embodiment, and thus a detailed description thereof will be omitted When the operation member 2540 changes in position through such forward-moving, the change may be detected by the detection member 2130.

The operation member 2540 may receive a driving force through a reciprocating member 2551 of a reciprocating assembly. The reciprocating member 2551 may be substantially the same as the reciprocating member 1551 of the above-described embodiment. In addition, the reciprocating member 2551 may include a staple pulley assembly including one or more staple pulleys 2161, and a staple link assembly including one or more links 2172 and 2173. The one or more links 2173 may include protrusions 2173*a* and

2173*b* and a fastening part 2173*c*. The staple pulley assembly and the staple link assembly may be substantially the same as the staple pulley assembly 1160 and the staple link assembly 1170 of the above-described embodiment.

The reciprocating member 2551 may move by various power sources, such as a driving part (not shown), and the driving part (not shown) and the reciprocating member 2551 may be connected to a power transmission part, including one or more wires.

The detection member 2130 may detect motion information of the reciprocating member 2551. For example, the detection member 2130 may have the form of a proximity sensor that detects the motion or position of the reciprocating member 2551. The detection member 2130 may have an optically sensing form, or in other cases, may be formed as a contact-type sensor.

As an example, the detection member 2130 may be disposed in one region (e.g., one region of the distal end) of the first jaw 2101 at a position that is spaced apart from the reciprocating member 2551 to be close thereto. The detection member 2130 may detect motion information of the reciprocating member 2551, such as forward movement or backward movement, and may determine the degree or number of times the reciprocating member 2551 moves forward or backward during a set time period. Accordingly, a moving distance of the reciprocating member 2551 and a moving distance of the operation member 2540 according thereto may be determined. As a result, position information of the operation member 2540 may be detected and provided to a user.

FIG. 62 is a view for describing a motion of the detection member of FIG. 61.

Referring to FIG. 62A, the reciprocating member 2551 may maintain a first gap L1 with the detection member 2130. When the staple pulley 2161 rotates in one direction (e.g., in the clockwise direction), its driving force is transmitted to the reciprocating member 2551 through the staple link assembly, and the reciprocating member 2551 moves forward in a K1 direction. Accordingly, the gap between the reciprocating member 2551 and the detection member 2130 is maintained at a second gap L2 that is decreased from the first gap L1. In this case, the operation member 2540 may move forward (move forward in the K1 direction) by the amount of movement of the reciprocating member 2551, such as a pitch interval.

Thereafter, referring to FIG. 62B, when the staple pulley 2161 rotates in the opposite direction (e.g., in the counter-clockwise direction), its driving force is transmitted to the reciprocating member 2551 through the staple link assembly, and the reciprocating member 2551 moves backward in a K2 direction. Accordingly, the gap between the reciprocating member 2551 and the detection member 2130 is maintained at the first gap L1 from the second gap L2, as shown in FIG. 62C. In this case, the operation member 2540 may remain stationary without moving backward together with the reciprocating member 2551.

Thereafter, when the staple pulley 2161 rotates in the opposite direction again (e.g., in the clockwise direction), its driving force is transmitted to the reciprocating member 2551 through the staple link assembly, and the reciprocating member 2551 moves forward in a K3 direction in FIG. 62C. Accordingly, the gap between the reciprocating member 2551 and the detection member 2130 is maintained at the second gap L2 of FIG. 62D that is decreased from the first gap L1. In this case, the operation member 2540 may move forward (move forward in the K1 direction) by the amount of movement of the reciprocating member 2551, such as a pitch interval.

When the reciprocating member 2551 repeatedly moves forward and backward in one direction as described above, the gap between the reciprocating member 2551 and the detection member 2130 alternates between the first gap L1 and the second gap L2.

The detection member 2130 may detect this change in the gap to identify motion information, such as information on the forward and backward movements, of the reciprocating member 2551. As a specific example, the number of forward and backward movements or the like of the reciprocating member 2551 may be identified. Accordingly, motion information of the operation member 2540, such as the number of times the operation member 2540 has moved forward, may be identified, and position information of the operation member 2540 may be determined accordingly. As a specific example, information may be easily identified through the pitch interval and the like, which may be the same as described above with reference to FIGS. 8 and 9.

By detecting the motion information of the reciprocating member 2551 through the detection member 2130 as described above, for example by determining the forward and backward movement information, motion and position information of the operation member 2540 can be finally determined. Through this, it is possible to precisely determine a status of each of steps in the process of performing an operation using the end tool 2100 and precisely control initiation of each step's progression.

For example, the operation member 2540 may move forward, e.g., toward the distal end to safely and efficiently perform a process using the end tool 2100, specifically, a stapling motion. As a result, each of steps of the stapling process can be precisely controlled.

Figure 63:
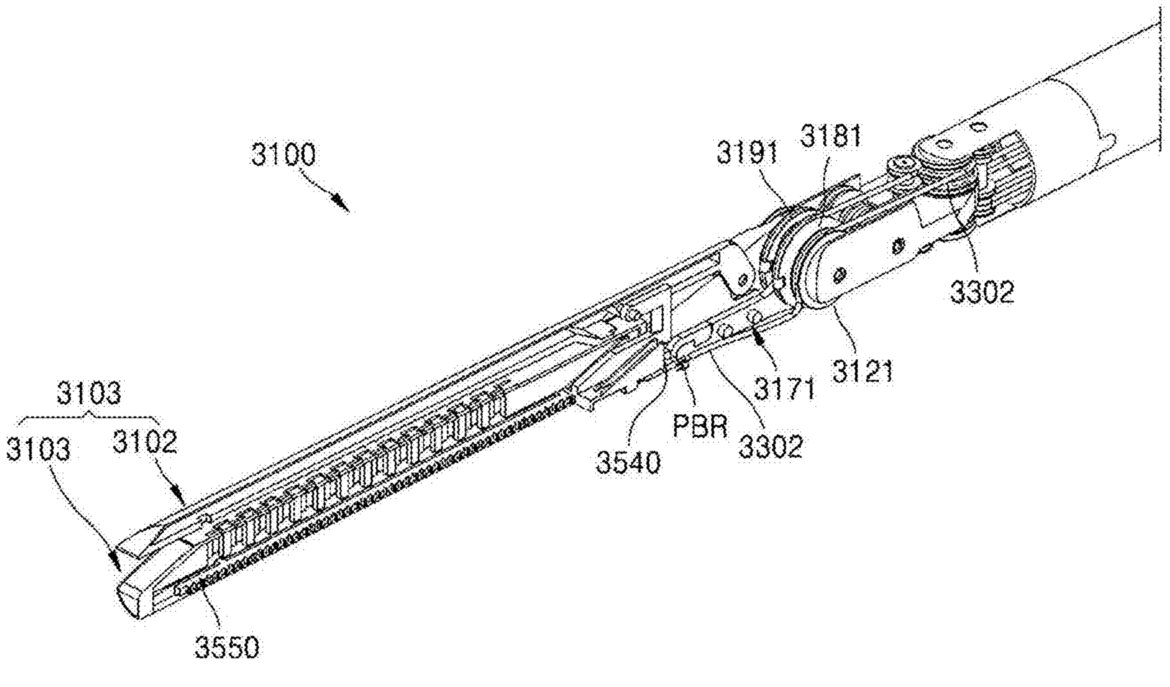
FIGS. 63 and 64 are perspective cross-sectional views illustrating an end tool of a surgical instrument according to another embodiment of the present disclosure.
Figure 64:
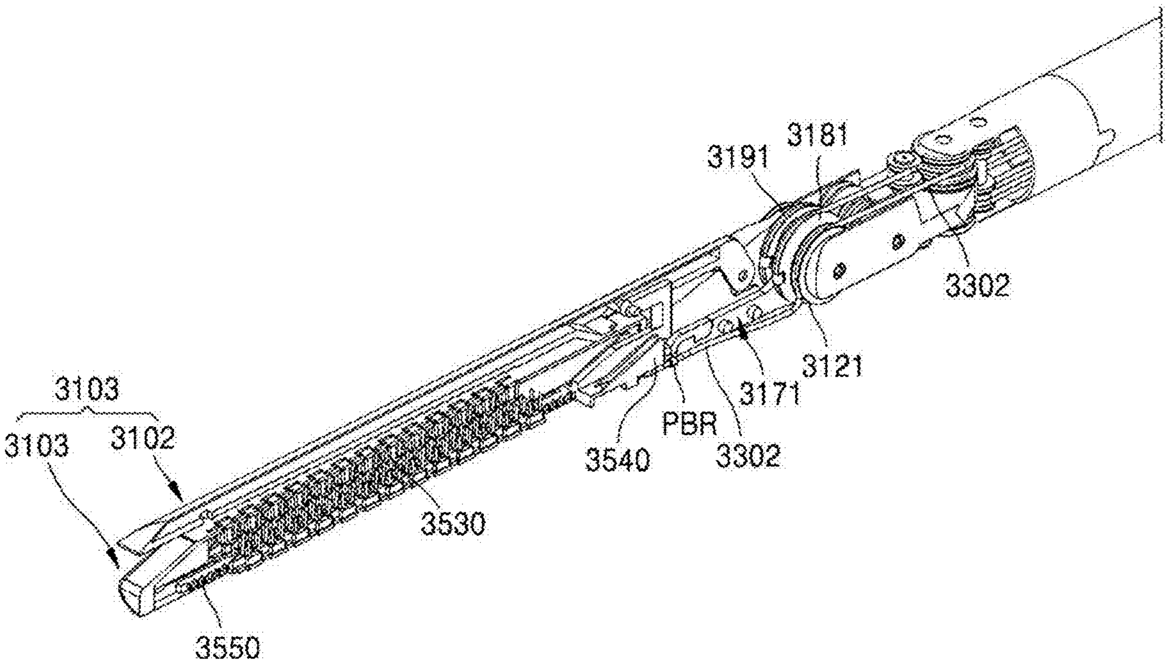

FIGS. 63 and 64 are perspective cross-sectional views illustrating an end tool of a surgical instrument according to another embodiment of the present disclosure.

Figure 65:
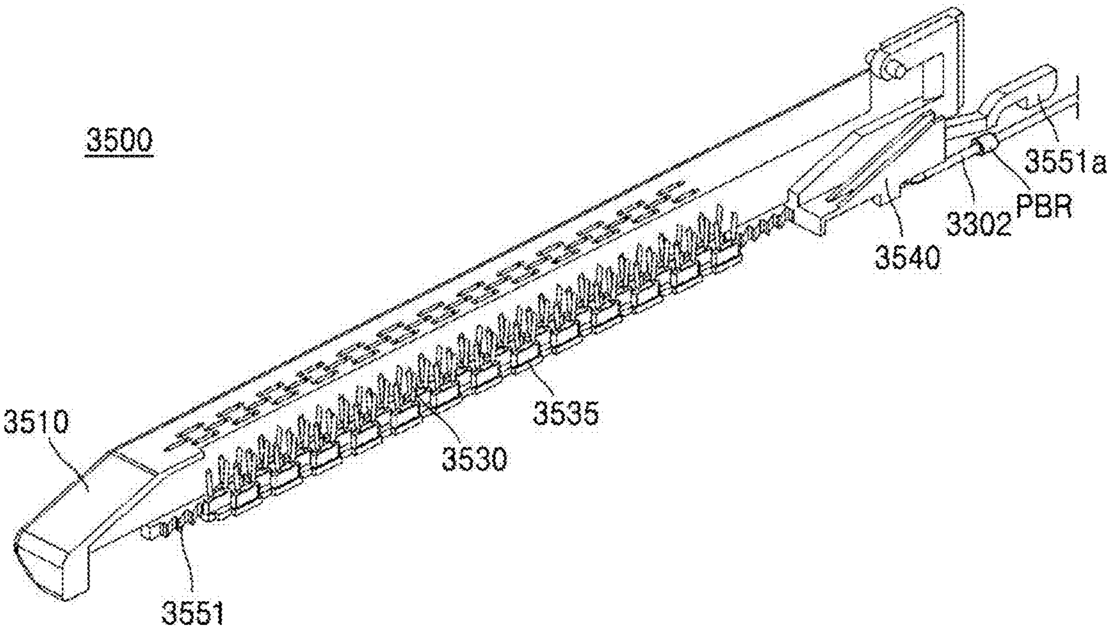
FIG. 65 is an exploded perspective view illustrating a cartridge of FIG. 63.
Figure 66:
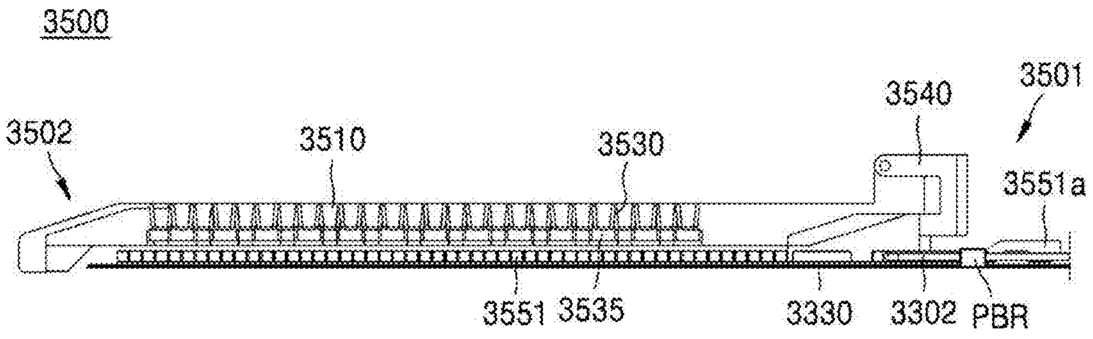
FIG. 66 is a side cross-sectional view illustrating the cartridge of FIG. 63.

FIG. 65 is an exploded perspective view illustrating a cartridge of FIG. 63, and FIG. 66 is a side cross-sectional view illustrating the cartridge of FIG. 63.

Figure 67:
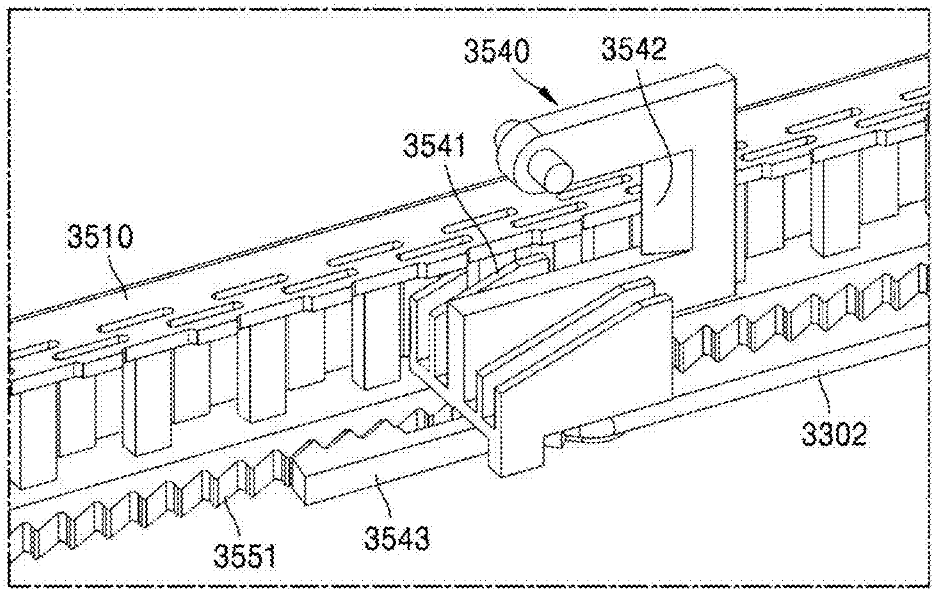
FIG. 67 is a perspective view of the end tool of FIG. 63, including an operation member.

FIG. 67 is a perspective view of the end tool of FIG. 63, including an operation member.

Figure 68:
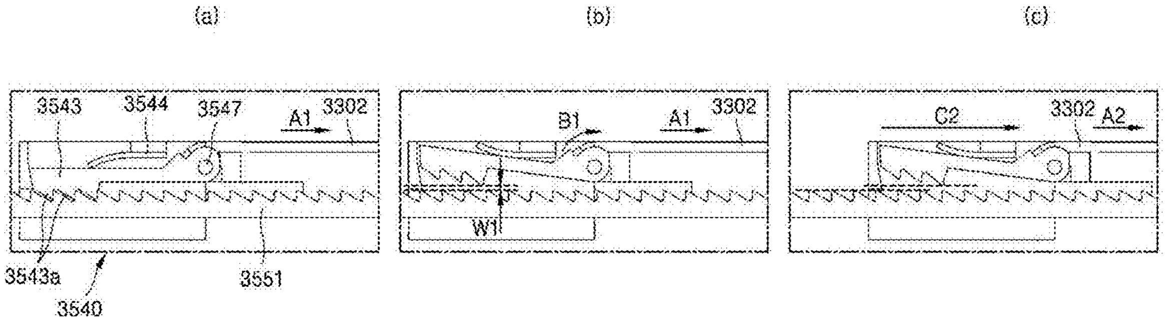
FIG. 68 is a schematic plan view illustrating a backward movement of the operation member of the end tool of FIG. 63.

FIG. 68 is a schematic plan view illustrating a backward movement of the operation member of the end tool of FIG. 63.

Referring to FIGS. 63 and 64, an end tool 3100 of the surgical instrument according to the present embodiment may include a jaw 3103.

The jaw 3103 may be formed to accommodate an operation member 3540 in at least one region thereof. The jaw 3103 may have various forms, such as being configured as one or more jaws, as a specific example, two jaws. For example, the jaw 3103 may include a first jaw 3101 and a second jaw 3102.

For example, the operation member 3540 may move forward (move toward a distal end).

Further, the operation member 3540 may move forward and then backward, and when the operation member 3540 changes in position due to its backward movement by a backward movement wire 3302, this change may be detected by a detection member (not shown), For example, as shown in FIGS. 63 and 64, the movement and position of the backward movement wire 3302 may be detected using the detection member (not shown) disposed on an inner side of the first jaw 3101, and in this case, a measuring member PBR further attached to the backward movement wire 3302 enables the detection member to more effectively detect the motion information of the backward movement wire 3302.

The operation member 3540 may receive a driving force through at least the reciprocating member 3551.

The backward movement wire 3302 may be connected to one region of the operation member 3540. The backward movement of the operation member 3540 may be performed through the backward movement wire 3302. For example, the backward movement wire 3302 may receive a force to move the operation member 3540 toward a proximal end of the jaw 3103 (the right direction in FIG. 66), and in other words, the backward movement wire 3302 may be formed to pull the operation member 3540.

Although not shown in the drawings, a driving part or a driving transmission part (e.g., wires, pulleys, and the like) capable of pulling the backward movement wire 3302 may be connected to the backward movement wire 3302, and the backward movement wire 3302 may be operated according to manual or automatic manipulation.

By pulling the backward movement wire 3302, the operation member 3540 may move backward.

The operation member 3540 may be moved forward by the reciprocating member 3551, and may remain stationary during the backward movement of the reciprocating member 3551 (see above-described embodiment).

At this time, the backward movement wire 3302 may be used to move the operation member 3540 backward to the desired extent.

The detection member (not shown) may detect motion information of the backward movement wire 3302. For example, the detection member (not shown) may have the form of a proximity sensor, which detects the motion or position of the backward movement wire 3302. The detection member (not shown) may have an optically sensing form, or in other cases, may be formed as a contact-type sensor.

The configuration of the end tool 3100 of the surgical instrument of the present embodiment will be described in more detail.

The operation member 3540 may receive a driving force through the reciprocating member 3551 of the reciprocating assembly. The reciprocating member 3551 may be substantially the same as the reciprocating member 1551 of the above-described embodiment. In addition, the reciprocating member 3551 may include a staple pulley assembly including one or more staple pulleys 3181 and 3191, and a staple link assembly including one or more link members 3171. In an optional embodiment, the present embodiment may include the staple drive assembly 12150 of FIG. 55 described above. In addition, as another example, the present embodiment may include the staple drive assembly 1150 of FIG. 21 described above.

Meanwhile, one or more pulleys 3121 associated with the rotational movement of the backward movement wire 3302 may be disposed.

Referring to FIGS. 65 to 67, the cartridge 3500 may be disposed in one region of the first jaw 3101. The cartridge 3500 may be integrally formed with the first jaw 3101, and for example, the cartridge 3500 may be integrally formed with the first jaw 3101 while the operation member 3540 is connected to the backward movement wire 3302. In an optional embodiment, the cartridge 3500 may be formed to be mountable to and dismountable from the first jaw 3101. For example, the backward movement wire 3302 and the operation member 3540 may be formed to be couplable to and decouplable from each other, rather than being integrally connected to each other, thereby facilitating the separation or coupling of the cartridge 3500 from and to the first jaw 3101.

The operation member 3540 pushes and raises staples 3530 while moving forward from a proximal end 3501 toward a distal end 3502, thereby performing stapling.

The configuration of the cartridge 3500, including a housing 3510, the staple 3530 inside the housing 3510, the withdrawal member 3535, and a reciprocating member 3551 is substantially the same as the configuration described with reference to FIGS. 28 and 29, and thus a detailed description thereof will be omitted.

The operation member 3540 may include a wedge 3541, a blade 3542, a ratchet member 3543, an operation part elastic member 3544, a body 3545, a clamp 3546.

The body 3545 may be formed in the shape of an elongated square column, and forms a base of the operation member 3540.

The wedge 3541 is formed on at least one side of the body 3545, and may be formed to have a predetermined inclined surface. That is, the wedge 3541 may be formed to have a greater height at a proximal end 3501 side of the cartridge 3500 than a distal end 3502 side of the cartridge 3500. In the drawing, it is illustrated that two wedges 3541 are formed on each side of the body 3545, but the concept of the present disclosure is not limited thereto, and the wedge 3541 may be formed in various numbers and shapes depending on the shape of the staple 3530 or the withdrawal member 3535 that is in contact with the wedge 3541.

The wedge 3541 may be formed to be in contact with the withdrawal members 3535 or a plurality of staples 3530 in turn and may serve to sequentially push and raise the staples 3530.

The blade 3542 may be formed at one side of the wedge 3541, more specifically, at one side of the wedge 3541 at the proximal end 3501 side. An edge formed to be sharp to cut tissue is formed in one region of the blade 3542.

The ratchet member 3543 is formed on one side of the wedge 3541, more specifically, below wedge 3541, and may be formed to face the reciprocating member 3551 to be described later. The ratchet member 3543 may be formed in the form of a bar and may include a plurality of ratchets on one surface. The mutual motion relationship between the ratchet member 3543 and the reciprocating member 3551 is substantially the same as described in the embodiments described above.

Meanwhile. the ratchet member 3543 may be formed to be rotatable around a rotation shaft 3547. For example, the ratchet member 3543 may be formed to rotationally move by being inserted into the rotation shaft 3547 formed in a protruding form on the body 3545 of the operation member 3540. The rotation shaft 3547 may be disposed closer to the proximal end 3501 than the plurality of ratchets.

Meanwhile, the backward movement wire 3302 may be connected to the ratchet member 3543, and by pulling the backward movement wire 3302, the ratchet member 3543 may rotationally move around the rotation shaft 3547. As a specific example, the backward movement wire 3302 may be connected to one region around the rotation shaft 3547. The operation member 3540 may be moved toward the proximal end 3501 of the cartridge 3500 by the backward movement wire 3302.

The operation part elastic member 3544 is formed on one side of the body 3545 or the wedge 3541 and serves to apply a predetermined elastic force to the ratchet member 3543. In an example, the operation part elastic member 3544 may be formed such that one region is in contact with the body 3545, and another region that is different from the one region is in contact with the ratchet member 3543. The operation part elastic member 3544 may apply an elastic force in a direction in which the ratchet member 3543 comes into close contact with the reciprocating member 3551. To this end, the operation part elastic member 3544 may be formed in the form of a leaf spring, and may be provided in various forms capable of providing a predetermined elastic force to the ratchet member 3543, such as a coil spring, a dish spring, and the like. In addition, although not shown in the drawings, in another optional embodiment, the operation part elastic member 3544 may be integrally formed with the operation member 3540.

The clamp 3546 may be formed on one side of the blade 3542 and may be formed in a shape that is approximately parallel to the body 3545 or the wedge 3541. In addition, a protrusion may be formed at one end portion of the clamp 3546, and the protrusion may move inward along a path formed in one region of the second jaw 3102.

Further, during the forward movement of the operation member 3540, the clamp 3546 is inserted into the second jaw 3102, so that the second jaw 3102 may be close to the first jaw 3101, and the second jaw 3102 and the first jaw 3101 may be naturally closed.

(Backward Movement)

FIG. 68 is a schematic plan view illustrating a backward movement of the operation member of the end tool of FIG. 63.

The ratchet member 3543 may be formed to be rotatable around the rotation shaft 3547, and as a specific example, the ratchet member 3543 may be inserted into the rotation shaft 3547 formed in a shape protruding from the body 3545 of the operation member 3540 and may rotationally move around the rotation shaft 3547.

The backward movement wire 3302 may be connected to the ratchet member 3543, and by pulling the backward movement wire 3302, the ratchet member 3543 may rotationally move around the rotation shaft 3547. As a specific example, the backward movement wire 3302 may be connected to one region around the rotation shaft 3547.

When the backward movement wire 3302 is pulled in the direction of an arrow A1 of FIG. 68B, the ratchet member 3543 is rotated around the rotation shaft 3547 in the direction of an arrow B1 of FIG. 68B.

Here, when a certain amount or more of force is applied to the backward movement wire 3302, the ratchet member 3543 is spaced away from the reciprocating member 3551 to generate a separation gap W1, and the coupling (engagement) between the ratchet member 3543 and the backward movement wire 3302 is released, so that the operation member 3540 becomes movable with respect to the reciprocating member 3551.

In this state, when the backward movement wire 3302 is further pulled in the direction of an arrow A2 of FIG. 68C, the operation member 3540 as a whole is moved in the direction of an arrow C2 of FIG. 68C in a state in which the ratchet member 3543 is spaced away from the reciprocating member 3551.

As a result, the operation member 3540 may be moved backward, i.e., may be moved toward the proximal end 3501 by the backward movement wire 3302.

The backward movement wire 3302 may be used to move the operation member 3540 backward to the desired extent, and the detection member may detect motion information of the backward movement wire 3302. For example, the detection member may be in the form of a proximity sensor that detects the motion or position of the backward movement wire 3302 by detecting the measuring member PBR attached to one region of the backward movement wire 3302.

Through this, motion information of the backward movement wire 3302, such as whether the backward movement wire 3302 has moved and a distance the backward movement wire 3302 has moved, can be detected, and accordingly, a distance the operation member 3540 has moved backward can be determined through the backward movement wire 3302. As a result, position information of the operation member 3540 may be detected and provided to a user.

Since motion and position information of the operation member 3540 can be determined, it is possible to precisely determine a status of each of steps in the process of performing an operation using the end tool 3100 and precisely control initiation of each step's progression.

For example, the process of using the end tool 3100 through the motion of the operation member 3540, specifically a stapling motion, can be performed safely and efficiently. As a result, each of steps of the stapling process can be precisely controlled.

Figure 69:
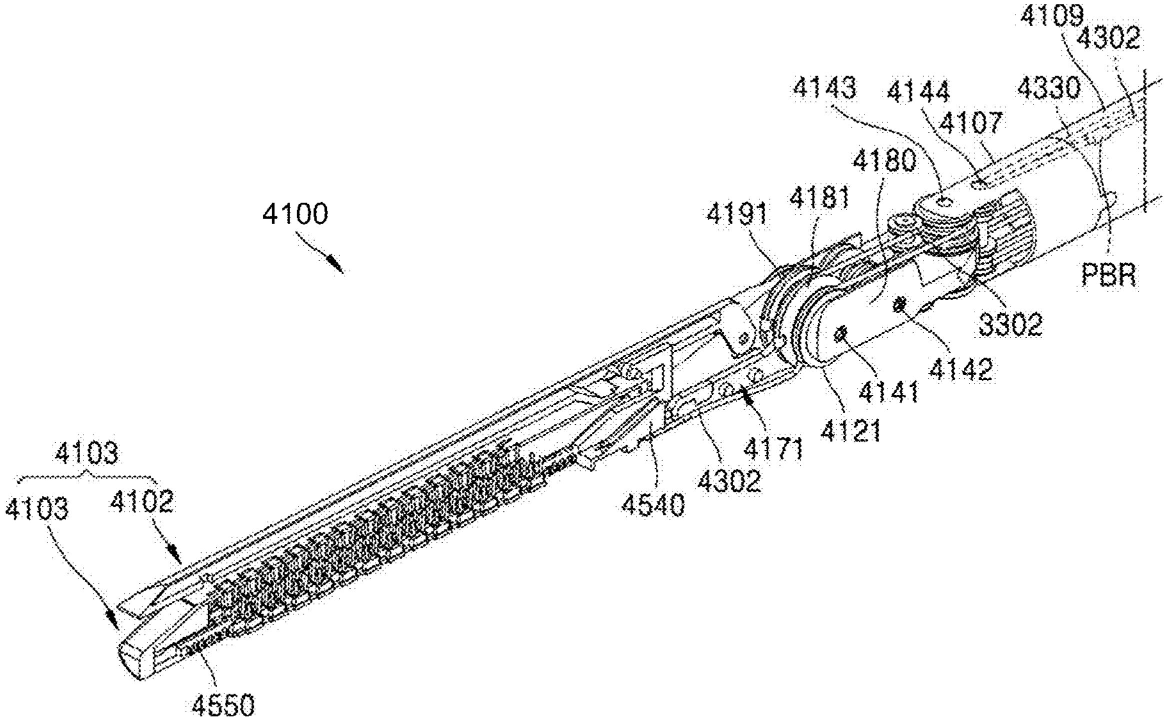
FIG. 69 is a perspective cross-sectional view illustrating an end tool of a surgical instrument according to another embodiment of the present disclosure.

FIG. 69 is a perspective cross-sectional view illustrating an end tool of a surgical instrument according to another embodiment of the present disclosure.

Referring to FIG. 69, an end tool 4100 of the surgical instrument according to the present embodiment may include a jaw 4103. For convenience of description, differences from the above-described embodiment will be mainly described. Specifically, the end tool 4100 of the present embodiment is different from the end tool 3100 of FIG. 63 described above in a detection member 4330 that detects a backward movement wire 4302, and thus, the difference will be mainly described.

The jaw 4103 may be formed to accommodate an operation member 4540 in at least one region thereof. The jaw 4103 may have various forms, such as being configured as one or more jaws, as a specific example, two jaws. For example, the jaw 4103 may include a first jaw 4101 and a second jaw 4102.

For example, the operation member 4540 may move forward (move toward a distal end).

Further, the operation member 4540 may move forward and then backward, and when the operation member 4540 changes in position due to its backward movement by the backward movement wire 4302, this change may be detected by the detection member 4330, For example, the movement and position of the backward movement wire 4302 may be detected using the detection member 4330 disposed on an inner side of an end tool shaft 4109, and in this case, a measuring member PBR further attached to the backward movement wire 4302 enables the detection member to more effectively detect the motion information of the backward movement wire 4302.

The operation member 4540 may receive a driving force through at least a reciprocating member of a reciprocating assembly 4550.

The backward movement wire 4302 may be connected to one region of the operation member 4540. The backward movement of the operation member 4540 may be performed through the backward movement wire 4302. For example, the backward movement wire 4302 may receive a force to move the operation member 4540 toward a proximal end of the jaw 4103, and in other words, the backward movement wire 4302 may be formed to pull the operation member 4540.

Although not shown in the drawings, a driving part or a driving transmission part (e.g., wires, pulleys, and the like)

capable of pulling the backward movement wire 4302 may be connected to the backward movement wire 4302, and the backward movement wire 4302 may be operated according to manual or automatic manipulation.

By pulling the backward movement wire 4302, the operation member 4540 may move backward.

The operation member 4540 may be moved forward by the reciprocating member 4551, and may remain stationary during the backward movement of the reciprocating member 4551 (see above-described embodiment).

At this time, the backward movement wire 4302 may be used to move the operation member 4540 backward to the desired extent.

The end tool 4100 of the present embodiment may include an end tool hub 4180 and a pitch hub 4107. The end tool hub 4180 may be formed such that one or more rotation shafts 4141 and 4142 are inserted therethrough and one or more pulleys (not shown) corresponding to the one or more rotation shafts 4141 and 4142 are disposed therein. In addition, at least some of the first jaw 4101 and the second jaw 4102 that are coupled to the rotation shaft 4141 or the rotation shaft 4142 may be accommodated inside the end tool hub 4180.

One or more rotation shafts 4143 and 4144 may be inserted through the pitch hub 4107, and the pitch hub 4107 may be axially coupled to the end tool hub 4180 by the rotation shaft 4143. Accordingly, the end tool hub 4180 may be formed to be pitch-rotatable around the rotation shaft 4143 with respect to the pitch hub 4107.

The backward movement wire 4302 may extend through the end tool hub 4180 and the pitch hub 4107 to the end tool shaft 4109, and may be disposed on the end tool shaft 4109 while a path thereof is being guided in correspondence with, for example, one or more pulleys disposed in the end tool hub 4180 and the pitch hub 4107. The end tool shaft 4109 may be an end portion of the manipulation part located at a side of a proximal end of the end tool 4100. For example, when the connection part (not shown) connecting the manipulation part to the end tool 4100 is disposed, the end tool shaft 4109 may be a region of the end tool 4100, which is adjacent to or connected to the connection part (not shown).

In addition, although not shown in the drawings, the backward movement wire 4302 may extend to the connection part (not shown) and a manipulation part (not shown) connected thereto via the end tool shaft 4109, and specifically, may be connected to a driving part (not shown) configured to drive the backward movement wire 4302.

The detection member 4330 may detect motion information of the backward movement wire 4302. For example, the detection member 4330 may have the form of a proximity sensor, which detects the motion or position of the backward movement wire 4302. The detection member 4330 may have an optically sensing form, or in other cases, may be formed as a contact-type sensor.

The detection member 4330 may be disposed in one region, such as, on or adjacent to an inner side surface, of the end tool shaft 4109 to detect motion or movement information of the backward movement wire 4302 without interrupting the motion thereof. In addition, the detection member 4330 may be disposed relatively wide or long, thereby forming a position sensor layer with improved precision.

In an optional embodiment, the measuring member PBR may be disposed in one region of the backward movement wire 4302. The measuring member PBR connected to the backward movement wire 4302 moves in response to the movement of the backward movement wire 4302, and the moving measuring member PBR is measured by the detection member 4330, thereby detecting the motion information of the backward movement wire 4302. Accordingly, it is possible to efficiently detect the motion information of the backward movement wire 4302 in a simple manner, and improve the accuracy of detected measurement values.

The contents of a staple pulley assembly including one or more staple pulleys 4181 and 4191 and a staple link assembly including one or more link members 4171, which are included in the end tool 4100, are substantially the same as those described in the embodiment described above.

Meanwhile, one or more pulleys 4121 associated with the rotational movement of the backward movement wire 4302 may be disposed.

The contents of a cartridge including a housing 4510 and the like, and a backward movement of the operation member 4540 using the operation member 4540 and the backward movement wire 4302 are substantially the same as those described in the embodiment described above, and thus a detailed description thereof will be omitted.

Since the end tool 4100 of the present embodiment can determine motion and position information of the operation member 4540, it is possible to precisely determine a status of each of steps in the process of performing an operation using the end tool 4100 and precisely control initiation of each step's progression.

For example, the process of using the end tool 4100 through the motion of the operation member 4540, specifically a stapling motion, can be performed safely and efficiently. As a result, each of steps of the stapling process can be precisely controlled.

In addition, the detection of the position of the operation member 4540 through movement and displacement detection of the backward movement wire 4302 during the forward or backward movement of the operation member 4540 is substantially the same as that described in the above-described embodiments.

Figure 70:
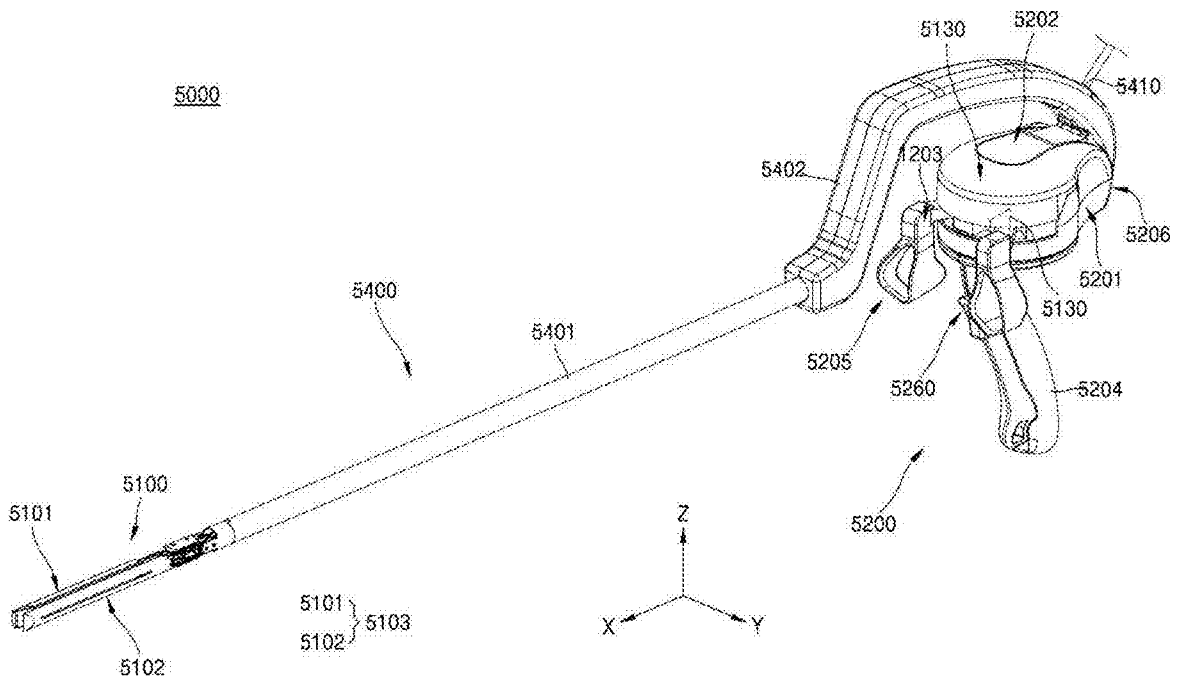
FIG. 70 is a schematic perspective view illustrating a surgical instrument according to another embodiment of the present disclosure.
Figure 71:
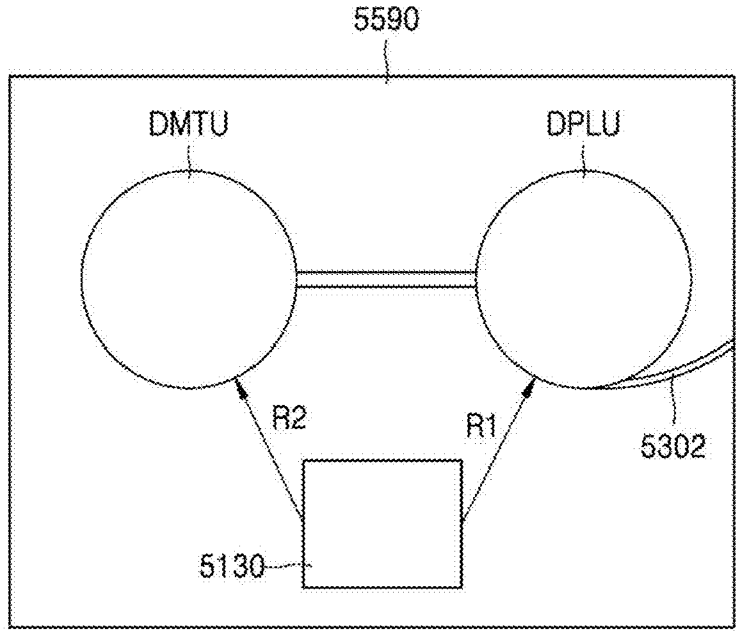
FIG. 71 is a view for describing a detection member of FIG. 70.

FIG. 70 is a schematic perspective view illustrating a surgical instrument according to another embodiment of the present disclosure. FIG. 71 is a view for describing a detection member of FIG. 70.

Referring to FIGS. 70 and 71, a surgical instrument 5000 of the present embodiment may include an end tool 5100. For convenience of description, differences from the above-described embodiment will be mainly described. Specifically, a detection member 5130 for detecting a motion of a backward movement wire 5302 is different, and thus will be mainly described.

The end tool 5100 is disposed in one region of the surgical instrument 5000, such as an end portion thereof, and may be inserted into a surgical site to perform a motion necessary for surgery. In addition, as an example, the end tool 5100 may be connected to a manipulation part 5200 through a connection part 5400 to be driven by the manipulation part 5200.

The end tool 5100 may include a jaw 5103. The jaw 5103 may include a first jaw 5101 and a second jaw 5102. The detailed contents of the configuration including the end tool 5100 and the jaw 5103 will not be described herein as any of the above-described embodiments may be adapted as it is, or various design modifications may be made as needed, such as by eliminating configurations that are necessary or unnecessary for the arrangement of the backward movement wire 5302.

The backward movement wire 5302 may be connected to one region of an operation member (e.g., 4540 in FIG. 69) disposed in the end tool 5100, and may be formed to move the operation member backward and pull the operation member. The backward movement wire 5302 may extend from the end tool 5100 to the manipulation part 5200 through the connection part 5400.

For example, the backward movement wire 5302 is connected to a backward movement driving part DMTU disposed on the manipulation part 5200, and may be pulled by the backward movement driving part DMTU. As a specific example, the backward movement driving part DMTU may include a driving member such as a motor, and a driving force of the backward movement driving part DMTU may be transmitted to the backward movement wire BRW through one or more driving control members DPLU, and the driving control member DPLU may include one or more pulleys.

The detection member 5130 may detect motion information of the backward movement wire 5302. For example, the detection member 5130 may detect a motion of the backward movement driving part DMTU, which causes the backward movement wire 5302 to move. As a specific example, the detection member 5130 may detect a rotation amount of the backward movement driving part DMTU when the backward movement driving part DMTU rotationally moves. In addition, as a specific example, the detection member 5130 may include an encoder configured to detect driving information R2 such as the number of rotations or rotation amount of a motor member included in the backward movement driving part DMTU.

In addition, as another example, the driving force of the backward movement driving part DMTU may be transmitted to the backward movement wire 5302 through the driving control member DPLU such as a pulley, and the detection member 5130 may be formed to detect driving control information R1 such as a rotation amount of the driving control member DPLU.

Further, although not shown in the drawings, in an optional embodiment, the detection member 5130 may be disposed inside the backward movement driving part DMTU or integrally formed with the backward movement driving part DMTU.

When the backward movement driving part DMTU pulling the backward movement wire 5302 moves, driving information such as a rotation amount of the backward movement driving part DMTU may be detected through the detection member 5130. By detecting this driving information, the degree of movement, such as the number of rotations, of the backward movement driving part DMTU may be detected, and accordingly, the degree of pulling the backward movement wire 5302 may be determined, and a length that the backward movement wire 5302 has moved backward may be determined. As a result, the motion information and the position of the operation member, which has been moved backward together with the backward movement wire 5302 by being connected thereto, may be determined. By determining the motion and position information of the operation member, it is possible to precisely determine a status of each of steps in the process of performing an operation using the end tool 5100 and precisely control initiation of each step's progression.

Meanwhile, the contents of FIGS. 11A to 11C described above may be optionally applied to the present embodiment. That is, as described above, during the forward movement of the operation member, the backward movement driving part DMTU may also rotate to actively transmit a driving force to the backward movement wire 5302 to move the backward movement wire 5302 forward in coordination with the driving of the driving part for the forward movement of the operation member, and in this case, the position of the backward movement driving part DMTU can be indirectly identified by measuring the rotation amount or number of rotations of the backward movement wire 5302. In addition, as another example, instead of the backward movement driving part DMTU actively moving during the forward movement of the operation member, the driving control member DPLU such as a pulley or the backward movement driving part DMTU may also be moved passively by the force resulting from the forward movement of the backward movement wire 5302, and even in this case, the position of the backward movement wire 5302 can be indirectly identified by measuring the rotation amount or number of rotations of the driving control member DPLU such as a pulley or the backward movement driving part DMTU.

For example, a stapling motion through the operation member may be safely and efficiently performed, and as a specific example, each of steps of a process in which stapling is performed may be precisely controlled. Although not shown in the drawings, a description of the operation of the surgical instrument of FIGS. 52 to 54 may also be applied to the surgical instrument 5000 of the present embodiment.

As described above, the present disclosure has been described with reference to the embodiment described with reference to the drawings, but it will be understood that this is merely exemplary, and those of ordinary skill in the art will understand that various modifications and other equivalent embodiments are possible therefrom. Accordingly, the true technical protection scope of the present disclosure should be defined by the technical spirit of the appended claims.

The embodiments may be represented by functional block elements and various processing steps. The functional blocks may be implemented as a varying number of hardware and/or software components that perform particular functions. For example, the embodiments may adopt integrated circuit configurations, such as memory, processing, logic, and/or look-up table, which may execute various functions by the control of one or more microprocessors or other control devices The particular implementations shown and described herein are illustrative examples of the embodiments and are not intended to otherwise limit the scope of the embodiments in any way. For the sake of brevity, conventional electronics, control methods, software development and other functional aspects of the methods may not be described in detail. Further, the connecting lines or connectors shown in the drawings are intended to represent example functional relationships and/or physical or logical couplings between the various elements. It should be noted that many alternative or additional functional relationships, physical connections, or logical connections may be present in a practical device. In addition, no item or element is essential to the practice of the present disclosure unless the element is specifically described as "essential" or "critical".

The use of the terms "a" and "an" and "the" and similar referents in the context of describing the present disclosure (especially in the context of the following claims) are to be construed to cover both the singular and the plural. Further, recitation of ranges of values herein are merely intended to serve as a shorthand method of referring individually to each separate value falling within the range, unless otherwise indicated herein, and each separate value is incorporated into the specification as if it were individually recited herein. Finally, steps of all methods described herein can be performed in any suitable order unless otherwise indicated herein or otherwise clearly contradicted by context. The present disclosure is not necessarily limited to the described order of the steps. The use of any and all examples, or exemplary terms (e.g., "such as") provided herein, is intended merely to better illuminate the present disclosure and does not pose a limitation on the scope of the present disclosure unless otherwise claimed. Further, numerous modifications and adaptations will be readily apparent to one of ordinary skill in the art without departing from the spirit and scope of the present disclosure.

A surgical instrument and an operation method of a surgical instrument according to the present disclosure can precisely and easily control the progression of one or more steps involved in performing a laparoscopic surgery or various other surgeries.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A surgical instrument comprising:

an end tool including a jaw;

a driving part; and a detection member, wherein the jaw is formed to accommodate at least one region of an operation member movable in one direction, the driving part includes a motor member and one or more pulleys connected to the motor member to transmit a driving force to the operation member, the detection member is configured to detect driving information of the driving part, position information of the operation member is determined by comparing the driving information detected by the detection member with reference information, and the reference information being information on a rotation amount of the motor member or a rotation amount of the one or more pulleys required for the operation member to move an entire distance from a distal end to a proximal end of the jaw.

2. The surgical instrument of claim 1, wherein the detection member is formed to detect the rotation amount of the motor member, and the position information of the operation member is determined by comparing the reference information with the rotation amount of the motor member detected by the detection member.

3. The surgical instrument of claim 1, wherein the detection member detects the rotational motion of the one or more pulleys, and the position information of the operation member is determined by comparing the reference information with the rotation amount of the one or more pulleys detected by the detection member.

4. The surgical instrument of claim 1, wherein the detection member is disposed inside the driving part or is integrally formed with the driving part.

5. The surgical instrument of claim 1, further comprising a manipulation part configured to manipulate an operation of the end tool, wherein the driving part and the detection member are disposed inside the manipulation part.

6. The surgical instrument of claim 1, wherein whether the operation member reaches a set stop position, which is set in advance, is determined using the position information of the operation member, and the operation member is formed to stop movement thereof upon reaching the set stop position and remain stationary for a set waiting time, and to resume forward movement or change into a state capable of forward movement after the set waiting time.

7. The surgical instrument of claim 6, wherein the set stop position is a position corresponding to a close motion completion state of the jaw, and as the operation member moves after the set waiting time, a stapling process of the end tool proceeds to a firing state.

8. The surgical instrument of claim 1, comprising a manipulation part configured to control an operation of the end tool; and a connection part configured to connect the manipulation part to the end tool.

9. The surgical instrument of claim 8, wherein the end tool is formed to be yaw-rotatable around one shaft and pitch-rotatable around another shaft different from the one shaft.

10. A method of driving the surgical instrument of claim 1, comprising a surgical procedure including one or more steps using the surgical instrument, wherein a position of the operation member is determined through the detection member before performing one step.

11. The method of claim 10, wherein, in the surgical procedure including one or more steps using the surgical instrument, the steps include:

a step of determining, using the position information of the operation member, whether the operation member reaches a set stop position, which is a position set in advance, when the operation member moves forward;

a step of controlling the operation member to stop movement thereof for a set waiting time, which is set in advance, when it is determined that the operation member has reached the set stop position; and a step of changing a state of the operation member to a state in which a command of a forward movement is inputtable or moving the operation member forward when the set waiting time has passed.

* * * * *